United States Patent
Brown et al.

(10) Patent No.: US 10,953,019 B2
(45) Date of Patent: Mar. 23, 2021

(54) FUSED PENTACYCLIC IMIDAZOLE DERIVATIVES AS MODULATORS OF TNF ACTIVITY

(71) Applicants: UCB Biopharma SRL, Brussels (BE); Sanofi, Paris (FR)

(72) Inventors: Julien Alistair Brown, Slough (GB); Daniel Christopher Brookings, Slough (GB); Jag Paul Heer, Slough (GB); James Andrew Johnson, Slough (GB); Zhaoning Zhu, Slough (GB)

(73) Assignees: UCB Biopharma SRL, Brussels (BE); Sanofi, Paris (FR)

( * ) Notice: Subject to any disclaimer, the term of this patent is extended or adjusted under 35 U.S.C. 154(b) by 0 days.

(21) Appl. No.: 16/487,988

(22) PCT Filed: Mar. 14, 2018

(86) PCT No.: PCT/EP2018/056450
§ 371 (c)(1),
(2) Date: Aug. 22, 2019

(87) PCT Pub. No.: WO2018/167176
PCT Pub. Date: Sep. 20, 2018

(65) Prior Publication Data
US 2020/0022988 A1 Jan. 23, 2020

(30) Foreign Application Priority Data
Mar. 15, 2017 (EP) .................... 17161170

(51) Int. Cl.
*A61K 31/55* (2006.01)
*C07D 471/22* (2006.01)

(52) U.S. Cl.
CPC ............ *A61K 31/55* (2013.01); *C07D 471/22* (2013.01)

(58) Field of Classification Search
CPC ... C07D 471/18; C07D 471/22; C07D 487/18
See application file for complete search history.

(56) References Cited

U.S. PATENT DOCUMENTS 7,067,507 B2 * 6/2006 Pulley ............... A61P 43/00
514/183

FOREIGN PATENT DOCUMENTS

| WO | WO 2004/087720 | 10/2004 |
|---|---|---|
| WO | WO 2009/156091 | 12/2009 |
| WO | WO 2012/135082 | 10/2012 |
| WO | WO 2012/177707 | 12/2012 |
| WO | WO 2013/186229 | 12/2013 |
| WO | WO 2014/009295 | 1/2014 |
| WO | WO 2014/009296 | 1/2014 |
| WO | WO 2015/086501 | 6/2015 |
| WO | WO 2015/086509 | 6/2015 |
| WO | WO 2015/086519 | 6/2015 |
| WO | WO 2016/050975 | 4/2016 |
| WO | WO 2016/149436 | 9/2016 |
| WO | WO 2016/149437 | 9/2016 |

OTHER PUBLICATIONS

Wong. Clinical Immunology, 2008, 126, 121-136 (Year: 2008).*
Tansey & Szymkowski (2009) Drug Discovery Today 14, 1082-1088.
Carneiro et al (2010) J Sexual Medicine 7, 3823-3834.
Wu et al (2013) JAMA 309, 2043-2044.
Hauwermeiren et al (2013) J. Clin. Invest. 123, 2590-2603.
Eichman & Stambuli (2009) J. Org. Chem. 74, 4005-4008.
Bahrami et al (2009) J. Org. Chem. 74, 9287-9291.
Armstrong et al (2013) J. Org. Chem. 78, 10534.
Sakai et al (2007) J. Org. Chem. 72, 5920-5922.
Okamura et al (2004) Organic Letters 6(8) 1305-1307.
Nagib & MacMillan (2011) Nature 480, 224.
Bentley et al (2002) Organic Process Research & Development 6, 109-112.
Nam et al (2004) Bio-org. med. Chem. 12, 6255.
Lacko et al, Current Medicinal Chemistry, 2012, 19, 4699.

* cited by examiner

*Primary Examiner* — Noble E Jarrell
(74) *Attorney, Agent, or Firm* — McDonnell Boehnen Hulbert & Berghoff LLP

(57) ABSTRACT

A series of substituted fused pentacyclic imidazopyridine and imidazopyridazine derivatives, and analogues thereof, being potent modulators of human TNFα activity, are accordingly of benefit in the treatment and/or prevention of various human ailments, including autoimmune and inflammatory disorders; neurological and neurodegenerative disorders; pain and nociceptive disorders; cardiovascular disorders; metabolic disorders; ocular disorders; and oncological disorders.

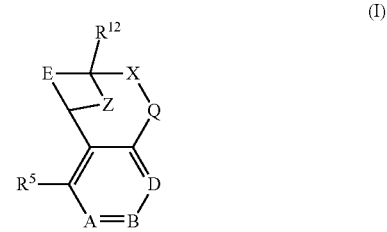

12 Claims, No Drawings

FUSED PENTACYCLIC IMIDAZOLE DERIVATIVES AS MODULATORS OF TNF ACTIVITY

This application is a U.S. national phase application under 35 USC 371 of International Patent Application no. PCT/EP2016/056450, filed Mar. 14, 2018, which claims the benefit of European Application no. 17161170.0, filed Mar. 15, 2017.

The present invention relates to a class of fused pentacyclic imidazole derivatives, and to their use in therapy. More particularly, this invention is concerned with pharmacologically active substituted fused pentacyclic imidazopyridine and imidazopyridazine derivatives, and analogues thereof. These compounds are modulators of the signalling of TNFα, and are accordingly of benefit as pharmaceutical agents, especially in the treatment of adverse inflammatory and autoimmune disorders, neurological and neurodegenerative disorders, pain and nociceptive disorders, cardiovascular disorders, metabolic disorders, ocular disorders, and oncological disorders.

TNFα is the prototypical member of the Tumour Necrosis Factor (TNF) superfamily of proteins that share a primary function of regulating cell survival and cell death. One structural feature common to all known members of the TNF superfamily is the formation of trimeric complexes that bind to, and activate, specific TNF superfamily receptors. By way of example, TNFα exists in soluble and transmembrane forms and signals through two receptors, known as TNFR1 and TNFR2, with distinct functional endpoints.

Various products capable of modulating TNFα activity are already commercially available. All are approved for the treatment of inflammatory and autoimmune disorders such as rheumatoid arthritis and Crohn's disease. All currently approved products are macromolecular and act by inhibiting the binding of human TNFα to its receptor. Typical macromolecular TNFα inhibitors include anti-TNFα antibodies; and soluble TNFα receptor fusion proteins. Examples of commercially available anti-TNFα antibodies include fully human antibodies such as adalimumab (Humira®) and golimumab (Simponi®), chimeric antibodies such as infliximab (Remicade®), and pegylated Fab' fragments such as certolizumab pegol (Cimzia®). An example of a commercially available soluble TNFα receptor fusion protein is etanercept (Enbrel®).

TNF superfamily members, including TNFα itself, are implicated in a variety of physiological and pathological functions that are believed to play a part in a range of conditions of significant medical importance (see, for example, M. G. Tansey & D. E. Szymkowski, *Drug Discovery Today*, 2009, 14, 1082-1088; and F. S. Carneiro et al., *J. Sexual Medicine*, 2010, 7, 3823-3834).

The compounds in accordance with the present invention, being potent modulators of human TNFα activity, are therefore beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

In addition, the compounds in accordance with the present invention may be beneficial as pharmacological standards for use in the development of new biological tests and in the search for new pharmacological agents. Thus, in one embodiment, the compounds of this invention may be useful as radioligands in assays for detecting pharmacologically active compounds. In an alternative embodiment, certain compounds of this invention may be useful for coupling to a fluorophore to provide fluorescent conjugates that can be utilised in assays (e.g. a fluorescence polarisation assay) for detecting pharmacologically active compounds.

WO 2015/086501, WO 2015/086509 and WO 2015/086519 relate to fused bicyclic imidazole derivatives which are modulators of the signalling of TNFα.

WO 2016/149436 and WO 2016/149437 relate to fused tricyclic imidazole derivatives which are modulators of the signalling of TNFα.

WO 2016/050975 relates to fused pentacyclic imidazole derivatives which are modulators of the signalling of TNFα.

None of the prior art available to date, however, discloses or suggests the precise structural class of fused pentacyclic imidazole derivatives as provided by the present invention.

The present invention provides a compound of formula (I) or an N-oxide thereof, or a pharmaceutically acceptable salt thereof:

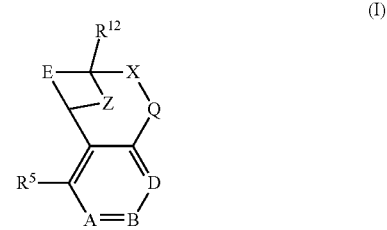

wherein
A represents N or C—$R^6$;
B represents N or C—$R^7$;
D represents N or C—$R^8$;
—X-Q- represents —O—, —O—C(O)—, —C(O)—O—, —O—C(=CH—CN)—, —S—, —SO—, —SO$_2$—, —N($R^g$)—, —N($R^f$)—CO—, —CO—N($R^f$)—, —N($R^f$)—SO$_2$—, —SO$_2$—N($R^f$)—, —S(O)(N$R^f$)—, —N($R^f$)—C(S)—, —N=S(O)(CH$_3$)—, —O—C(=CH$_2$)— or —S(=N—CN)—; or —X-Q- represents —CH$_2$—CH$_2$—, —O—CH$_2$—, —CH$_2$—O—, —S—CH$_2$—, —SO—CH$_2$—, —SO$_2$—CH$_2$—, —CH$_2$—S—, —CH$_2$—SO—, —CH$_2$—SO$_2$—, —N($R^g$)—CH$_2$—, —CH$_2$—N($R^g$)—, —S(O)(N$R^f$)—CH$_2$— or —CH$_2$—S(O)(N$R^f$)—, any of which groups may be optionally substituted by one or more substituents;
Z represents methylene;
E represents a fused heteroaromatic ring system selected from the groups of formula (Ea), (Eb) and (Ec):

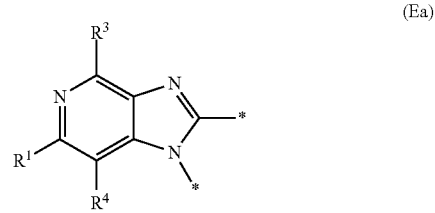

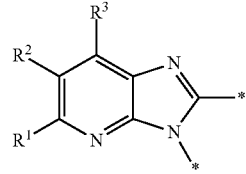

-continued

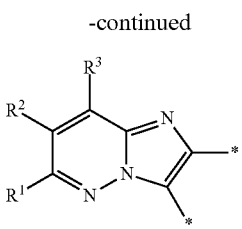

(Ec)

wherein the asterisks (*) represent the site of attachment of E to the remainder of the molecule;

$R^1$ represents hydrogen, halogen, cyano, trifluoromethyl, trifluoromethoxy, —$OR^a$, —$SR^a$, —$SOR^a$, —$SO_2R^a$, —$NR^bR^c$, —$NR^cCOR^d$, —$NR^cCO_2R^d$, —$NHCONR^bR^c$, —$NR^cSO_2R^e$, —$COR^d$, —$CO_2R^d$, —$CONR^bR^c$, —$SO_2NR^bR^c$, or —$S(O)(N—R^b)R^e$; or $R^1$ represents $C_{1-6}$ alkyl, $C_{3-7}$ cycloalkyl, $C_{4-7}$ cycloalkenyl, aryl, aryl($C_{1-6}$)alkyl, $C_{3-7}$ heterocycloalkyl, $C_{3-7}$ heterocycloalkenyl, heteroaryl, heteroaryl($C_{1-6}$)alkyl, ($C_{3-7}$)heterocycloalkyl($C_{1-6}$)alkyl-aryl-, ($C_{3-7}$)heterocycloalkenyl-aryl-, ($C_{3-7}$)cycloalkyl-heteroaryl-, ($C_{3-7}$)cycloalkyl-($C_{1-6}$)alkyl-heteroaryl-, ($C_{4-7}$)cycloalkenyl-heteroaryl-, ($C_{4-9}$)bicycloalkyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents;

$R^2$ represents hydrogen, halogen, cyano, nitro, hydroxy, trifluoromethyl, trifluoromethoxy or —$OR^a$; or $R^2$ represents $C_{1-6}$ alkyl or heteroaryl, either of which groups may be optionally substituted by one or more substituents;

$R^3$ and $R^4$ independently represent hydrogen, halogen or trifluoromethyl; or $C_{1-6}$ alkyl, which group may be optionally substituted by one or more substituents;

$R^5$ represents hydrogen, halogen, hydroxy, cyano, trifluoromethyl, difluoromethoxy, trifluoromethoxy, —$OR^a$ or $C_{1-6}$ alkylsulphonyl; or $R^5$ represents $C_{1-6}$ alkyl, which group may be optionally substituted by one or more substituents;

$R^6$, $R^7$ and $R^8$ independently represent hydrogen, halogen, trifluoromethyl, $C_{1-6}$ alkyl or $C_{1-6}$ alkoxy;

$R^{12}$ represents hydrogen or $C_{1-6}$ alkyl;

$R^a$ represents $C_{1-6}$ alkyl, $C_{3-7}$ cycloalkyl, aryl, aryl($C_{1-6}$)alkyl, $C_{3-7}$ heterocycloalkyl, heteroaryl or heteroaryl($C_{1-6}$)alkyl, any of which groups may be optionally substituted by one or more substituents;

$R^b$ and $R^c$ independently represent hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^b$ and $R^c$, when taken together with the nitrogen atom to which they are both attached, represent a heterocyclic moiety selected from azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl, homopiperazin-1-yl, (imino)(oxo)thiazinan-4-yl, (oxo)thiazinan-4-yl and (dioxo)thiazinan-4-yl, any of which groups may be optionally substituted by one or more substituents;

$R^d$ represents hydrogen; or $R^d$ represents $C_{1-6}$ alkyl, $C_{3-7}$ cycloalkyl, aryl, $C_{3-7}$ heterocycloalkyl or heteroaryl, any of which groups may be optionally substituted by one or more substituents;

$R^e$ represents $C_{1-6}$ alkyl, aryl or heteroaryl, any of which groups may be optionally substituted by one or more substituents;

$R^f$ represents hydrogen; or $R^f$ represents $C_{1-6}$ alkyl, $C_{3-7}$ cycloalkyl or $C_{3-7}$ heterocycloalkyl, any of which groups may be optionally substituted by one or more substituents; and $R^g$ represents hydrogen, —$SO_2R^a$, —$COR^d$ or —$CO_2R^d$; or $R^g$ represents $C_{1-6}$ alkyl, $C_{3-7}$ cycloalkyl, $C_{3-7}$ heterocycloalkyl or heteroaryl, any of which groups may be optionally substituted by one or more substituents.

The present invention also provides a compound of formula (I) as defined above or an N-oxide thereof, or a pharmaceutically acceptable salt thereof, for use in therapy.

The present invention also provides a compound of formula (I) as defined above or an N-oxide thereof, or a pharmaceutically acceptable salt thereof, for use in the treatment and/or prevention of disorders for which the administration of a modulator of TNFα function is indicated.

In another aspect, the present invention provides a compound of formula (I) as defined above or an N-oxide thereof, or a pharmaceutically acceptable salt thereof, for use in the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides the use of a compound of formula (I) as defined above or an N-oxide thereof, or a pharmaceutically acceptable salt thereof, for the manufacture of a medicament for the treatment and/or prevention of disorders for which the administration of a modulator of TNFα function is indicated.

In another aspect, the present invention provides the use of a compound of formula (I) as defined above or an N-oxide thereof, or a pharmaceutically acceptable salt thereof, for the manufacture of a medicament for the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides a method for the treatment and/or prevention of disorders for which the administration of a modulator of TNFα function is indicated which comprises administering to a patient in need of such treatment an effective amount of a compound of formula (I) as defined above or an N-oxide thereof, or a pharmaceutically acceptable salt thereof.

In another aspect, the present invention provides a method for the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder, which comprises administering to a patient in need of such treatment an effective amount of a compound of formula (I) as defined above or an N-oxide thereof, or a pharmaceutically acceptable salt thereof.

Where any of the groups in the compounds of formula (I) above is stated to be optionally substituted, this group may be unsubstituted, or substituted by one or more substituents. Typically, such groups will be unsubstituted, or substituted by one or two substituents.

The present invention includes within its scope salts of the compounds of formula (I) above. For use in medicine, the salts of the compounds of formula (I) will be pharmaceutically acceptable salts. Other salts may, however, be useful in the preparation of the compounds of use in the invention or of their pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002.

The present invention includes within its scope solvates of the compounds of formula (I) above. Such solvates may be formed with common organic solvents or water.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012).

Suitable alkyl groups which may be present on the compounds in accordance with the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Suitable alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

The term "$C_{3-7}$ cycloalkyl" as used herein refers to monovalent groups of 3 to 7 carbon atoms derived from a saturated monocyclic hydrocarbon, and may comprise benzo-fused analogues thereof. Suitable $C_{3-7}$ cycloalkyl groups include cyclopropyl, cyclobutyl, benzocyclobutenyl, cyclopentyl, indanyl, cyclohexyl and cycloheptyl.

The term "$C_{4-7}$ cycloalkenyl" as used herein refers to monovalent groups of 4 to 7 carbon atoms derived from a partially unsaturated monocyclic hydrocarbon. Suitable $C_{4-7}$ cycloalkenyl groups include cyclobutenyl, cyclopentenyl, cyclohexenyl and cycloheptenyl.

The term "$C_{4-9}$ bicycloalkyl" as used herein refers to monovalent groups of 4 to 9 carbon atoms derived from a saturated bicyclic hydrocarbon. Typical bicycloalkyl groups include bicyclo[3.1.0]hexanyl, bicyclo[4.1.0]heptanyl and bicyclo[2.2.2]octanyl.

The term "aryl" as used herein refers to monovalent carbocyclic aromatic groups derived from a single aromatic ring or multiple condensed aromatic rings. Suitable aryl groups include phenyl and naphthyl, preferably phenyl.

Suitable aryl($C_{1-6}$)alkyl groups include benzyl, phenylethyl, phenylpropyl and naphthylmethyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Suitable heterocycloalkyl groups include oxetanyl, azetidinyl, tetrahydrofuranyl, dihydrobenzo-furanyl, dihydrobenzothienyl, pyrrolidinyl, indolinyl, isoindolinyl, oxazolidinyl, thiazolidinyl, isothiazolidinyl, imidazolidinyl, tetrahydropyranyl, chromanyl, dioxanyl, tetrahydrothiopyranyl, piperidinyl, 1,2,3,4-tetrahydroquinolinyl, 1,2,3,4-tetrahydro-isoquinolinyl, piperazinyl, 1,2,3,4-tetrahydroquinoxalinyl, hexahydro-[1,2,5]thiadiazolo-[2,3-a]pyrazinyl, homopiperazinyl, morpholinyl, benzoxazinyl, thiomorpholinyl, azepanyl, oxazepanyl, diazepanyl, thiadiazepanyl and azocanyl.

The term "$C_{3-7}$ heterocycloalkenyl" as used herein refers to monounsaturated or polyunsaturated monocyclic rings containing 3 to 7 carbon atoms and at least one heteroatom selected from oxygen, sulphur and nitrogen, and may comprise benzo-fused analogues thereof. Suitable heterocycloalkenyl groups include thiazolinyl, imidazolinyl, dihydropyranyl, dihydrothiopyranyl and 1,2,3,6-tetrahydropyridinyl.

The term "$C_{4-9}$ heterobicycloalkyl" as used herein corresponds to $C_{4-9}$ bicycloalkyl wherein one or more of the carbon atoms have been replaced by one or more heteroatoms selected from oxygen, sulphur and nitrogen. Typical heterobicycloalkyl groups include 3-azabicyclo[3.1.0]hexanyl, 2-oxa-5-azabicyclo[2.2.1]heptanyl, 6-azabicyclo[3.2.0] heptanyl, 3-azabicyclo[3.1.1]heptanyl, 3-azabicyclo[4.1.0] heptanyl, 2-oxabicyclo[2.2.2]octanyl, quinuclidinyl, 2-oxa-5-azabicyclo[2.2.2]octanyl, 3-azabicyclo[3.2.1]octanyl, 8-azabicyclo-[3.2.1]octanyl, 3-oxa-8-azabicyclo[3.2.1]octanyl, 3,8-diazabicyclo[3.2.1]octanyl, 3,6-diazabicyclo[3.2.2] nonanyl, 3-oxa-7-azabicyclo[3.3.1]nonanyl, 3,7-dioxa-9-azabicyclo-[3.3.1]nonanyl and 3,9-diazabicyclo[4.2.1] nonanyl.

The term "$C_{4-9}$ spiroheterocycloalkyl" as used herein refers to saturated bicyclic ring systems containing 4 to 9 carbon atoms and at least one heteroatom selected from oxygen, sulphur and nitrogen, in which the two rings are linked by a common atom. Suitable spiroheterocycloalkyl groups include 5-azaspiro[2.3]hexanyl, 5-azaspiro[2.4]-heptanyl, 2-azaspiro[3.3]heptanyl, 2-oxa-6-azaspiro[3.3]heptanyl, 2-oxa-6-azaspiro[3.4]-octanyl, 2-oxa-6-azaspiro[3.5] nonanyl, 7-oxa-2-azaspiro[3.5]nonanyl, 2-oxa-7-azaspiro-[3.5]nonanyl and 2,4,8-triazaspiro[4.5]decanyl.

The term "heteroaryl" as used herein refers to monovalent aromatic groups containing at least 5 atoms derived from a single ring or multiple condensed rings, wherein one or more carbon atoms have been replaced by one or more heteroatoms selected from oxygen, sulphur and nitrogen. Suitable heteroaryl groups include furyl, benzofuryl, dibenzofuryl, thienyl, benzothienyl, thieno[2,3-c]pyrazolyl, thieno[3,4-b] [1,4]dioxinyl, dibenzothienyl, pyrrolyl, indolyl, pyrrolo[2,3-b]pyridinyl, pyrrolo[3,2-c]pyridinyl, pyrrolo[3,4-b]pyridinyl, pyrazolyl, pyrazolo[1,5-a]pyridinyl, pyrazolo[3,4-d] pyrimidinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[2,1-b]thiazolyl, imidazo[1,2-a]pyridinyl, imidazo[4,5-b]pyridinyl, purinyl, imidazo[1,2-a]pyrimidinyl, imidazo[1,2-a] pyrazinyl, oxadiazolyl, thiadiazolyl, triazolyl, [1,2,4] triazolo[1,5-a]-pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds in accordance with the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$)↔enol (CH=CHOH) tautomers or amide (NHC=O)↔hydroxyimine (N=COH) tautomers. Formula (I) and the formulae depicted hereinafter are intended to represent all individual tautomers and all possible mixtures thereof, unless stated or shown otherwise.

As will be appreciated, 2-oxo-(1H)-pyridinyl is a tautomer of 2-hydroxypyridinyl; and 2-oxo-(1H)-pyrimidinyl is a tautomer of 2-hydroxypyrimidinyl.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium; D) or $^3H$ (tritium; T) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

A particular sub-class of compounds in accordance with the present invention is represented by formula (IA) or an N-oxide thereof, or a pharmaceutically acceptable salt thereof:

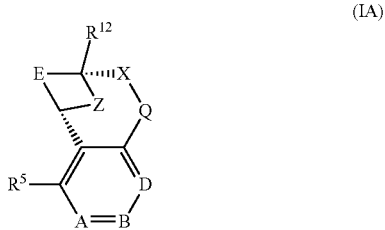

(IA)

wherein A, B, D, —X-Q-, Z, E, $R^5$ and $R^{12}$ are as defined above.

In a first embodiment, A represents N. In a second embodiment, A represents C—$R^6$.

In a first embodiment, B represents N. In a second embodiment, B represents C—$R^7$.

In a first embodiment, D represents N. In a second embodiment, D represents C—$R^8$.

In a first embodiment, A, B and D all represent N. In a second embodiment, A and B both represent N, and D represents C—$R^8$. In a third embodiment, A and D both represent N, and B represents C—$R^7$. In a fourth embodiment, A represents N, B represents C—$R^7$, and D represents C—$R^8$. In a fifth embodiment, A represents C—$R^6$, and B and D both represent N. In a sixth embodiment, A represents C—$R^6$, B represents N, and D represents C—$R^8$. In a seventh embodiment, A represents C—$R^6$, B represents C—$R^7$, and D represents N. In an eighth embodiment, A represents C—$R^6$, B represents C—$R^7$, and D represents C—$R^8$.

In a first embodiment, —X-Q- represents —O—. In a second embodiment, —X-Q- represents —O—C(O)—. In a third embodiment, —X-Q- represents —C(O)—O—. In a fourth embodiment, —X-Q- represents —O—C(=CH—CN)—. In a fifth embodiment, —X-Q- represents —S—. In a sixth embodiment, —X-Q- represents —SO—. In a seventh embodiment, —X-Q-represents —$SO_2$—. In an eighth embodiment, —X-Q- represents —N($R^g$)—. In a ninth embodiment, —X-Q- represents —N($R^f$)—CO—. In a tenth embodiment, —X-Q- represents —CO—N($R^f$)—. In an eleventh embodiment, —X-Q- represents —N($R^f$)—$SO_2$—. In a twelfth embodiment, —X-Q- represents —$SO_2$—N($R^f$)—. In a thirteenth embodiment, —X-Q-represents —S(O)(N$R^f$)—. In a fourteenth embodiment, —X-Q- represents optionally substituted —$CH_2$—$CH_2$—. In one aspect of that embodiment, —X-Q- represents —$CH_2$—$CH_2$—. In a fifteenth embodiment, —X-Q- represents optionally substituted —O—$CH_2$—. In one aspect of that embodiment, —X-Q- represents —O—$CH_2$—. In a sixteenth embodiment, —X-Q-represents optionally substituted —$CH_2$—O—. In one aspect of that embodiment, —X-Q-represents —$CH_2$—O—. In a seventeenth embodiment, —X-Q- represents optionally substituted —S—$CH_2$—. In one aspect of that embodiment, —X-Q- represents —S—$CH_2$—. In an eighteenth embodiment, —X-Q- represents optionally substituted —SO—$CH_2$—. In one aspect of that embodiment, —X-Q- represents —SO—$CH_2$—. In a nineteenth embodiment, —X-Q-represents optionally substituted —$SO_2$—$CH_2$—. In one aspect of that embodiment, —X-Q-represents —$SO_2$—$CH_2$—. In a twentieth embodiment, —X-Q- represents optionally substituted —$CH_2$—S—. In one aspect of that embodiment, X-Q- represents —$CH_2$—S—. In a twenty-first embodiment, —X-Q- represents optionally substituted —$CH_2$—SO—. In one aspect of that embodiment, —X-Q- represents —$CH_2$—SO—. In a twenty-second embodiment, —X-Q- represents optionally substituted —$CH_2$—$SO_2$—. In one aspect of that embodiment, —X-Q-represents —$CH_2$—$SO_2$—. In a twenty-third embodiment, —X-Q- represents optionally substituted —N($R^g$)—$CH_2$—. In one aspect of that embodiment, —X-Q- represents —N($R^g$)—$CH_2$—. In a twenty-fourth embodiment, —X-Q-represents optionally substituted —$CH_2$—N($R^g$)—. In one aspect of that embodiment, —X-Q- represents —$CH_2$—N($R^g$)—. In a twenty-fifth embodiment, —X-Q- represents optionally substituted —S(O)(N$R^f$)—$CH_2$—. In one aspect of that embodiment, —X-Q- represents —S(O)(N$R^f$)—$CH_2$—. In a twenty-sixth embodiment, —X-Q- represents optionally substituted —$CH_2$—S(O)(N$R^f$)—. In one aspect of that embodiment, —X-Q- represents —$CH_2$—S(O)(N$R^f$)—. In a twenty-seventh embodiment, —X-Q- represents —N($R^f$)—C(S)—. In a twenty-eighth embodiment, —X-Q- represents —N=S(O)($CH_3$)—. In a twenty-ninth embodiment, —X-Q- represents —O—C(=$CH_2$)—. In a thirtieth embodiment —X-Q- represents —S(=N—CN)—.

Typical examples of optional substituents on —X-Q- include halogen, $C_{1-6}$ alkyl, hydroxy($C_{1-6}$)alkyl, trifluoromethyl, $C_{2-6}$ alkylcarbonyl, carboxy and $C_{2-6}$ alkoxycarbonyl.

Typical examples of particular substituents on —X-Q- include fluoro, methyl, deuterated methyl, hydroxymethyl, hydroxyisopropyl, trifluoromethyl, acetyl, carboxy and ethoxycarbonyl.

Typically, —X-Q- represents —O—, —O—C(O)—, —O—C(=CH—CN)—, —S—, —SO—, —$SO_2$—, —N($R^g$)—, —N($R^f$)—CO—, —N($R^f$)—$SO_2$—, —N($R^f$)—C(S)—, —N=S(O)($CH_3$)—, —O—C(=$CH_2$)— or —S(=N—CN)—; or —X-Q- represents —O—$CH_2$—, —$CH_2$—S—, —$CH_2$—SO—, —$CH_2$—$SO_2$— or —N($R^g$)—$CH_2$—, any of which groups may be optionally substituted.

Suitably, —X-Q- represents —N($R^g$)— or —N($R^f$)—CO—.

Generally, E represents a fused heteroaromatic ring system of formula (Ea) or (Eb).

In a first embodiment, E represents a fused heteroaromatic ring system of formula (Ea).

In a second embodiment, E represents a fused heteroaromatic ring system of formula (Eb).

In a third embodiment, E represents a fused heteroaromatic ring system of formula (Ec).

Particular sub-classes of compounds in accordance with the present invention include the compounds of formula (IB), (IC) and (ID) and N-oxides thereof, and pharmaceutically acceptable salts thereof:

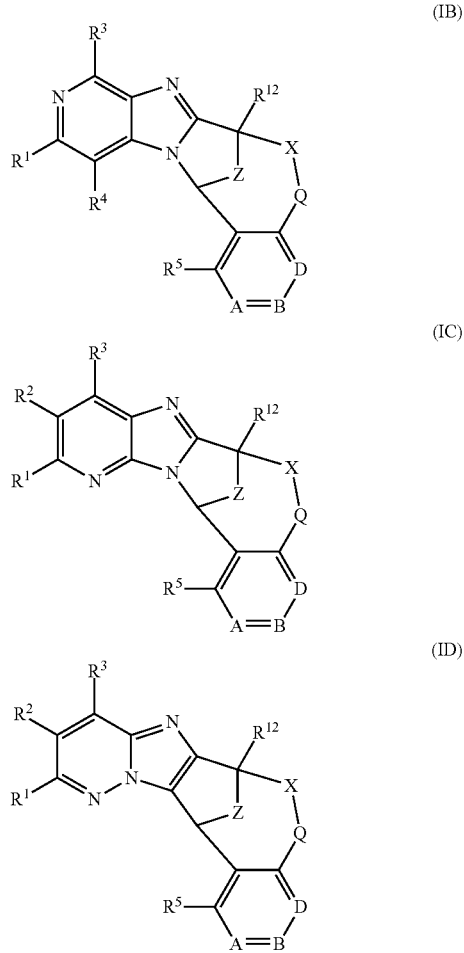

wherein A, B, D, —X-Q-, Z, $R^1$, $R^2$, $R^3$, $R^4$, $R^5$ and $R^{12}$ are as defined above.

Particular sub-classes of compounds in accordance with the present invention include the compounds of formula (IB) and (IC) as defined above.

Generally, $R^1$ represents hydrogen, halogen or cyano; or $R^1$ represents aryl, $C_{3-7}$ heterocycloalkyl, $C_{3-7}$ heterocycloalkenyl, heteroaryl, heteroaryl-aryl-, ($C_{3-7}$)cycloalkyl-heteroaryl-, ($C_{4-9}$)bicycloalkyl-heteroaryl-, ($C_{3-7}$)heterocycloalkyl-heteroaryl-, ($C_{4-9}$)-heterobicycloalkyl-heteroaryl- or ($C_{4-9}$)spiroheterocycloalkyl-heteroaryl-, any of which groups may be optionally substituted by one or more substituents.

Typically, $R^1$ represents halogen; or $R^1$ represents $C_{3-7}$ heterocycloalkyl, heteroaryl, ($C_{3-7}$)cycloalkyl-heteroaryl-, ($C_{3-7}$)heterocycloalkyl-heteroaryl- or ($C_{4-9}$)-heterobicycloalkyl-heteroaryl-, any of which groups may be optionally substituted by one or more substituents.

Suitably, $R^1$ represents halogen; or $R^1$ represents heteroaryl or ($C_{3-7}$)cycloalkyl-heteroaryl-, either of which groups may be optionally substituted by one or more substituents.

More suitably, $R^1$ represents heteroaryl or ($C_{3-7}$)cycloalkyl-heteroaryl-, either of which groups may be optionally substituted by one or more substituents.

In a first embodiment, $R^1$ represents hydrogen.

In a second embodiment, $R^1$ represents halogen. In one aspect of that embodiment, $R^1$ represents fluoro. In another aspect of that embodiment, $R^1$ represents chloro.

In a third embodiment, $R^1$ represents cyano.

In a fourth embodiment, $R^1$ represents optionally substituted aryl. In one aspect of that embodiment, $R^1$ represents optionally substituted phenyl.

In fifth embodiment, $R^1$ represents optionally substituted $C_{3-7}$ heterocycloalkyl. In one aspect of that embodiment, $R^1$ represents optionally substituted azetidinyl.

In a sixth embodiment, $R^1$ represents optionally substituted ($C_{3-7}$)heterocycloalkenyl. In a first aspect of that embodiment, $R^1$ represents optionally substituted 1,2-dihydropyridinyl. In a second aspect of that embodiment, $R^1$ represents optionally substituted 1,2-dihydropyrimidinyl.

In a seventh embodiment, $R^1$ represents optionally substituted heteroaryl. In one aspect of that embodiment, $R^1$ represents optionally substituted pyridinyl. In another aspect of that embodiment, $R^1$ represents optionally substituted pyrimidinyl.

In an eighth embodiment, $R^1$ represents optionally substituted heteroaryl-aryl-. In one aspect of that embodiment, $R^1$ represents optionally substituted imidazolylphenyl-.

In a ninth embodiment, $R^1$ represents optionally substituted ($C_{3-7}$)cycloalkyl-heteroaryl-. In a first aspect of that embodiment, $R^1$ represents optionally substituted cyclohexylpyrazolyl-. In a second aspect of that embodiment, $R^1$ represents optionally substituted cyclopropylpyridinyl-. In a third aspect of that embodiment, $R^1$ represents optionally substituted cyclobutylpyridinyl-. In a fourth aspect of that embodiment, $R^1$ represents optionally substituted cyclohexylpyridinyl-. In a fifth aspect of that embodiment, $R^1$ represents optionally substituted cyclopropylpyrimidinyl-. In a sixth aspect of that embodiment, $R^1$ represents optionally substituted cyclobutylpyrimidinyl-. In a seventh aspect of that embodiment, $R^1$ represents optionally substituted cyclopentylpyrimidinyl-. In an eighth aspect of that embodiment, $R^1$ represents optionally substituted cyclohexylpyrimidinyl-. In a ninth aspect of that embodiment, $R^1$ represents optionally substituted cyclohexylpyrazinyl-.

In a tenth embodiment, $R^1$ represents optionally substituted ($C_{4-9}$)bicycloalkyl-heteroaryl-.

In an eleventh embodiment, $R^1$ represents optionally substituted ($C_{3-7}$)-heterocycloalkyl-heteroaryl-. In a first aspect of that embodiment, $R^1$ represents substituted azetidinylpyrazolyl-. In a second aspect of that embodiment, $R^1$ represents optionally substituted pyrrolidinylpyridinyl-. In a third aspect of that embodiment, $R^1$ represents optionally substituted tetrahydropyranylpyridinyl-. In a fourth aspect of that embodiment, $R^1$ represents optionally substituted piperidinylpyridinyl-. In a fifth aspect of that embodiment, $R^1$ represents optionally substituted piperazinylpyridinyl-. In a sixth aspect of that embodiment, $R^1$ represents optionally substituted morpholinylpyridinyl-. In a seventh aspect of that embodiment, $R^1$ represents optionally substituted thiomorpholinylpyridinyl-. In an eighth aspect of that embodiment, $R^1$ represents optionally substituted diazepanylpyridinyl-. In a ninth aspect of that embodiment, $R^1$ represents optionally substituted oxetanylpyrimidinyl-. In a tenth aspect of that embodiment, $R^1$ represents optionally substituted azetidinylpyrimidinyl-. In an eleventh aspect of that embodiment, $R^1$ represents optionally substituted tetrahydrofuranylpyrimidinyl-. In a twelfth aspect of that embodiment, $R^1$ represents substituted tetrahydrothienyl-pyrimidinyl-. In a thirteenth aspect of that embodiment, $R^1$ represents optionally substituted pyrrolidinylpyrimidinyl-. In a fourteenth aspect of that embodiment, $R^1$ represents optionally substituted tetrahydropyranylpyrimidinyl-. In a fifteenth aspect of that embodiment, $R^1$ represents optionally substituted dioxanylpyrimidinyl-. In a sixteenth aspect of that embodiment, $R^1$ represents optionally substituted piperidinylpyrimidinyl-. In a seventeenth aspect of that embodiment, $R^1$ represents optionally substituted piperazinylpyrimidinyl-. In an eighteenth aspect of that embodiment, $R^1$ represents optionally substituted morpholinylpyrimidinyl-. In a nineteenth aspect of that embodiment, $R^1$ represents optionally substituted thiomorpholinylpyrimidinyl-. In a twentieth aspect of that embodiment, $R^1$ represents optionally substituted azepanylpyrimidinyl-. In a twenty-first aspect of that embodiment, $R^1$ represents optionally substituted oxazepanylpyrimidinyl-. In a twenty-second aspect of that embodiment, $R^1$ represents optionally substituted diazepanylpyrimidinyl-. In a twenty-third aspect of that embodiment, $R^1$ represents optionally substituted thiadiazepanylpyrimidinyl-. In a twenty-fourth aspect of that embodiment, $R^1$ represents optionally substituted oxetanylpyrazinyl-. In a twenty-fifth aspect of that embodiment, $R^1$ represents optionally substituted piperidinylpyrazinyl-.

In a twelfth embodiment, $R^1$ represents optionally substituted $(C_{4-9})$-heterobicycloalkyl-heteroaryl-. In a first aspect of that embodiment, $R^1$ represents optionally substituted (2-oxa-5-azabicyclo[2.2.1]heptanyl)pyrimidinyl-. In a second aspect of that embodiment, $R^1$ represents optionally substituted (3-oxa-8-azabicyclo-[3.2.1]octanyl)pyrimidinyl-. In a third aspect of that embodiment, $R^1$ represents optionally substituted (3,6-diazabicyclo[3.2.2]nonanyl)pyrimidinyl-. In a fourth aspect of that embodiment, $R^1$ represents optionally substituted (3,7-dioxa-9-azabicyclo[3.3.1]-nonanyl)pyrimidinyl-.

In a thirteenth embodiment, $R^1$ represents optionally substituted $(C_{4-9})$spiro-heterocycloalkyl-heteroaryl-.

Appositely, $R^1$ represents fluoro, chloro or cyano; or $R^1$ represents phenyl, azetidinyl, dihydropyridinyl, dihydropyrimidinyl, pyrazolyl, pyridinyl, pyrimidinyl, imidazolylphenyl, cyclopropylpyridinyl, cyclobutylpyridinyl, cyclobutylpyrimidinyl, cyclohexylpyrimidinyl, azetidinylpyrazolyl, oxetanylpyridinyl, azetidinylpyridinyl, pyrrolidinylpyridinyl, piperazinylpyridinyl, oxetanylpyrimidinyl, azetidinylpyrimidinyl, tetrahydrofuranylpyrimidinyl, tetrahydrothienylpyrimidinyl, pyrrolidinylpyrimidinyl, tetrahydropyranylpyrimidinyl, dioxanylpyrimidinyl, piperazinylpyrimidinyl, morpholinylpyrimidinyl, thiomorpholinylpyrimidinyl, diazepanylpyrimidinyl, (2-oxa-5-azabicyclo-[2.2.1]heptanyl)pyrimidinyl, (3-oxa-8-azabicyclo[3.2.1]octanyl)pyrimidinyl, (3,6-diazabicyclo[3.2.2]nonanyl)pyrimidinyl or (3,7-dioxa-9-azabicyclo[3.3.1]nonanyl)-pyrimidinyl, any of which groups may be optionally substituted by one or more substituents.

More typically, $R^1$ represents fluoro or chloro; or $R^1$ represents pyrimidinyl, cyclobutylpyrimidinyl, cyclopentylpyrimidinyl, cyclohexylpyrimidinyl, oxetanylpyrimidinyl, tetrahydrofuranylpyrimidinyl, pyrrolidinylpyrimidinyl, tetrahydropyranylpyrimidinyl, dioxanylpyrimidinyl or morpholinylpyrimidinyl, any of which groups may be optionally substituted by one or more substituents. Additionally, $R^1$ may represent cyclobutylpyridinyl, which group may be optionally substituted by one or more substituents.

Advantageously, $R^1$ represents pyrimidinyl, cyclobutylpyridinyl or cyclobutylpyrimidinyl, any of which groups may be optionally substituted by one or more substituents.

Illustratively, $R^1$ represents pyrimidinyl or cyclobutylpyrimidinyl, either of which groups may be optionally substituted by one or more substituents.

Typical examples of optional substituents on $R^1$ include one, two or three substituents independently selected from halogen, halo$(C_{1-6})$alkyl, cyano, cyano$(C_{1-6})$alkyl, nitro$(C_{1-6})$alkyl, $C_{1-6}$ alkyl, phosphate$(C_{1-6})$alkyl, $(C_{1-6})$alkylphosphate$(C_{1-6})$alkyl, phosphate$(C_{1-6})$alkoxy$(C_{1-6})$alkyl, sulphate$(C_{1-6})$alkyl, difluoromethyl, trifluoromethyl, trifluoroethyl, $C_{2-6}$ alkenyl, hydroxy, hydroxy$(C_{1-6})$alkyl, $C_{1-6}$ alkoxy, $(C_{1-6})$alkoxy$(C_{1-6})$-alkyl, trifluoroethoxy, carboxy$(C_{3-7})$cycloalkyloxy, $C_{1-6}$ alkylthio, $C_{1-6}$ alkylsulphonyl, $(C_{1-6})$alkylsulphonyl$(C_{1-6})$alkyl, oxo, amino, amino$(C_{1-6})$alkyl, $C_{1-6}$ alkylamino, di$(C_{1-6})$-alkylamino, di$(C_{1-6})$alkylamino$(C_{1-6})$alkyl, $(C_{1-6})$alkoxy$(C_{1-6})$alkylamino, N—[$(C_{1-6})$alkyl]-N-[hydroxy$(C_{1-6})$alkyl]amino, $(C_{2-6})$alkylcarbonylamino$(C_{1-6})$alkyl, $(C_{2-6})$alkoxycarbonyl-amino$(C_{1-6})$alkyl, $C_{1-6}$ alkylsulphinylamino, $C_{1-6}$ alkylsulphonylamino, N—[$(C_{1-6})$alkyl]-N—[$(C_{1-6})$alkylsulphonyl]amino, bis[$(C_{1-6})$alkylsulphonyl]amino, $(C_{1-6})$alkylsulphonylamino-$(C_{1-6})$alkyl, N—[$(C_{1-6})$alkyl]-N-[carboxy$(C_{1-6})$alkyl]amino, carboxy$(C_{3-7})$cycloalkylamino, carboxy$(C_{3-7})$cycloalkyl$(C_{1-6})$alkylamino, imino, formyl, $C_{2-6}$ alkylcarbonyl, $(C_{2-6})$alkyl-carbonyloxy$(C_{1-6})$alkyl, carboxy, carboxy$(C_{1-6})$alkyl, $C_{2-6}$ alkoxycarbonyl, $C_{2-6}$ alkoxy-carbonyl$(C_{1-6})$alkyl, morpholinyl$(C_{1-6})$alkoxycarbonyl, $C_{2-6}$ alkoxycarbonylmethylidenyl, aminocarbonyl, aminosulphonyl, $(C_{1-6})$alkylsulphoximinyl and [$(C_{1-6})$alkyl][N—$(C_{1-6})$-alkyl]sulphoximinyl.

Illustrative examples of optional substituents on $R^1$ include one, two or three substituents independently selected from halogen, cyano, $C_{1-6}$ alkyl, difluoromethyl, hydroxy$(C_{1-6})$alkyl, oxo, amino and amino$(C_{1-6})$alkyl.

Selected examples of optional substituents on $R^1$ include one, two or three substituents independently selected from cyano, $C_{1-6}$ alkyl, hydroxy$(C_{1-6})$alkyl and amino.

Particular examples of optional substituents on $R^1$ include one, two or three substituents independently selected from hydroxy$(C_{1-6})$alkyl and amino.

Typical examples of particular substituents on $R^1$ include one, two or three substituents independently selected from fluoro, chloro, fluoromethyl, fluoroisopropyl, cyano, cyanoethyl, cyanoisopropyl, nitromethyl, methyl, ethyl, isopropyl, isopropylmethyl, phosphate-isopropyl, ethylphosphate-isopropyl, phosphate-methoxyisopropyl, sulphate-isopropyl, difluoromethyl, trifluoromethyl, trifluoroethyl, ethenyl, hydroxy, hydroxymethyl, hydroxyisopropyl, hydroxyisobutyl, methoxy, isopropoxy, methoxyisopropyl, trifluoroethoxy, carboxycyclobutyloxy, methylthio, methylsulphonyl, methyl-sulphonylmethyl, methylsulphonylethyl, oxo, amino, aminomethyl, aminoisopropyl, methylamino, dimethylamino, dimethylaminoisopropyl, methoxyethylamino, N-(hydroxyethyl)-N-(methyl)amino, acetylaminomethyl, acetylaminoisopropyl, methoxy-carbonylaminoisopropyl, (tert-butoxycarbonyl)aminoisopropyl, (tert-butyl)sulphinylamino, methylsulphonylamino, (tert-butyl)sulphonylamino, N-methyl-N-(methyl-sulphonyl)amino, bis(methylsulphonyl)amino, methylsulphonylaminoisopropyl, N-(carboxyethyl)-N-(methyl)amino, carboxycyclopentylamino, carboxycyclopropylmethyl-amino, imino, formyl, acetyl, (tert-butyl)carbonyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxycarbonylmethyl, ethoxycarbonylethyl, morpholinylethoxycarbonyl, ethoxycarbonylmethylidenyl, aminocarbonyl, aminosulphonyl, methylsulphoximinyl and (methyl)(N-methyl)sulphoximinyl.

Illustrative examples of particular substituents on $R^1$ include one, two or three substituents independently selected from fluoro, cyano, methyl, difluoromethyl, hydroxyisopropyl, oxo, amino and aminoisopropyl. Additional examples include hydroxymethyl (including —$CD_2OH$).

Selected examples of particular substituents on $R^1$ include one, two or three substituents independently selected from cyano, methyl, hydroxymethyl (including —$CD_2OH$), hydroxyisopropyl and amino.

Suitable examples of particular substituents on $R^1$ include one, two or three substituents independently selected from hydroxyisopropyl and amino.

In a particular embodiment, $R^1$ is substituted by hydroxy ($C_{1-6}$)alkyl. In one aspect of that embodiment, $R^1$ is substituted by hydroxyisopropyl, especially 2-hydroxyprop-2-yl.

Illustrative values of $R^1$ include fluoro, chloro, cyano, (methyl)(methylthio)phenyl, methylsulphonylphenyl, (methyl)(methylsulphonyl)phenyl, methylsulphoximinylphenyl, (hydroxyisopropyl)azetidinyl, methylpyrazolyl, hydroxyisopropylpyridinyl, (hydroxyisopropyl)(methyl)pyridinyl, methoxypyridinyl, oxopyridinyl, (methyl)(oxo)pyridinyl, cyanoisopropylpyrimidinyl, phosphate-isopropylpyrimidinyl, sulphate-isopropylpyrimidinyl, hydroxyisopropylpyrimidinyl, (hydroxyisopropyl)(methyl)-pyrimidinyl, (dimethyl)(hydroxyisopropyl)pyrimidinyl, (difluoromethyl)-(hydroxyisopropyl)pyrimidinyl, (hydroxyisopropyl)(trifluoromethyl)pyrimidinyl, hydroxyisobutylpyrimidinyl, methoxyisopropylpyrimidinyl, oxopyrimidinyl, aminoisopropylpyrimidinyl, (dimethylamino)isopropylpyrimidinyl, acetylaminoisopropyl-pyrimidinyl, (methoxycarbonyl)aminoisopropylpyrimidinyl, (tert-butoxycarbonyl)aminoisopropylpyrimidinyl, (methylsulphonyl)aminoisopropylpyrimidinyl, methyl-sulphoximinylpyridinyl, (dimethyl)imidazolylphenyl, methylsulphonylcyclopropyl-pyridinyl, aminocyclobutylpyridinyl, (tert-butyl)sulphinylaminocyclobutylpyridinyl, (dihydroxy)(methyl)cyclobutylpyrimidinyl, aminocyclobutylpyrimidinyl, (amino)(cyano)cyclobutylpyrimidinyl, (amino)(difluoromethyl)cyclobutylpyrimidinyl, aminocyclopentyl-pyrimidinyl, (difluoro)(hydroxy)cyclohexylpyrimidinyl, (dihydroxy)(methyl)cyclohexylpyrimidinyl, (amino)(difluoro)cyclohexylpyrimidinyl, (methylsulphonyl)azetidinylpyrazolyl, aminooxetanylpyridinyl, (tert-butyl)sulphinylaminooxetanylpyridinyl, (tert-butyl)sulphonylaminooxetanylpyridinyl, pyrrolidinylpyridinyl, (hydroxy)pyrrolidinylpyridinyl, (tert-butoxycarbonyl)(hydroxy)pyrrolidinylpyridinyl, piperazinylpyridinyl, (methylsulphonyl)piperazinylpyridinyl, (hydroxy)oxetanylpyrimidinyl, (amino)oxetanylpyrimidinyl, (difluoro)azetidinylpyrimidinyl, (cyano)(methyl)azetidinylpyrimidinyl, (hydroxy)(methyl)azetidinylpyrimidinyl, (hydroxy)(trifluoromethyl)azetidinylpyrimidinyl, [(hydroxy)(trifluoromethyl)azetidinyl](methyl)pyrimidinyl, (hydroxyisopropyl)(tetrahydrofuranyl)pyrimidinyl, aminotetrahydrofuranylpyrimidinyl, (hydroxy)tetrahydrothienylpyrimidinyl, (hydroxy)(oxo)tetrahydrothienylpyrimidinyl, (hydroxy)(dioxo)tetrahydrothienylpyrimidinyl, pyrrolidinylpyrimidinyl, methylpyrrolidinyl-pyrimidinyl, tetrahydropyranylpyrimidinyl, aminotetrahydropyranylpyrimidinyl, (amino)(dimethyl)dioxanylpyrimidinyl, (hydroxyisopropyl)piperidinylpyrimidinyl, (aminoisopropyl)piperidinylpyrimidinyl, (oxo)piperazinylpyrimidinyl, morpholinylpyrimidinyl, methylmorpholinylpyrimidinyl, aminomorpholinylpyrimidinyl, thiomorpholinylpyrimidinyl, (oxo)thiomorpholinylpyrimidinyl, (dioxo)thiomorpholinylpyrimidinyl, (amino)(dioxo)thiomorpholinylpyrimidinyl, (oxo)diazepanylpyrimidinyl, hydroxyisopropyl-(3-azabicyclo[3.1.0]hexanyl)pyrimidinyl, (2-oxa-5-azabicyclo[2.2.1]-heptanyl)pyrimidinyl, (3-oxa-8-azabicyclo[3.2.1]octanyl)pyrimidinyl, (oxo)(3,6-diazabicyclo[3.2.2]nonanyl)pyrimidinyl and (3,7-dioxa-9-azabicyclo[3.3.1]nonanyl)-pyrimidinyl. Additional values include [(amino)(cyano)(methyl)cyclobutyl](fluoro)pyridinyl and (amino)[hydroxy(dideutero)methyl](methyl)cyclobutylpyrimidinyl.

Typical values of $R^1$ include fluoro, chloro, hydroxyisopropylpyrimidinyl, aminoisopropylpyrimidinyl, aminocyclobutylpyrimidinyl, (amino)(cyano)cyclobutylpyrimidinyl, (amino)(difluoromethyl)cyclobutylpyrimidinyl, aminocyclopentyl-pyrimidinyl, (amino)(difluoro)cyclohexylpyrimidinyl, (amino)oxetanylpyrimidinyl, aminotetrahydrofuranylpyrimidinyl, pyrrolidinylpyrimidinyl, methylpyrrolidinyl-pyrimidinyl, aminotetrahydropyranylpyrimidinyl, (amino)(dimethyl)dioxanylpyrimidinyl, (hydroxyisopropyl)piperidinylpyrimidinyl, (aminoisopropyl)piperidinylpyrimidinyl, morpholinylpyrimidinyl, methylmorpholinylpyrimidinyl, aminomorpholinylpyrimidinyl, (dioxo)thiomorpholinylpyrimidinyl, (amino)(dioxo)thiomorpholinylpyrimidinyl and hydroxyisopropyl-(3-azabicyclo[3.1.0]hexanyl)pyrimidinyl. Additional values include [(amino)(cyano)(methyl)cyclobutyl](fluoro)pyridinyl and (amino)[hydroxy(dideutero)-methyl](methyl)cyclobutylpyrimidinyl.

Apposite values of $R^1$ include hydroxyisopropylpyrimidinyl, [(amino)(cyano)(methyl)cyclobutyl](fluoro)pyridinyl, aminocyclobutylpyrimidinyl and (amino)[hydroxy-(dideutero)methyl](methyl)cyclobutylpyrimidinyl.

Selected values of $R^1$ include hydroxyisopropylpyrimidinyl and aminocyclobutylpyrimidinyl.

In a first embodiment, $R^1$ represents hydroxyisopropylpyrimidinyl, especially 2-(2-hydroxypropan-2-yl)pyrimidin-5-yl.

In a second embodiment, $R^1$ represents [(amino)(cyano)(methyl)cyclobutyl]-(fluoro)pyridinyl, especially 2-(3-amino-1-cyano-3-methylcyclobutyl)-3-fluoropyridin-5-yl.

In a third embodiment, $R^1$ represents aminocyclobutylpyrimidinyl, especially 2-(1-amino cyclobutyl)pyrimidin-5-yl.

In a fourth embodiment, $R^1$ represents (amino)[hydroxy(dideutero)methyl]-(methyl)cyclobutylpyrimidinyl, especially 2-{1-amino-3-[hydroxy(dideutero)methyl]-3-methylcyclobutyl}pyrimidin-5-yl.

Generally, $R^2$ represents hydrogen, halogen, trifluoromethyl, trifluoromethoxy or —$OR^a$; or $R^2$ represents $C_{1-6}$ alkyl or heteroaryl, either of which groups may be optionally substituted by one or more substituents.

Typically, $R^2$ represents hydrogen or halogen; or $R^2$ represents heteroaryl, which group may be optionally substituted by one or more substituents.

Suitably, $R^2$ represents hydrogen or halogen.

In a first embodiment, $R^2$ represents hydrogen. In a second embodiment, $R^2$ represents halogen. In one aspect of that embodiment, $R^2$ represents fluoro. In another aspect of that embodiment, $R^2$ represents chloro. In a third embodiment, $R^2$ represents cyano. In a fourth embodiment, $R^2$ represents nitro. In a fifth embodiment, $R^2$ represents hydroxy. In a sixth embodiment, $R^2$ represents trifluoromethyl. In a seventh embodiment, $R^2$ represents trifluoromethoxy. In an eighth embodiment, $R^2$ represents —$OR^a$.

In a ninth embodiment, $R^2$ represents optionally substituted $C_{1-6}$ alkyl. In a first aspect of that embodiment, $R^2$ represents methyl. In a second aspect of that embodiment, $R^2$ represents ethyl. In a tenth embodiment, $R^2$ represents optionally substituted heteroaryl. In a first aspect of that embodiment, $R^2$ represents optionally substituted pyrimidinyl.

Typical examples of optional substituents on $R^2$ include one, two or three substituents independently selected from hydroxy($C_{1-6}$)alkyl and $C_{2-6}$ alkoxycarbonyl.

Typical examples of particular substituents on $R^2$ include one, two or three substituents independently selected from hydroxyisopropyl and ethoxycarbonyl.

Typical values of $R^2$ include hydrogen, fluoro, chloro, trifluoromethyl, trifluoromethoxy, —$OR^a$, methyl, ethoxycarbonylethyl and hydroxyisopropylpyrimidinyl.

Illustrative values of $R^2$ include hydrogen and fluoro.

Typically, $R^3$ represents hydrogen, halogen or $C_{1-6}$ alkyl.

In a first embodiment, $R^3$ represents hydrogen. In a second embodiment, $R^3$ represents halogen. In one aspect of that embodiment, $R^3$ represents fluoro. In a third embodiment, $R^3$ represents optionally substituted $C_{1-6}$ alkyl. In one aspect of that embodiment, $R^3$ represents methyl. In another aspect of that embodiment, $R^3$ represents ethyl.

Typically, $R^4$ represents hydrogen, halogen or $C_{1-6}$ alkyl.

In a first embodiment, $R^4$ represents hydrogen. In a second embodiment, $R^4$ represents halogen. In one aspect of that embodiment, $R^4$ represents fluoro. In a third embodiment, $R^4$ represents optionally substituted $C_{1-6}$ alkyl. In one aspect of that embodiment, $R^4$ represents methyl. In another aspect of that embodiment, $R^4$ represents ethyl.

Generally, $R^5$ represents halogen, cyano, difluoromethoxy, trifluoromethoxy, —$OR^a$ or $C_{1-6}$ alkylsulphonyl; or $R^5$ represents $C_{1-6}$ alkyl, which group may be optionally substituted by one or more substituents.

Typically, $R^5$ represents difluoromethoxy or —$OR^a$.

In a first embodiment, $R^5$ represents hydrogen. In a second embodiment, $R^5$ represents halogen. In one aspect of that embodiment, $R^5$ represents fluoro. In another aspect of that embodiment, $R^5$ represents chloro. In a third embodiment, $R^5$ represents hydroxy. In a fourth embodiment, $R^5$ represents cyano. In a fifth embodiment, $R^5$ represents trifluoromethyl. In a sixth embodiment, $R^5$ represents difluoromethoxy. In a seventh embodiment, $R^5$ represents trifluoromethoxy. In an eighth embodiment, $R^5$ represents —$OR^a$. In one aspect of that embodiment, $R^5$ represents methoxy. In a ninth embodiment, $R^5$ represents $C_{1-6}$ alkylsulphonyl. In one aspect of that embodiment, $R^5$ represents methylsulphonyl. In a tenth embodiment, $R^5$ represents optionally substituted $C_{1-6}$ alkyl. In one aspect of that embodiment, $R^5$ represents methyl. In another aspect of that embodiment, $R^5$ represents ethyl.

Generally, $R^6$ represents hydrogen, halogen or trifluoromethyl.

In a first embodiment, $R^6$ represents hydrogen. In a second embodiment, $R^6$ represents halogen. In one aspect of that embodiment, $R^6$ represents fluoro. In another aspect of that embodiment, $R^6$ represents chloro. In a third embodiment, $R^6$ represents trifluoromethyl. In a fourth embodiment, $R^6$ represents $C_{1-6}$ alkyl. In one aspect of that embodiment, $R^6$ represents methyl. In another aspect of that embodiment, $R^6$ represents ethyl. In a fifth embodiment, $R^6$ represents $C_{1-6}$ alkoxy. In one aspect of that embodiment, $R^6$ represents methoxy.

Generally, $R^7$ represents hydrogen or trifluoromethyl.

In a first embodiment, $R^7$ represents hydrogen. In a second embodiment, $R^7$ represents halogen. In one aspect of that embodiment, $R^7$ represents fluoro. In another aspect of that embodiment, $R^7$ represents chloro. In a third embodiment, $R^7$ represents trifluoromethyl. In a fourth embodiment, $R^7$ represents $C_{1-6}$ alkyl. In one aspect of that embodiment, $R^7$ represents methyl. In another aspect of that embodiment, $R^7$ represents ethyl. In a fifth embodiment, $R^7$ represents $C_{1-6}$ alkoxy. In one aspect of that embodiment, $R^7$ represents methoxy.

Generally, $R^8$ represents hydrogen or trifluoromethyl.

In a first embodiment, $R^8$ represents hydrogen. In a second embodiment, $R^8$ represents halogen. In one aspect of that embodiment, $R^8$ represents fluoro. In another aspect of that embodiment, $R^8$ represents chloro. In a third embodiment, $R^8$ represents trifluoromethyl. In a fourth embodiment, $R^8$ represents $C_{1-6}$ alkyl. In one aspect of that embodiment, $R^8$ represents methyl. In another aspect of that embodiment, $R^8$ represents ethyl. In a fifth embodiment, $R^8$ represents $C_{1-6}$ alkoxy. In one aspect of that embodiment, $R^8$ represents methoxy.

Typically, $R^{12}$ represents hydrogen or methyl.

In a first embodiment, $R^{12}$ represents hydrogen. In a second embodiment, $R^{12}$ represents $C_{1-6}$ alkyl. In one aspect of that embodiment, $R^{12}$ represents methyl. In another aspect of that embodiment, $R^{12}$ represents ethyl.

Typical examples of suitable substituents which may be present on $R^a$, $R^b$, $R^c$, $R^d$ or $R^e$, or on the heterocyclic moiety —$NR^bR^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$)alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di($C_{1-6}$)alkylamino, phenylamino, pyridinylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino, aminocarbonyl, $C_{1-6}$ alkylaminocarbonyl and di($C_{1-6}$)alkylaminocarbonyl.

Typical examples of specific substituents which may be present on $R^a$, $R^b$, $R^c$, $R^d$ or $R^e$, or on the heterocyclic moiety —$NR^bR^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, tert-butoxycarbonylamino, acetylaminomethyl, methylsulphonylamino, aminocarbonyl, methylaminocarbonyl and dimethylaminocarbonyl.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

Selected values of $R^a$ include methyl, ethyl, benzyl and isoindolylpropyl, any of which groups may be optionally substituted by one or more substituents.

Selected examples of suitable substituents on $R^a$ include $C_{1-6}$ alkoxy and oxo. Selected examples of specific substituents on $R^a$ include methoxy and oxo.

In one embodiment, $R^a$ represents optionally substituted $C_{1-6}$ alkyl. In one aspect of that embodiment, $R^a$ ideally represents unsubstituted $C_{1-6}$ alkyl, especially methyl. In another aspect of that embodiment, $R^a$ ideally represents substituted $C_{1-6}$ alkyl, e.g. methoxyethyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl.

In another embodiment, $R^a$ represents optionally substituted aryl($C_{1-6}$)alkyl, ideally unsubstituted aryl($C_{1-6}$)alkyl, especially benzyl. In a further embodiment, $R^a$ represents optionally substituted heteroaryl. In a further embodiment, $R^a$ represents optionally substituted heteroaryl($C_{1-6}$)alkyl, e.g. dioxoisoindolylpropyl.

Specific values of $R^a$ include methyl, methoxyethyl, benzyl and dioxoisoindolylpropyl.

In a particular aspect, $R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents.

Selected values of $R^b$ include hydrogen; or $C_{1-6}$ alkyl, aryl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Representative values of $R^b$ include hydrogen; or methyl, ethyl, n-propyl, benzyl, pyrrolidinyl or morpholinylpropyl, any of which groups may be optionally substituted by one or more substituents.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di($C_{1-6}$)alkylamino and $C_{2-6}$ alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

Specific values of $R^b$ include hydrogen, methyl, methoxyethyl, methylthioethyl, methylsulphinylethyl, methylsulphonylethyl, hydroxyethyl, cyanoethyl, dimethylamino-ethyl, tert-butoxycarbonylaminoethyl, dihydroxypropyl, benzyl, pyrrolidinyl, tert-butoxycarbonylpyrrolidinyl and morpholinylpropyl.

In one embodiment, $R^b$ represents hydrogen. In another embodiment, $R^b$ represents $C_{1-6}$ alkyl, especially methyl.

Selected values of $R^c$ include hydrogen; or $C_{1-6}$ alkyl, $C_{3-7}$ cycloalkyl or $C_{3-7}$ heterocycloalkyl, any of which groups may be optionally substituted by one or more substituents.

In a particular aspect, $R^c$ represents hydrogen, $C_{1-6}$ alkyl or $C_{3-7}$ cycloalkyl. Representative values of $R^c$ include hydrogen; or methyl, cyclobutyl, cyclopentyl, cyclohexyl, tetrahydropyranyl and piperidinyl, any of which groups may be optionally substituted by one or more substituents.

Selected examples of suitable substituents on $R^c$ include $C_{2-6}$ alkylcarbonyl and $C_{2-6}$ alkoxycarbonyl.

Selected examples of specific substituents on $R^c$ include acetyl and tert-butoxycarbonyl.

Specific values of $R^c$ include hydrogen, methyl, cyclobutyl, cyclopentyl, cyclohexyl, tetrahydropyranyl, acetylpiperidinyl and tert-butoxycarbonylpiperidinyl, Suitably, $R^c$ represents hydrogen or $C_{1-6}$ alkyl. In one embodiment, $R^c$ is hydrogen. In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents.

Selected examples of suitable substituents on the heterocyclic moiety —$NR^bR^c$ include $C_{1-6}$ alkyl, $C_{1-6}$ alkylsulphonyl, hydroxy, hydroxy($C_{1-6}$)alkyl, amino($C_{1-6}$)alkyl, cyano, oxo, $C_{2-6}$ alkylcarbonyl, carboxy, $C_{2-6}$ alkoxycarbonyl, amino, $C_{2-6}$ alkylcarbonylamino, $C_{2-6}$ alkylcarbonylamino ($C_{1-6}$)alkyl, $C_{2-6}$ alkoxycarbonylamino, $C_{1-6}$ alkylsulphonylamino and aminocarbonyl.

Selected examples of specific substituents on the heterocyclic moiety —$NR^bR^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxycarbonylamino, methylsulphonylamino and aminocarbonyl.

Specific values of the moiety —$NR^bR^c$ include azetidin-1-yl, hydroxyazetidin-1-yl, hydroxymethylazetidin-1-yl, (hydroxy)(hydroxymethyl)azetidin-1-yl, aminomethyl-azetidin-1-yl, cyanoazetidin-1-yl, carboxyazetidin-1-yl, aminoazetidin-1-yl, aminocarbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxo-oxazolidin-3-yl, hydroxyisoxazolidin-2-yl, thiazolidin-3-yl, oxothiazolidin-3-yl, dioxo-isothiazolidin-2-yl, piperidin-1-yl, hydroxypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl and oxohomopiperazin-1-yl.

Suitably, $R^d$ represents hydrogen; or $C_{1-6}$ alkyl, aryl or heteroaryl, any of which groups may be optionally substituted by one or more substituents.

Selected examples of suitable values for $R^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$ alkylcarbonyloxy and di($C_{1-6}$)alkylamino.

Selected examples of particular substituents on $R^d$ include fluoro, methyl, methoxy, oxo, acetoxy and dimethylamino.

In one embodiment, $R^d$ represents hydrogen. In another embodiment, $R^d$ represents optionally substituted $C_{1-6}$ alkyl. In one aspect of that embodiment, $R^d$ ideally represents unsubstituted $C_{1-6}$ alkyl, e.g. methyl, ethyl, isopropyl, 2-methylpropyl or tert-butyl, especially methyl. In another aspect of that embodiment, $R^d$ ideally represents substituted $C_{1-6}$ alkyl, e.g. substituted methyl or substituted ethyl, including acetoxymethyl, dimethylaminomethyl and trifluoroethyl. In another embodiment, $R^d$ represents optionally substituted aryl. In one aspect of that embodiment, $R^d$ represents unsubstituted aryl, especially phenyl. In another aspect of that embodiment, $R^d$ represents monosubstituted aryl, especially methylphenyl. In a further aspect of that embodiment, $R^d$ represents disubstituted aryl, e.g. dimethoxyphenyl. In a further embodiment, $R^d$ represents optionally substituted heteroaryl, e.g. thienyl, chlorothienyl, methylthienyl, methylimidazolyl or thiazolyl. In another embodiment, $R^d$ represents optionally substituted $C_{3-7}$ cycloalkyl, e.g. cyclopropyl or cyclobutyl. In a further embodiment, $R^d$ represents optionally substituted $C_{3-7}$ heterocycloalkyl, e.g. thiazolidinyl or oxothiazolidinyl.

Selected examples of specific values for $R^d$ include hydrogen, methyl, acetoxymethyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Suitably, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In one embodiment, $R^e$ represents optionally substituted $C_{1-6}$ alkyl, ideally unsubstituted $C_{1-6}$ alkyl, e.g. methyl or propyl, especially methyl. In another embodiment, $R^e$ represents optionally substituted aryl. In one aspect of that embodiment, $R^e$ represents unsubstituted aryl, especially phenyl. In another aspect of that embodiment, $R^e$ represents monosubstituted aryl, especially methylphenyl. In a further embodiment, $R^e$ represents optionally substituted heteroaryl.

Selected values of $R^e$ include methyl, propyl and methylphenyl.

Typical examples of optional substituents on $R^f$ include one, two or three substituents independently selected from hydroxy and carboxy.

Generally, $R^f$ represents hydrogen or $C_{1-6}$ alkyl.

In a first embodiment, $R^f$ represents hydrogen. In a second embodiment, $R^f$ represents $C_{1-6}$ alkyl. In a first aspect of that embodiment, $R^f$ represents methyl. In a first variant of that aspect, $R^f$ represents —$CH_3$. In a second variant of that aspect, $R^f$ represents —$CD_3$. In a second aspect of that embodiment, $R^f$ represents ethyl. In a third aspect of that embodiment, $R^f$ represents isopropyl.

Typical values of $R^f$ include hydrogen, methyl (—$CH_3$ or —$CD_3$), ethyl and isopropyl.

Selected values of $R^f$ include hydrogen and methyl (—$CH_3$ or —$CD_3$).

Generally, $R^g$ represents hydrogen, —$SO_2R^a$, —$COR^d$ or —$CO_2R^d$; or $R^g$ represents $C_{1-6}$ alkyl or heteroaryl, either of which groups may be optionally substituted by one or more substituents.

Typical examples of optional substituents on $R^g$ include one, two or three substituents independently selected from halogen, trifluoromethyl, $C_{1-6}$ alkyl, $C_{4-9}$ heterobicycloalkyl, hydroxy, $C_{1-6}$ alkoxy, $C_{1-6}$ alkylsulphonyl, carboxy and $C_{2-6}$ alkoxycarbonyl.

Typical examples of optional substituents on $R^g$ include one, two or three substituents independently selected from fluoro, chloro, trifluoromethyl, methyl, 3,7-dioxa-9-azabicyclo[3.3.1]nonan-9-yl, hydroxy, methoxy, methylsulphonyl, carboxy and ethoxycarbonyl.

Typically, $R^g$ represents hydrogen or $C_{1-6}$ alkyl.

In a first embodiment, $R^g$ represents hydrogen. In a second embodiment, $R^g$ represents —$SO_2R^a$. In a third embodiment, $R^g$ represents —$COR^d$. In a fourth embodiment, $R^g$ represents —$CO_2R^d$. In a fifth embodiment, $R^g$ represents optionally substituted $C_{1-6}$ alkyl. In a first aspect of that embodiment, $R^g$ represents optionally substituted methyl. In a second aspect of that embodiment, $R^g$ represents optionally substituted ethyl. In a third aspect of that embodiment, $R^g$ represents optionally substituted isopropyl. In a sixth embodiment, $R^g$ represents optionally substituted $C_{3-7}$ cycloalkyl. In a seventh embodiment, $R^g$ represents optionally substituted $C_{3-7}$ heterocycloalkyl. In an eighth embodiment, $R^g$ represents optionally substituted heteroaryl. In one aspect of that embodiment, $R^g$ represents optionally substituted pyrimidinyl.

Illustrative values of $R^g$ include hydrogen and methyl.

One sub-group of the compounds of formula (IB) above is represented by the compounds of formula (IIA) and N-oxides thereof, and pharmaceutically acceptable salts thereof:

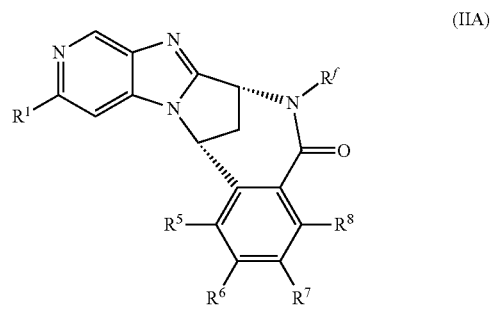

(IIA)

wherein $R^1$, $R^5$, $R^6$, $R^7$, $R^8$ and $R^f$ are as defined above.

A first subset of the compounds of formula (IIA) above is represented by the compounds of formula (IIA-1) and N-oxides thereof, and pharmaceutically acceptable salts thereof:

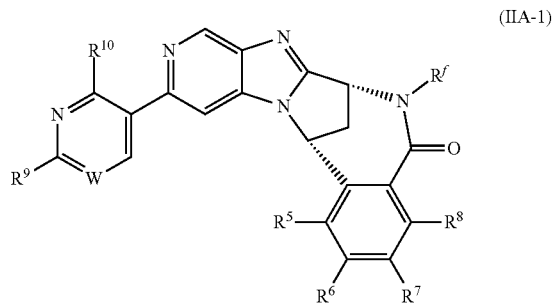

(IIA-1)

wherein
W represents N, CH or CF;
$R^9$ represents hydroxy($C_{1-6}$)alkyl or amino($C_{1-6}$)alkyl;
$R^{10}$ represents hydrogen or $C_{1-6}$ alkyl; and
$R^5$, $R^6$, $R^7$, $R^8$ and $R^f$ are as defined above.

Typically, W represents N or CF.

In a first embodiment, W represents N. In a second embodiment, W represents CH. In a third embodiment, W represents CF.

Typically, $R^9$ represents hydroxyisopropyl or aminoisopropyl.

Typical values of $R^9$ include 2-hydroxyprop-2-yl and 2-aminoprop-2-yl.

In one embodiment, $R^9$ represents hydroxy($C_{1-6}$)alkyl. In a particular aspect of that embodiment, $R^9$ represents hydroxyisopropyl, especially 2-hydroxyprop-2-yl.

In another embodiment, $R^9$ represents amino($C_{1-6}$)alkyl. In a particular aspect of that embodiment, $R^9$ represents aminoisopropyl, especially 2-aminoprop-2-yl.

Typically, $R^{10}$ represents hydrogen or methyl.

In one embodiment, $R^{10}$ represents hydrogen. In another embodiment, $R^{10}$ represents $C_{1-6}$ alkyl. In one aspect of that embodiment, $R^{10}$ represents methyl.

A second subset of the compounds of formula (IIA) above is represented by the compounds of formula (IIA-2) and N-oxides thereof, and pharmaceutically acceptable salts thereof:

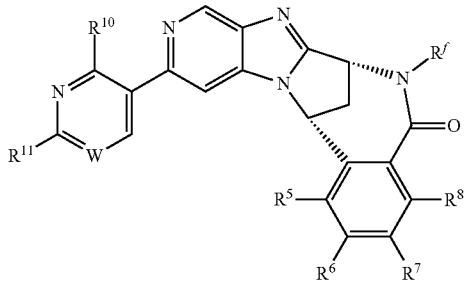

(IIA-2)

wherein $R^{11}$ represents a group of formula (a), (b), (c), (d), (e), (f) or (g):

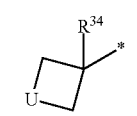 (a)

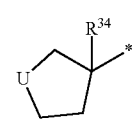 (b)

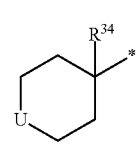 (c)

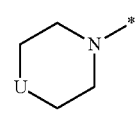 (d)

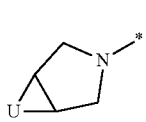 (e)

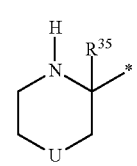 (f)

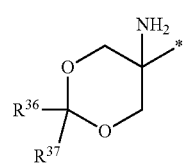 (g)

in which the asterisk (*) represents the site of attachment to the remainder of the molecule;

U represents O, S, S(O), S(O)$_2$, S(O)(NR$^b$), N(R$^{31}$) or C(R$^{32}$)(R$^{33}$);

$R^{31}$ represents hydrogen, cyano($C_{1-6}$)alkyl, $C_{1-6}$ alkyl, trifluoromethyl, trifluoroethyl, $C_{1-6}$ alkylsulphonyl, ($C_{1-6}$) alkylsulphonyl($C_{1-6}$)alkyl, formyl, $C_{2-6}$ alkylcarbonyl, carboxy, carboxy($C_{1-6}$)alkyl, $C_{2-6}$ alkoxycarbonyl, $C_{2-6}$ alkoxycarbonyl($C_{1-6}$)alkyl, tetrazolyl($C_{1-6}$)alkyl, aminocarbonyl, $C_{1-6}$ alkylaminocarbonyl, di($C_{1-6}$)alkylaminocarbonyl, aminosulphonyl, $C_{1-6}$ alkylaminosulphonyl or di($C_{1-6}$)alkylaminosulphonyl;

$R^{32}$ represents hydrogen, halogen, cyano, $C_{1-6}$ alkyl, hydroxy, hydroxy($C_{1-6}$)alkyl, $C_{1-6}$ alkylsulphonyl, formyl, carboxy, carboxy($C_{1-6}$)alkyl, $C_{2-6}$ alkoxycarbonyl, $C_{2-6}$ alkoxycarbonyl($C_{1-6}$)alkyl, aminosulphonyl, ($C_{1-6}$)alkylsulphoximinyl, [($C_{1-6}$)alkyl][N—($C_{1-6}$)alkyl]sulphoximinyl, ($C_{1-6}$)alkylsulphonylaminocarbonyl, ($C_{2-6}$)alkylcarbonylamino-sulphonyl, ($C_{1-6}$)alkoxyaminocarbonyl, tetrazolyl or hydroxyoxadiazolyl;

$R^{33}$ represents hydrogen, halogen, $C_{1-6}$ alkyl, difluoromethyl, trifluoromethyl, hydroxy, hydroxy($C_{1-6}$)alkyl, $C_{1-6}$ alkoxy, amino or carboxy;

$R^{34}$ represents hydrogen, halogen, halo($C_{1-6}$)alkyl, cyano, hydroxy, $C_{1-6}$ alkoxy, $C_{1-6}$ alkylthio, $C_{1-6}$ alkylsulphinyl, $C_{1-6}$ alkylsulphonyl, amino, $C_{1-6}$ alkylamino, di($C_{1-6}$)-alkylamino, ($C_{2-6}$)alkylcarbonylamino, ($C_{2-6}$)alkylcarbonylamino($C_{1-6}$)alkyl, ($C_{1-6}$)alkylsulphonylamino or ($C_{1-6}$) alkylsulphonylamino($C_{1-6}$)alkyl;

$R^{35}$ represents hydrogen or $C_{1-6}$ alkyl;

$R^{36}$ and $R^{37}$ independently represent $C_{1-6}$ alkyl; or $R^{36}$ and $R^{37}$, when taken together with the carbon atom to which they are both attached, represent $C_{3-7}$ cycloalkyl; and W, $R^5$, $R^6$, $R^7$, $R^8$, $R^{10}$, $R^b$ and $R^f$ are as defined above.

Generally, U represents O, S(O)$_2$, N(R$^{31}$) or C(R$^{32}$)(R$^{33}$).

Typically, U represents O, N(R$^{31}$) or C(R$^{32}$)(R$^{33}$).

In a first embodiment, U represents O. In a second embodiment, U represents S. In a third embodiment, U represents S(O). In a fourth embodiment, U represents S(O)$_2$. In a fifth embodiment, U represents S(O)(NR$^b$). In a sixth embodiment, U represents N(R$^{31}$). In a seventh embodiment, U represents C(R$^{32}$)(R$^{33}$).

Typical values of $R^{31}$ include hydrogen, cyanoethyl, methyl, ethyl, isopropyl, trifluoromethyl, trifluoroethyl, methylsulphonyl, methylsulphonylethyl, formyl, acetyl, carboxy, carboxymethyl, carboxyethyl, methoxycarbonyl, ethoxycarbonyl, tert-butoxycarbonyl, ethoxycarbonylmethyl, ethoxycarbonylethyl, tetrazolylmethyl, aminocarbonyl, methylaminocarbonyl, dimethylaminocarbonyl, aminosulphonyl, methylaminosulphonyl and dimethylaminosulphonyl.

Suitably, $R^{31}$ represents hydrogen or $C_{1-6}$ alkyl.

Suitable values of $R^{31}$ include hydrogen and methyl.

In a first embodiment, $R^{31}$ represents hydrogen. In a second embodiment, $R^{31}$ represents $C_{1-6}$ alkyl, especially methyl.

Typically, $R^{32}$ represents hydrogen, halogen, cyano, hydroxy, hydroxy($C_{1-6}$)alkyl, $C_{1-6}$ alkylsulphonyl, formyl, carboxy, carboxy($C_{1-6}$)alkyl, $C_{2-6}$ alkoxycarbonyl, $C_{2-6}$ alkoxycarbonyl($C_{1-6}$)alkyl, aminosulphonyl, ($C_{1-6}$)alkylsulphoximinyl, [($C_{1-6}$)alkyl][N—($C_{1-6}$)alkyl]sulphoximinyl, ($C_{1-6}$)alkylsulphonylaminocarbonyl, ($C_{2-6}$)alkylcarbonylamino-sulphonyl, ($C_{1-6}$)alkoxyaminocarbonyl, tetrazolyl or hydroxyoxadiazolyl.

Typical values of $R^{32}$ include hydrogen, fluoro, cyano, hydroxy, hydroxymethyl, methylsulphonyl, formyl, carboxy, carboxymethyl, carboxyethyl, methoxycarbonyl, ethoxycarbonyl, tert-butoxycarbonyl, methoxycarbonylmethyl, methoxycarbonylethyl, ethoxycarbonylmethyl, ethoxycarbonylethyl, aminosulphonyl, methylsulphoximinyl, (methyl)(N-methyl)sulphoximinyl, methylsulphonylaminocarbonyl, acetylaminosulphonyl, methoxyaminocarbonyl, tetrazolyl and hydroxyoxadiazolyl. Additional values include methyl.

Suitably, $R^{32}$ represents hydrogen, halogen or cyano.

Suitable values of $R^{32}$ include hydrogen, fluoro and cyano.

Appositely, $R^{32}$ represents hydrogen, $C_{1-6}$ alkyl or hydroxy($C_{1-6}$)alkyl.

Apposite values of $R^{32}$ include hydrogen, methyl and hydroxymethyl (including —$CD_2OH$).

In a first embodiment, $R^{32}$ represents hydrogen. In a second embodiment, $R^{32}$ represents halogen, especially fluoro. In a third embodiment, $R^{32}$ represents cyano. In a fourth embodiment, $R^{32}$ represents $C_{1-6}$ alkyl, especially methyl. In a fifth embodiment, $R^{32}$ represents hydroxy($C_{1-6}$)alkyl, especially hydroxymethyl (including —$CD_2OH$).

Typically, $R^{33}$ represents hydrogen, halogen, $C_{1-6}$ alkyl, difluoromethyl, trifluoromethyl, hydroxy($C_{1-6}$)alkyl or amino.

Generally, $R^{33}$ represents hydrogen, halogen, $C_{1-6}$ alkyl, difluoromethyl or trifluoromethyl.

Typical values of $R^{33}$ include hydrogen, fluoro, methyl, ethyl, isopropyl, difluoromethyl, trifluoromethyl, hydroxy, hydroxymethyl, methoxy, amino and carboxy.

Suitably, $R^{33}$ represents hydrogen, halogen or difluoromethyl.

Suitable values of $R^{33}$ include hydrogen, fluoro and difluoromethyl.

Appositely, $R^{33}$ represents hydrogen, $C_{1-6}$ alkyl, hydroxy ($C_{1-6}$)alkyl or amino.

Apposite values of $R^{33}$ include hydrogen, methyl, hydroxymethyl (including —$CD_2OH$) and amino.

In a first embodiment, $R^{33}$ represents hydrogen. In a second embodiment, $R^{33}$ represents halogen. In one aspect of that embodiment, $R^{33}$ represents fluoro. In a third embodiment, $R^{33}$ represents $C_{1-6}$ alkyl. In a first aspect of that embodiment, $R^{33}$ represents methyl. In a second aspect of that embodiment, $R^{33}$ represents ethyl. In a third aspect of that embodiment, $R^{33}$ represents isopropyl. In a fourth embodiment, $R^{33}$ represents difluoromethyl. In a fifth embodiment, $R^{33}$ represents trifluoromethyl. In a sixth embodiment, $R^{33}$ represents hydroxy. In a seventh embodiment, $R^{33}$ represents hydroxy($C_{1-6}$)alkyl. In one aspect of that embodiment, $R^{33}$ represents hydroxymethyl (including —$CD_2OH$). In an eighth embodiment, $R^{33}$ represents $C_{1-6}$ alkoxy. In one aspect of that embodiment, $R^{33}$ represents methoxy. In a ninth embodiment, $R^{33}$ represents amino. In a tenth embodiment, $R^{33}$ represents carboxy.

Typically, $R^{34}$ represents hydrogen, halogen, halo($C_{1-6}$) alkyl, hydroxy, $C_{1-6}$ alkoxy, $C_{1-6}$ alkylthio, $C_{1-6}$ alkylsulphinyl, $C_{1-6}$ alkylsulphonyl, amino, $C_{1-6}$ alkylamino, di($C_{1-6}$)- alkylamino, ($C_{2-6}$)alkylcarbonylamino, ($C_{2-6}$) alkylcarbonylamino($C_{1-6}$)alkyl, ($C_{1-6}$)alkylsulphonylamino or ($C_{1-6}$)alkylsulphonylamino($C_{1-6}$)alkyl.

In a first embodiment, $R^{34}$ represents hydrogen. In a second embodiment, $R^{34}$ represents halogen. In one aspect of that embodiment, $R^{34}$ represents fluoro. In a third embodiment, $R^{34}$ represents halo($C_{1-6}$)alkyl. In one aspect of that embodiment, $R^{34}$ represents fluoromethyl. In a fourth embodiment, $R^{34}$ represents cyano. In a fifth embodiment, $R^{34}$ represents hydroxy. In a sixth embodiment, $R^{34}$ represents $C_{1-6}$ alkoxy, especially methoxy. In a seventh embodiment, $R^{34}$ represents $C_{1-6}$ alkylthio, especially methylthio. In an eighth embodiment, $R^{34}$ represents $C_{1-6}$ alkylsulphinyl, especially methylsulphinyl. In a ninth embodiment, $R^{34}$ represents $C_{1-6}$ alkylsulphonyl, especially methylsulphonyl. In a tenth embodiment, $R^{34}$ represents amino. In an eleventh embodiment, $R^{34}$ represents $C_{1-6}$ alkylamino, especially methylamino. In a twelfth embodiment, $R^{34}$ represents di($C_{1-6}$)alkylamino, especially dimethylamino. In a thirteenth embodiment, $R^{34}$ represents ($C_{2-6}$)alkylcarbonylamino, especially acetylamino. In a fourteenth embodiment, $R^{34}$ represents ($C_{2-6}$)alkylcarbonylamino($C_{1-6}$)alkyl, especially acetylaminomethyl. In a fifteenth embodiment, $R^{34}$ represents ($C_{1-6}$)alkylsulphonylamino, especially methylsulphonylamino. In a sixteenth embodiment, $R^{34}$ represents ($C_{1-6}$)alkylsulphonylamino($C_{1-6}$)alkyl, especially methylsulphonylaminomethyl.

Illustrative values of $R^{34}$ include hydrogen, cyano and amino.

Suitably, $R^{34}$ represents hydrogen or amino.

Selected values of $R^{34}$ include cyano and amino.

Suitable values of $R^{35}$ include hydrogen and methyl.

In a first embodiment, $R^{35}$ represents hydrogen. In a second embodiment, $R^{35}$ represents $C_{1-6}$ alkyl, especially methyl.

Suitably, $R^{36}$ represents methyl or ethyl, especially methyl.

Suitably, $R^{37}$ represents methyl or ethyl, especially methyl.

Alternatively, $R^{36}$ and $R^{37}$, when taken together with the carbon atom to which they are both attached, may suitably represent cyclopropyl, cyclobutyl, cyclopentyl, cyclohexyl or cycloheptyl.

One sub-group of the compounds of formula (IC) above is represented by the compounds of formula (IIB) and N-oxides thereof, and pharmaceutically acceptable salts thereof:

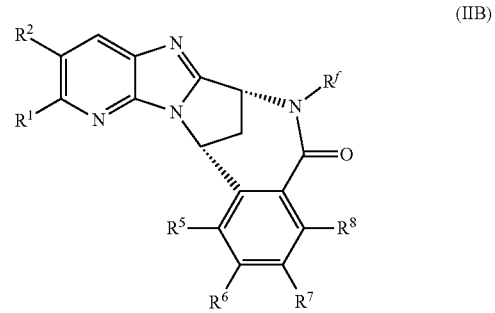

(IIB)

wherein $R^1$, $R^2$, $R^5$, $R^6$, $R^7$, $R^8$ and $R^f$ are as defined above.

A first subset of the compounds of formula (IIB) above is represented by the compounds of formula (IIB-1) and N-oxides thereof, and pharmaceutically acceptable salts thereof:

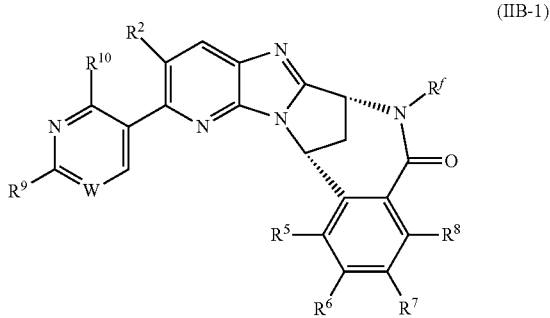

(IIB-1)

wherein W, $R^2$, $R^5$, $R^6$, $R^7$, $R^8$, $R^9$, $R^{10}$ and $R^f$ are as defined above.

A second subset of the compounds of formula (IIB) above is represented by the compounds of formula (IIB-2) and N-oxides thereof, and pharmaceutically acceptable salts thereof:

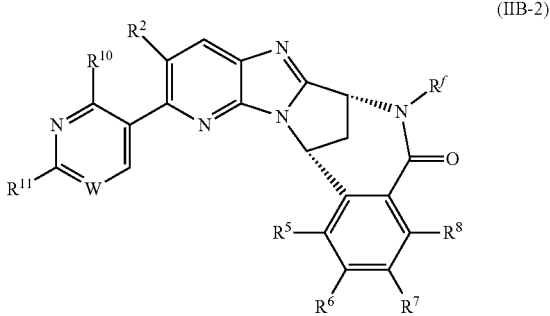

(IIB-2)

wherein W, $R^2$, $R^5$, $R^6$, $R^7$, $R^8$, $R^{10}$, $R^{11}$ and $R^f$ are as defined above.

Specific novel compounds in accordance with the present invention include each of the compounds whose preparation is described in the accompanying Examples, and pharmaceutically acceptable salts thereof.

The compounds in accordance with the present invention are beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, psoriatic arthropathy, vasculitis, inflammatory myopathy (including polymyositis, dermatomyositis and inclusion body myositis), scleroderma, multiple sclerosis, systemic sclerosis, ankylosing spondylitis, rheumatoid arthritis, non-specific inflammatory arthritis, juvenile inflammatory arthritis, juvenile idiopathic arthritis (including oligoarticular and polyarticular forms thereof), anaemia of chronic disease (ACD), Still's disease (juvenile and/or adult onset), Behçet's disease and Sjögren's syndrome. Autoimmune endocrine disorders include thyroiditis. Organ-specific autoimmune disorders include Addison's disease, haemolytic or pernicious anaemia, acute kidney injury (AKI; including cisplatin-induced AKI), diabetic nephropathy (DN), obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis (LN), minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease (COPD), respiratory distress syndrome, sepsis, fever, muscular dystrophy (including Duchenne muscular dystrophy), organ transplant rejection (including kidney allograft rejection), scleritis (including giant cell arteritis scleritis), Takayasu arteritis, hidradenitis suppurativa, pyoderma gangrenosum, sarcoidosis, polymyalgia rheumatic and axial spondyloarthritis.

Neurological and neurodegenerative disorders include Alzheimer's disease, Parkinson's disease, Huntington's disease, ischaemia, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction). Modulators of TNFα function may also be of use in the treatment and/or prevention of myocardial infarction (see J. J. Wu et al., *JAMA*, 2013, 309, 2043-2044).

Metabolic disorders include diabetes (including insulin-dependent diabetes mellitus and juvenile diabetes), dyslipidemia and metabolic syndrome.

Ocular disorders include retinopathy (including diabetic retinopathy, proliferative retinopathy, non-proliferative retinopathy and retinopathy of prematurity), macular oedema (including diabetic macular oedema), age-related macular degeneration (ARMD), vascularisation (including corneal vascularisation and neovascularisation), retinal vein occlusion, and various forms of uveitis (including iritis) and keratitis Oncological disorders, which may be acute or chronic, include proliferative disorders, especially cancer, and cancer-associated complications (including skeletal complications, cachexia and anaemia). Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle. Modulators of TNFα function may also be used to increase the safety of the potent anticancer effect of TNF (see F. V. Hauwermeiren et al., *J. Clin. Invest.*, 2013, 123, 2590-2603).

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule.

The compounds of formula (I) above may be prepared by a process which comprises the intramolecular cyclisation of an intermediate of formula (III):

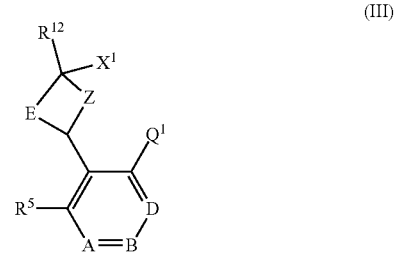

(III)

wherein $X^1$ represents hydroxy, —SH, —CH$_2$OH, —CO$_2$H, —NHR$^f$, —NHR$^g$, —C(O)—NHR$^f$, Y or —CH$_2$—Y;

$Q^1$ represents hydrogen, halogen, hydroxy, amino, —SR', —CO$_2$H, —CH$_2$—Y, —CO—R$^j$ or —CH(OH)CF$_3$;

Y represents a suitable leaving group;

$R^i$ represents hydrogen, methyl, —$CH_2CO_2CH_2CH_3$ or —$(CH_2)_2CO_2CH_2CH(CH_2CH_3)[(CH_2)_3CH_3]$;

$R^j$ represents hydrogen or methyl; and

A, B, D, Z, E, $R^5$, $R^{12}$, $R^f$ and $R^g$ are as defined above.

Suitably, the leaving group Y represents halogen or ($C_{1-6}$)alkylsulphonyloxy.

Appositely, Y represents bromo or methylsulphonyloxy.

The compounds of formula (I) wherein $R^{12}$ represents hydrogen and —X-Q-represents —O— may be prepared by the intramolecular cyclization of an intermediate of formula (III) wherein $R^{12}$ represents hydrogen, $X^1$ represents a leaving group Y, e.g. halogen, preferably bromo, and $Q^1$ represents hydroxy, in the presence of a base, for example sodium hydride or silver carbonate.

Alternatively, the compounds of formula (I) wherein $R^{12}$ represents hydrogen and —X-Q- represents —O— may be prepared by the intramolecular cyclization of an intermediate of formula (III) wherein $R^{12}$ represents hydrogen, $X^1$ represents hydroxy and $Q^1$ represents a leaving group Y, e.g. halogen, preferably bromo, in the presence of a base, e.g. an inorganic base such as cesium carbonate, and copper iodide, at an elevated temperature.

The compounds of formula (I) wherein $R^{12}$ represents hydrogen and —X-Q-represents —O—C(=CH—CN)— may be prepared by the intramolecular cyclization of an intermediate of formula (III) wherein $R^{12}$ represents hydrogen, $X^1$ represents hydroxy and $Q^1$ represents —$CO_2H$, in the presence of cyanomethylenetributylphosphorane.

The reaction is conveniently performed at an elevated temperature in a suitable solvent, e.g. toluene.

The resulting compounds may be transformed into the corresponding compounds of formula (I) wherein $R^{12}$ represents hydrogen and —X-Q- represents —O—C(O)— by treatment with a base, e.g. potassium hydroxide.

Alternatively, the compounds of formula (I) wherein $R^{12}$ represents hydrogen and —X-Q- represents —O—C(O)— may be prepared by the intramolecular cyclization of an intermediate of formula (III) wherein $R^{12}$ represents hydrogen, $X^1$ represents hydroxy and $Q^1$ represents —$CO_2H$, in the presence of an acid, e.g. a mineral acid, in a suitable solvent.

The compounds of formula (I) wherein $R^{12}$ represents hydrogen and —X-Q-represents —C(O)—O— may be prepared by the intramolecular cyclization of an intermediate of formula (III) wherein $R^{12}$ represents hydrogen, $X^1$ represents —$CO_2H$ and $Q^1$ represents hydroxy, in the presence of thionyl chloride, or alternatively by using a suitable coupling reagent according to methods known to the person skilled in the art.

The compounds of formula (I) wherein $R^{12}$ represents hydrogen and —X-Q-represents —S— may be prepared by the intramolecular cyclization of an intermediate of formula (III) wherein $X^1$ represents —SH and $Q^1$ represents halogen, in the presence of a transition metal catalyst, according to a method analogous to that described by Stambuli J. et al. in J. Org. Chem., 2009, 74, 4005-4008.

Alternatively, the compounds of formula (I) wherein $R^{12}$ represents hydrogen and —X-Q- represents —S— may be prepared in a two-step procedure which comprises: (i) reacting an intermediate of formula (III) wherein $R^{12}$ represents hydrogen, $X^1$ represents hydroxy and $Q^1$ represents —$(CH_2)_2CO_2CH_2CH(CH_2CH_3)[(CH_2)_3CH_3]$ with methanesulphonyl chloride in the presence of a base, e.g. N,N-diisopropylethylamine, in a suitable solvent, e.g. tetrahydrofuran, to afford the corresponding compound wherein $X^1$ represents a leaving group Y, in which Y is a mesylate moiety; followed by (ii) intramolecular cyclization of the compound thereby obtained by treatment with sodium ethoxide.

The compounds of formula (I) wherein $R^{12}$ represents hydrogen and —X-Q-represents —$N(R^g)$— may be prepared by the intramolecular cyclization of an intermediate of formula (III) wherein $R^{12}$ represents hydrogen, $X^1$ represents —$NHR^g$ and $Q^1$ represents halogen, in the presence of a transition metal catalyst, according to methods known to the person skilled in the art.

The intramolecular cyclization may be accomplished by utilizing palladium(II) acetate in the presence of (±)-2,2'-bis(diphenylphosphino)-1,1'-binaphthalene (BINAP) or 4,5-bis(diphenylphosphino)-9,9-dimethylxanthene (Xantphos). The reaction may conveniently be effected in the presence of base, e.g. potassium carbonate or cesium carbonate, in a suitable solvent, e.g. toluene or 1,4-dioxane, at an elevated temperature.

Alternatively, the compounds of formula (I) wherein $R^{12}$ represents hydrogen and —X-Q- represents —$N(R^g)$—, in which $R^g$ represents hydrogen, may be prepared by the intramolecular cyclization of an intermediate of formula (III) wherein $R^{12}$ represents hydrogen, $X^1$ is a leaving group Y, e.g. methylsulphonyloxy, and $Q^1$ represents amino. The reaction is conveniently effected in a three-step procedure which comprises: (i) protecting the amino group $Q^1$ with a suitable N-protecting group, e.g. tert-butoxycarbonyl, according to methods known to the person skilled in the art; (ii) intramolecular cyclization by addition of a suitable base, e.g. sodium hydride, in a suitable solvent, e.g. N,N-dimethylformamide; and (iii) removal of the N-protecting group by methods known from the art.

The compounds of formula (I) wherein $R^{12}$ represents hydrogen and —X-Q-represents —$N(R^g)$—, in which $R^g$ represents —$SO_2R^a$, —$COR^d$, —$CO_2R^d$ or optionally substituted heteroaryl, may be prepared by the intramolecular cyclization of an intermediate of formula (III) wherein $R^{12}$ represents hydrogen, $X^1$ represents —$NHR^g$ and $Q^1$ represents halogen. The reaction is conveniently effected by addition of a suitable base, e.g. cesium acetate, and cuprous iodide in a suitable solvent, e.g. dimethyl sulfoxide, at an elevated temperature.

The compounds of formula (I) wherein —X-Q- represents —$N(R^f)$—C(O)— may be prepared by the intramolecular cyclization of an intermediate of formula (III) wherein $X^1$ represents —$NHR^f$ and $Q^1$ is halogen, preferably chloro, in the presence of carbon monoxide and a transition metal catalyst.

The cyclization is generally effected at an elevated temperature under an elevated pressure of carbon monoxide. The reaction is conveniently carried out in a suitable solvent, e.g. 1,4-dioxane, dimethyl sulfoxide or N,N-dimethylacetamide.

Moreover, the cyclization will generally be performed in the presence of a base, e.g. an inorganic base such as sodium carbonate or potassium carbonate, or by activation using molecular sieves.

The transition metal catalyst of use in the above reaction is suitably selected from dichloro[1,3-bis(dicyclohexylphosphino)propane]palladium(II), dichloro[9,9-dimethyl-4,5-bis(diphenylphosphino)xanthene]palladium(II) and 2,2-dichloro-1,1,3,3-tetra-cyclohexyl-1$\lambda^5$,3$\lambda^5$-palladocyclohexane. Alternatively, a solution of palladium (II) acetate and 4,5-bis(diphenylphosphino)-9,9-dimethylxanthene (Xantphos) in a suitable solvent may be used.

In a variant procedure, the reaction may be performed using molybdenum hexacarbonyl as an alternative source of carbon monoxide.

Alternatively, the compounds of formula (I) wherein —X-Q- represents —N($R^f$)—C(O)—, in which $R^f$ represents hydrogen, may be prepared by the intramolecular cyclization of an intermediate of formula (III) wherein $X^1$ represents —NH$R^f$, in which $R^f$ represents hydrogen, and $Q^1$ is —COOH, in the presence of 4-methylmorpholine and (1-cyano-2-ethoxy-2-oxoethylidenaminooxy)dimethyl-amino-morpholino-carbenium hexafluorophosphate (COMU®). The reaction is conveniently effected in a dipolar aprotic solvent such as N,N-dimethylformamide, or an organic nitrile solvent such as acetonitrile.

The intermediates of formula (III) wherein $X^1$ represents —NH$R^f$, in which $R^f$ represents hydrogen, and $Q^1$ is —COOH, may be prepared from the corresponding compound wherein $X^1$ represents —NH$R^f$, in which $R^f$ represents an N-protecting group, and $Q^1$ represents halogen, typically bromo, by a two-step procedure which comprises: (i) treatment with carbon monoxide and a transition metal catalyst; and (ii) removal of the N-protecting group $R^f$.

Step (i) is generally effected at an elevated temperature under an elevated pressure of carbon monoxide. The reaction is conveniently carried out in a suitable solvent, e.g. 1,4-dioxane, dimethyl sulfoxide or N,N-dimethylacetamide.

Moreover, step (i) will generally be performed in the presence of a base, e.g. an inorganic base such as sodium carbonate or potassium carbonate, or by activation using molecular sieves.

The transition metal catalyst of use in the step (i) above is suitably selected from [1,4-bis(diphenylphosphino)butane]palladium(II) chloride, dichloro[1,3-bis(dicyclohexylphosphino)propane]palladium(II), dichloro[9,9-dimethyl-4,5-bis(diphenylphosphino)-xanthene]palladium(II) and 2,2-dichloro-1,1,3,3-tetra-cyclohexyl-1$\lambda^5$,3$\lambda^5$-palladocyclohexane. Alternatively, a solution of palladium (II) acetate and 4,5-bis(diphenyl-phosphino)-9,9-dimethylxanthene (Xantphos) in a suitable solvent may be used.

The N-protecting group $R^f$ of use in the above procedure is suitably tert-butoxycarbonyl (BOC). Removal of the BOC group in step (ii) above will suitably be effected by treatment with an acid, e.g. a mineral acid such as hydrochloric acid, or an organic acid such as trifluoroacetic acid.

The compounds of formula (I) wherein $R^{12}$ represents hydrogen and —X-Q-represents —C(O)—N($R^f$)— may be prepared by the intramolecular cyclization of an intermediate of formula (III) wherein $R^{12}$ represents hydrogen, $X^1$ is —C(O)—NH($R^f$) and $Q^1$ is halogen, preferably bromine, in the presence of a suitable coupling reagent, according to methods known to the person skilled in the art.

Alternatively, the compounds of formula (I) wherein $R^{12}$ represents hydrogen and —X-Q- represents —C(O)—N ($R^f$)—, in which $R^f$ represents hydrogen, may be prepared by the intramolecular cyclization of an intermediate of formula (III) wherein $R^{12}$ represents hydrogen, $X^1$ represents —CO$_2$H and $Q^1$ represents amino. The reaction may conveniently be effected in the presence of a suitable coupling agent, e.g. 1-ethyl-3-(3-dimethylamino-propyl)carbodiimide (EDC), according to methods known to the person skilled in the art.

The compounds of formula (I) wherein $R^{12}$ represents hydrogen and —X-Q-represents —N($R^f$)—SO$_2$— may be prepared by the intramolecular cyclization of an intermediate of formula (III) wherein $R^{12}$ represents hydrogen, $X^1$ represents —NH$R^f$ and $Q^1$ represents —SH, in the presence of hydrogen peroxide and thionyl chloride, according to a method analogous to that described by K. Bahrami, M. M. Khodaei & M. Soheilizad in *J. Org. Chem.*, 2009, 74, 9287-9291.

The reaction is conveniently performed at room temperature in a suitable solvent, e.g. an apolar solvent such as acetonitrile, and in the presence of an organic base, e.g. pyridine.

In an analogous procedure, the compounds of formula (I) wherein $R^{12}$ represents hydrogen and —X-Q- represents —SO$_2$—N($R^f$)—, in which $R^f$ represents hydrogen, may be prepared from an intermediate of formula (III) wherein $R^{12}$ represents hydrogen, $X^1$ represents —SH and $Q^1$ represents amino. The reaction is conveniently effected by first protecting the amino group of $Q^1$ with a suitable N-protecting group according to methods known to the person skilled in the art; which N-protecting group can be removed once the cyclization is accomplished, again by methods known from the art.

The compounds of formula (I) wherein $R^{12}$ represents hydrogen and —X-Q-represents —CH$_2$—CH$_2$— may be prepared by a two-step procedure which comprises: (i) the intramolecular cyclization of an intermediate of formula (III) wherein $R^{12}$ represents hydrogen, $X^1$ represents —CH$_2$—CO$_2$H and $Q^1$ represents hydrogen, typically by applying Friedel Crafts reaction conditions, e.g. by treatment with polyphosphoric acid; and (ii) reduction of the resulting compound, wherein —X-Q- represents —CH$_2$—C(O)—, according to methods known to the person skilled in the art.

The compounds of formula (I) wherein $R^{12}$ represents hydrogen and —X-Q-represents —O—CH$_2$— or —S—CH$_2$— may be prepared by the intramolecular cyclization of an intermediate of formula (III) wherein $R^{12}$ represents hydrogen, $X^1$ represents hydroxy or —SH respectively, and $Q^1$ represents —CH$_2$—Y, in which the leaving group Y is suitably halogen, preferably bromo, in the presence of a suitable base, according to methods known to the person skilled in the art.

The compounds of formula (I) wherein $R^{12}$ represents hydrogen and —X-Q-represents —CH$_2$—O— may be prepared by the intramolecular cyclization of an intermediate of formula (III) wherein $R^{12}$ represents hydrogen, $X^1$ represents —CH$_2$—OH and $Q^1$ represents halogen, preferably bromo. The reaction is conveniently effected in the presence of a suitable transition metal catalyst, e.g. a palladium(II) or copper(II) catalyst, according to methods known to the person skilled in the art.

The compounds of formula (I) wherein $R^{12}$ represents hydrogen and —X-Q-represents —CH$_2$—S— may be prepared by the intramolecular cyclization of an intermediate of formula (III) wherein $R^{12}$ represents hydrogen, $X^1$ is —CH$_2$—Y, in which the leaving group Y is suitably halogen, and $Q^1$ represents —SH, in the presence of suitable base, according to methods known to the person skilled in the art.

The compounds of formula (I) wherein $R^{12}$ represents hydrogen and —X-Q-represents —CH$_2$—N($R^g$)—, in which $R^g$ represents hydrogen, may be prepared by the intramolecular cyclization of an intermediate of formula (III) wherein $R^{12}$ represents hydrogen, $X^1$ is —CH$_2$—Y, in which the leaving group Y is suitably methylsulphonyloxy, and $Q^1$ represents amino. The reaction is conveniently effected in a three-step procedure which comprises: (i) protecting the amino group $Q^1$ with a suitable N-protecting group, e.g. tert-butoxycarbonyl, according to methods known to the person skilled in the art; (ii) intramolecular cyclization by addition of a suitable base, e.g. sodium hydride, in a suitable solvent, e.g. N,N-dimethylformamide; and (iii) removal of the N-protecting group by methods known from the art.

The compounds of formula (I) wherein $R^{12}$ represents hydrogen and —X-Q-represents —N($R^g$)—CH$_2$— or —N($R^g$)—CH(CH$_3$)—, in which $R^g$ represents hydrogen, may be prepared by a two-step procedure involving: (i) the intramolecular cyclization of an intermediate of formula (III) wherein $R^{12}$ represents hydrogen, $X^1$ represents —NH($R^g$), in which $R^g$ represents hydrogen, and $Q^1$ represents formyl or acetyl respectively, by treatment with an acid, e.g. trifluoroacetic acid, in a suitable solvent, e.g. dichloromethane; and (ii) reduction of the compound thereby obtained with an appropriate reducing agent, e.g. polymer-supported cyanoborohydride or borane-dimethylsulphide complex, in a suitable solvent, e.g. tetrahydrofuran, or a mixture of tetrahydrofuran and ethanol.

The compounds of formula (I) wherein $R^{12}$ represents hydrogen and —X-Q-represents —N($R^g$)—CH(CF$_3$)—, in which $R^g$ represents hydrogen, may be prepared by a variant two-step procedure involving: (i) the intramolecular cyclization of an intermediate of formula (III) wherein $R^{12}$ represents hydrogen, $X^1$ represents —NH($R^g$) represents hydrogen, and $Q^1$ represents formyl, by treatment with an acid, e.g. trifluoroacetic acid, in a suitable solvent, e.g. dichloromethane; and (ii) reacting the compound thereby obtained with (trifluoromethyl)trimethyl silane, in the presence of trifluoroacetic acid and potassium hydrogen fluoride, in a suitable solvent, e.g. N,N-dimethylformamide.

The compounds of formula (I) wherein $R^{12}$ represents hydrogen and —X-Q-represents —N=S(O)(CH$_3$)— may be prepared by a two-step procedure involving: (i) the intramolecular cyclization of an intermediate of formula (III) wherein $R^{12}$ represents hydrogen, $X^1$ represents —NH($R^g$), in which $R^g$ represents hydrogen, and $Q^1$ represents —SCH$_3$, by treatment with bromine in dichloromethane; and (ii) oxidation, e.g. with 3-chloroperoxybenzoic acid.

The compounds of formula (I) wherein $R^{12}$ represents hydrogen and —X-Q-represents —O—CH(CF$_3$)— may be prepared by the intramolecular cyclization of an intermediate of formula (III) wherein $R^{12}$ represents hydrogen, $X^1$ represents hydroxy and $Q^1$ represents —CH(OH)CF$_3$. The reaction is conveniently effected using (cyano-methylene)tributylphosphorane, at an elevated temperature in a suitable solvent, e.g. tetrahydrofuran.

The compounds of formula (I) wherein $R^{12}$ represents hydrogen and —X-Q-represents —O—C(=CH$_2$)— may be prepared by the intramolecular cyclization of an intermediate of formula (III) wherein $R^{12}$ represents hydrogen, $X^1$ represents halogen, e.g. bromo, and $Q^1$ represents —CO—$R^j$, in which $R^j$ represents methyl. The reaction is conveniently effected in the presence of a base, e.g. sodium hydride, in a suitable solvent, e.g. tetrahydrofuran, at low temperature.

The intermediates of formula (III) wherein E represents a group of formula (Ea) or (Eb) as defined above, $R^{12}$ represents hydrogen and $X^1$ represents hydroxy, may be prepared by a process which comprises the intramolecular cyclization and desilylation of an intermediate of formula (IV-1) or (IV-2) respectively:

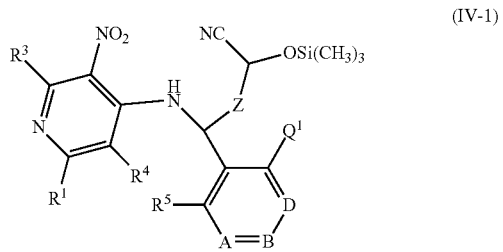

(IV-1)

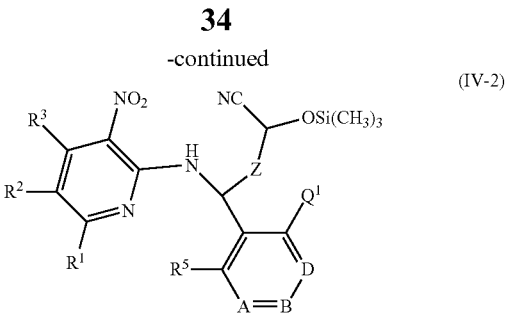

(IV-2)

wherein A, B, D, Z, $R^1$, $R^2$, $R^3$, $R^4$, $R^5$ and $Q^1$ are as defined above.

The reaction is suitably performed in the presence of tin(II) chloride at an elevated temperature in a polar solvent, e.g. ethanol.

The intermediates of formula (IV-1) and (IV-2) as defined above may be prepared by reacting intermediate (V-1) or (V-2) respectively:

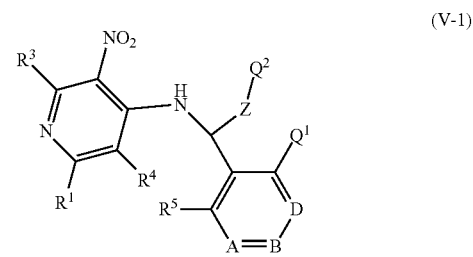

(V-1)

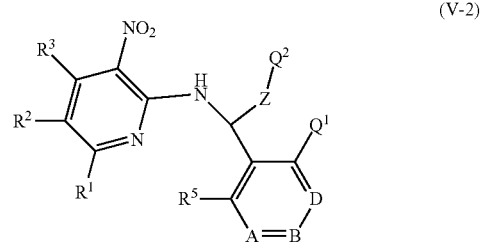

(V-2)

wherein $Q^2$ represents —C(O)—H, and A, B, D, Z, $R^1$, $R^2$, $R^3$, $R^4$, $R^5$ and $Q^1$ are as defined above; with zinc iodide and trimethylsilyl cyanide in the presence of a base, e.g. triethylamine.

Typically, the intermediate of formula (V-1) or (V-2) wherein $Q^2$ represents —C(O)—H may be prepared from the corresponding compound wherein $Q^2$ represents —CO$_2$$R^h$, in which $R^h$ represents C$_{1-6}$ alkyl, e.g. methyl or ethyl, by reduction with a conventional reducing agent, e.g. a metal hydride such as diisobutylaluminium hydride (DIBAL-H); followed, as necessary, by treatment with an oxidising agent, e.g. 1,1,1-tris(acetyloxy)-1,1-dihydro-1,2-benziodoxol-3-(1H)-one (Dess-Martin periodinane).

The intermediates of formula (V-1) or (V-2) wherein $Q^2$ represents —CO$_2$$R^h$ may be obtained by reacting an intermediate of formula (VI-1) or (VI-2) respectively with an intermediate of formula (VII):

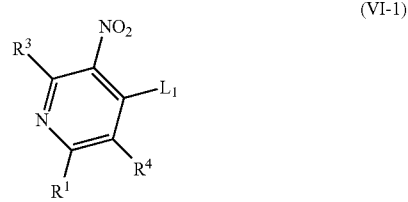

(VI-1)

-continued

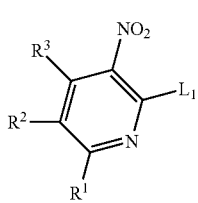
(VI-2)

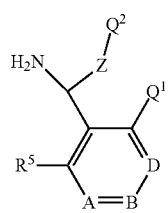
(VII)

wherein A, B, D, Z, $R^1$, $R^2$, $R^3$, $R^4$, $R^5$, $Q^1$ and $Q^2$ are as defined above, and $L^1$ represents a suitable leaving group.

The leaving group $L^1$ is suitably a halogen atom, for example fluoro, chloro or bromo.

The reaction is conveniently performed in the presence of a base, e.g. an organic base such as trimethylamine, or an inorganic base such as potassium carbonate, in a suitable solvent, e.g. an apolar solvent such as dichloromethane, tetrahydrofuran or acetonitrile.

The intermediates of formula (III) wherein E represents a group of formula (Ea) or (Eb) as defined above, $R^{12}$ represents hydrogen and —$X^1$ represents —NH($R^g$), in which $R^g$ represents hydrogen, may be prepared by a process which comprises the reduction, intramolecular cyclization and desulfination of an intermediate of formula (IVa-1) or (IVa-2) respectively:

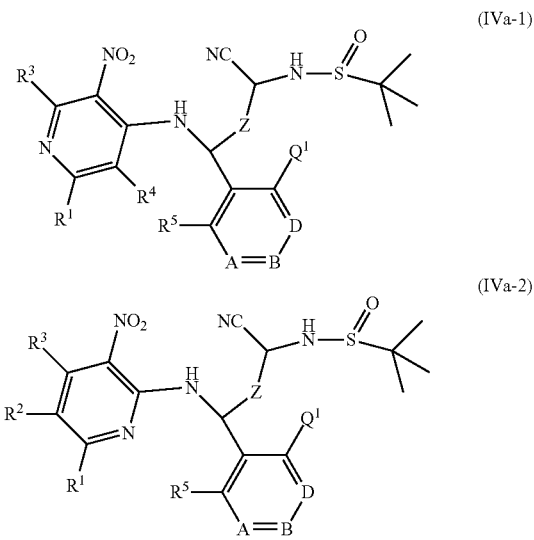

wherein A, B, D, Z, $R^1$, $R^2$, $R^3$, $R^4$, $R^5$ and $Q^1$ are as defined above.

The reaction is conveniently performed in the presence of tin(II) chloride, with the addition of a strong acid, e.g. hydrochloric acid, at an elevated temperature in a suitable solvent, e.g. ethanol.

Alternatively, the transformation may be effected by a procedure involving: (i) reduction using hydrogen gas under pressure, in the presence of zinc bromide and a hydrogenation catalyst, e.g. platinum on charcoal; and (ii) addition of a strong acid, e.g. hydrochloric acid or sulphuric acid, at an elevated temperature in a suitable solvent, e.g. ethanol.

The intermediates of formula (IVa-1) and (IVa-2) may be prepared by a multi-step process starting from an intermediate of formula (Va-1) or (Va-2) respectively:

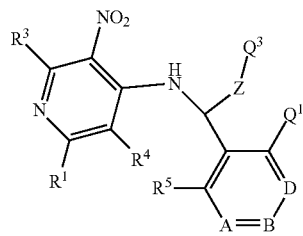
(Va-1)

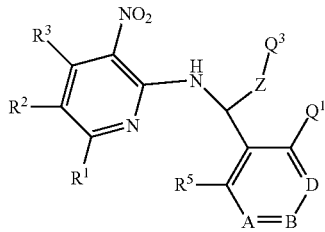
(Va-2)

wherein A, B, D, Z, $R^1$, $R^2$, $R^3$, $R^4$, $R^5$ and $Q^1$ are as defined above, and $Q^3$ represents —CH=$CH_2$; which process comprises the following steps:

(i) reacting intermediate (Va-1) or (Va-2) with osmium tetroxide, in the presence of 4-methylmorpholine N-oxide, to afford the corresponding intermediate of formula (Va-1) or (Va-2) wherein $Q^3$ represents —CH(OH)$CH_2$OH;

(ii) reacting the compound thereby obtained with sodium periodate, to afford the corresponding intermediate of formula (Va-1) or (Va-2) wherein $Q^3$ represents —CH=O;

(iii) reacting the compound thereby obtained with (R)-2-methylpropane-2-sulfinamide in the presence of a transition metal catalyst, e.g. titanium(IV) ethoxide or titanium(IV) isopropoxide, in a suitable solvent, e.g. dichloromethane, to afford the corresponding intermediate of formula (Va-1) or (Va-2) wherein $Q^3$ represents —CH=N—S(=O)—C($CH_3$)$_3$; and (iv) reacting the compound thereby obtained with trimethylsilyl cyanide or sodium cyanide in the presence of scandium triflate.

In an alternative procedure, the intermediates of formula (IVa-1) and (IVa-2) may be prepared from the corresponding compound of formula (V-1) or (V-2) respectively as defined above by a two-step process which comprises:

(i) treatment with (R)-2-methylpropane-2-sulfinamide in the presence of a transition metal catalyst, e.g. titanium(IV) ethoxide or titanium(IV) isopropoxide, in a suitable solvent, e.g. dichloromethane, to afford the corresponding intermediate of formula (V-1) or (V-2) wherein $Q^2$ represents —CH=N—S(=O)—C($CH_3$)$_3$; and (ii) reacting the compound thereby obtained with trimethylsilyl cyanide or sodium cyanide in the presence of scandium triflate.

The intermediates of formula (Va-1) and (Va-2) as defined above may be prepared by reacting an intermediate of formula (VI-1) or (VI-2) respectively as defined above with an intermediate of formula (VIIa):

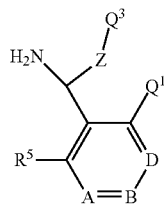

(VIIa)

wherein A, B, D, Z, $R^5$, $Q^1$ and $Q^3$ are as defined above; under conditions analogous to those described above for the preparation of the intermediates of formula (V-1) and (V-2).

The intermediates of formula (VII) and (VIIa) may be prepared by the procedures described in WO 2016/050975 and in the accompanying Examples, or by procedures analogous thereto, or by alternative procedures well known from the art.

In an alternative procedure, the intermediates of formula (III) wherein E represents a group of formula (Ea) or (Eb) as defined above, $R^{12}$ represents hydrogen and —$X^1$ represents —NH($R^g$), in which $R^g$ represents hydrogen, may be prepared from the corresponding intermediate of formula (IVa-1) or (IVa-2) respectively as defined above by a process which comprises the following steps:

(i) treatment with a strong acid, e.g. a mineral acid such as hydrochloric acid, then with a base, e.g. an alkali metal hydroxide such as sodium hydroxide, to effect desulfinylation and conversion of the cyano group to a carboxylic acid (—$CO_2H$) group;

(ii) esterification of the compound thereby obtained by treatment with a lower alkanol, e.g. methanol, in the presence of an acid, e.g. a mineral acid such as sulfuric acid, typically at an elevated temperature;

(iii) reduction of the nitro group in the compound thereby obtained by treatment with a reducing agent, e.g. tin(II) chloride, typically at an elevated temperature in a suitable solvent, e.g. a lower alkanol such as methanol; and (iv) saponification and intramolecular cyclisation of the compound thereby obtained by treatment with a strong base, e.g. sodium tert-butoxide.

The intermediates of formula (III) wherein E represents a group of formula (Ec) as defined above, $R^{12}$ represents hydrogen and $X^1$ represents hydroxy may be prepared from an intermediate of formula (IIIA):

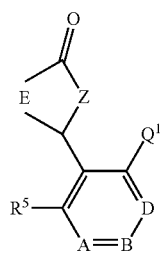

(IIIA)

wherein A, B, D, Z, E, $R^5$ and $Q^1$ are as defined above; by reduction of the carbonyl moiety according to methods known to the person skilled in the art.

The intermediates of formula (III) wherein E represents a group of formula (Ec) as defined above, $R^{12}$ represents methyl and $X^1$ represents —NH($R^f$), in which $R^f$ represents hydrogen, may be prepared from an intermediate of formula (IIIA) utilising the following sequence of steps:

(i) reacting an intermediate of formula (IIIA) with 2-methylpropane-2-sulfinamide in the presence of titanium (IV) isopropoxide in a solvent, e.g. tetrahydrofuran;

(ii) adding a solution of methylmagnesium bromide, at low temperature, in a suitable solvent, e.g. dichloromethane; and (iii) removing the tert-butylsulphinyl moiety by treatment with a strong acid, e.g. hydrochloric acid, in a suitable solvent, e.g. 1,4-dioxane.

The intermediates of formula (IIIA) may be prepared by the intramolecular cyclization of an intermediate of formula (VIII):

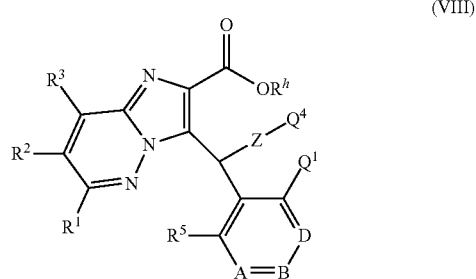

(VIII)

wherein $Q^4$ is an electron-withdrawing group, preferably an ester moiety, and A, B, D, Z, $R^1$, $R^2$, $R^3$, $R^5$, $R^h$ and $Q^1$ are as defined above; in the presence of a base.

The reaction may conveniently be effected in a suitable solvent at an elevated temperature.

The intermediates of formula (VIII) may be prepared by reacting an intermediate of formula (IX) with an intermediate of formula (X):

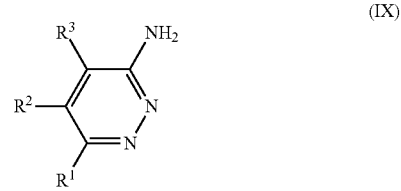

(IX)

(X)

wherein A, B, D, Z, $R^1$, $R^2$, $R^3$, $R^5$, $R^h$, $Q^1$ and $Q^4$ are as defined above, and $L^2$ represents a suitable leaving group.

The leaving group $L^2$ is typically a halogen atom, e.g. bromo.

The reaction is conveniently effected at an elevated temperature in a suitable solvent, e.g. a $C_{1-4}$ alkanol such as ethanol, or an ether such as 1,4-dioxane or 1,2-dimethoxyethane, typically in the presence of magnesium sulphate.

Alternatively, the intermediates of formula (VIII) wherein Z is methylene and $Q^4$ is —$CO_2H$ may be prepared by reacting an intermediate of formula (XI) with an intermediate of formula (XII):

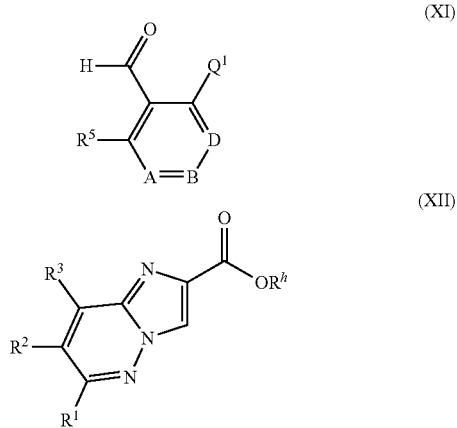

wherein A, B, D, $R^1$, $R^2$, $R^3$, $R^5$, $R^h$ and $Q^1$ are as defined above; in the presence of Meldrum's acid, according to a method analogous to that described in WO 2009/156091; or by M. Kerr et al. in *J. Org. Chem.*, 2013, 78, 10534.

The reaction is conveniently effected at an elevated temperature in a suitable solvent, e.g. acetonitrile, in the presence of proline and magnesium sulphate.

Where they are not commercially available, the starting materials of formula (VI-1), (VI-2), (IX), (X), (XI) and (XII) may be prepared by methods analogous to those described in the accompanying Examples, or by standard methods well known from the art.

The intermediates of formula (III) wherein $X^1$ represents amino may be prepared from a corresponding intermediate of formula (III) wherein $X^1$ is hydroxy by a stepwise procedure which comprises: (i) treatment with diphenyl phosphoryl azide and 1,8-diazabicyclo[5.4.0]undec-7-ene in a suitable solvent, e.g. tetrahydrofuran; and (ii) subsequent aza-Wittig reaction using triphenylphosphine in a suitable solvent, e.g. a mixture of water and toluene.

The intermediates of formula (III) wherein E represents a group of formula (Ec) as defined above, $R^{12}$ is hydrogen, and $X^1$ represents amino, may be prepared from an intermediate of formula (IIIA) by reaction with a $C_{1-6}$ alkylsulfinamide, e.g. (R)-2-methyl-propane-2-sulfinamide, in the presence of a transition metal catalyst, e.g. titanium(IV) ethoxide, in a suitable solvent, e.g. dichloromethane, followed by reduction with a suitable reducing agent, e.g. sodium borohydride, in a suitable solvent, e.g. tetrahydrofuran, and subsequent removal of the sulfinyl moiety, typically by treatment with a mineral acid, e.g. hydrochloric acid.

The intermediates of formula (III) wherein $X^1$ represents Y or —$CH_2$—Y, in which Y represents a leaving group, e.g. halogen or ($C_{1-6}$)alkylsulphonyloxy, may be prepared from an intermediate of formula (III) wherein $X^1$ is hydroxy or —$CH_2OH$ respectively according to standard methods known to the person skilled in the art.

The intermediates of formula (III) wherein $X^1$ represents —SH may be prepared from an intermediate of formula (III) wherein $X^1$ is hydroxy or a leaving group Y according to standard methods known to the person skilled in the art.

The intermediates of formula (III) wherein $X^1$ represents —$CO_2H$ may be prepared by hydrolysis of a corresponding intermediate of formula (III) wherein $X^1$ represents cyano according to standard methods known to the person skilled in the art.

The intermediates of formula (III) wherein $X^1$ represents cyano may be prepared by nucleophilic substitution of an intermediate of formula (III) wherein $X^1$ represents a leaving group Y, in which Y represents ($C_{1-6}$)alkylsulphonyloxy, according to standard methods known to the person skilled in the art.

The intermediates of formula (III) wherein $X^1$ represents —$CH_2OH$ may be prepared by reduction of the corresponding intermediate of formula (III) wherein $X^1$ represents —$CO_2H$ by treatment with a suitable reducing reagent, e.g. $BH_3$.

The intermediates of formula (III) wherein $X^1$ represents —NH($R^g$), in which $R^g$ represents —$COR^d$, may be prepared by reacting a compound of formula (III) wherein $X^1$ represents —$NH_2$ with a compound of formula $R^d$—$CO_2H$ in the presence of a base, e.g. N,N-diisopropylethylamine, and a coupling agent, e.g. N-[(dimethylamino)-1H-1,2,3-triazolo-[4,5-b]pyridin-1-ylmethylene]-N-ethylmethanaminium hexafluorophosphate N-oxide (HATU), in a suitable solvent, e.g. N,N-dimethylformamide.

The intermediates of formula (III) wherein $Q^1$ represents formyl may be prepared from an intermediate of formula (III) wherein $Q^1$ represents halogen, e.g. bromine, by a stepwise process involving: (i) reaction with potassium vinylfluoroborate in the presence of a base and a transition metal catalyst; and (ii) reaction with sodium periodate and osmium tetraoxide in the presence of a suitable solvent, e.g. a cyclic ether such as 1,4-dioxane. In step (i), suitable bases include inorganic bases such as cesium carbonate; and suitable transition metal catalysts include 1,1'-bis(diphenylphosphino)ferrocene-palladium(II) dichloride-dichloromethane complex.

The intermediates of formula (III) wherein $Q^1$ represents acetyl may be prepared from an intermediate of formula (III) wherein $Q^1$ represents halogen, e.g. bromine, by a stepwise process involving: (i) reaction with tributyl(1-ethoxyvinyl)tin in the presence of bis(triphenylphosphine)palladium(II) dichloride in a suitable solvent, e.g. toluene, at an elevated temperature; and (ii) reaction with an acid, e.g. p-toluenesulphonic acid.

The intermediates of formula (III) wherein $Q^1$ represents —$S(CH_2)_2CO_2CH_2CH(CH_2CH_3)[(CH_2)_3CH_3]$ may be prepared from an intermediate of formula (III) wherein $Q^1$ represents halogen, e.g. bromine, by reaction with 3-mercapto-propionic acid 2-ethyl ester in the presence of a suitable transition metal catalyst, e.g. tris(benzylideneacetone)dipalladium(0) and 4,5-bis(diphenylphosphino)-9,9-dimethylxanthene, in a suitable solvent, e.g. 1,4-dioxane, at an elevated temperature.

Similarly, the intermediates of formula (III) wherein $Q^1$ represents —$SCH_2CO_2CH_2CH_3$ may be prepared from intermediates of formula (III) wherein $Q^1$ represents halogen, e.g. bromine, by reaction with ethyl thioglycolate in the presence of a suitable transition metal catalyst, e.g. tris (benzylideneacetone)dipalladium(0) and 4,5-bis(diphenylphosphino)-9,9-dimethylxanthene, in a suitable solvent, e.g. 1,4-dioxane, at an elevated temperature.

The intermediates of formula (III) wherein $Q^1$ represents —$SCH_3$ may be prepared from an intermediate of formula (III) wherein $Q^1$ represents halogen, e.g. bromine, by a process which involves treatment with sodium thiomethoxide in a suitable solvent, e.g. dimethyl sulphoxide, at an elevated temperature.

The intermediates of formula (III) wherein $Q^1$ represents —CH(OH)CF$_3$ may be prepared from an intermediate of formula (III) wherein $Q^1$ represents —C(O)H by reaction with tetrabutylammonium fluoride, followed by (trifluoromethyl)trimethylsilane, in a suitable solvent, e.g. tetrahydrofuran.

It will be understood that any compound of formula (I) initially obtained from any of the above processes may, where appropriate, subsequently be elaborated into a further compound of formula (I) by techniques known from the art.

By way of example, a compound of formula (I) wherein —X-Q- represents —O—CH$_2$— may be prepared by reduction of a corresponding compound of formula (I) wherein —X-Q-represents —O—C(O)— according to the method described in Sakai et al., *J. Org. Chem.*, 2007, 72, 5920-5922.

A compound of formula (I) wherein —X-Q- represents —N(R$^g$)—CH$_2$— may be prepared in a similar fashion from a corresponding compound of formula (I) wherein —X-Q- represents —N(R$^f$)—CO—; or under any other lactam reduction conditions known to the person skilled in the art.

A compound of formula (I) wherein —X-Q- represents —S—, —CH$_2$—S— or —S—CH$_2$— may be transformed into the corresponding compound of formula (I) wherein —X-Q-represents —SO—, —SO$_2$—, —CH$_2$—SO—, —CH$_2$—SO$_2$—, —SO—CH$_2$— or —SO$_2$—CH$_2$—, by performing an oxidation reaction according to methods known to the person skilled in the art.

A compound of formula (I) wherein —X-Q- represents —SO—, —CH$_2$—SO— or —SO—CH$_2$— may be transformed into the corresponding compound of formula (I) wherein —X-Q-represents —S(O)(NH)—, —CH$_2$—S(O)(NH)— or —S(O)(NH)—CH$_2$— respectively by a method analogous to that described in Okamura, H. et al., *Organic Letters*, 2004, 6(8), 1305-1307.

A compound of formula (I) wherein —X-Q- represents —S— may be transformed into the corresponding compound of formula (I) wherein —X-Q- represents —S(=N—CN)— by reaction with iodobenzene diacetate in the presence of cyanamide. The reaction is conveniently effected in acetonitrile.

A compound of formula (I) wherein —X-Q- represents —N(R$^f$)—C(O)— may be converted into the corresponding compound of formula (I) wherein —X-Q- represents —N(R$^f$)—C(S)— by treatment with Lawesson's reagent according to methods known to the person skilled in the art.

A compound of formula (I) wherein —X-Q- represents —NH— may be transformed into the corresponding compound of formula (I) wherein —X-Q- represents —N(R$^g$)—, in which R$^g$ represents —COR$^d$, by reaction with a compound of formula R$^d$—COCl in a suitable solvent, e.g. dichloromethane.

A compound of formula (I) or (III) wherein R$^f$ or R$^g$ represents hydrogen may be transformed into the corresponding compound of formula (I) or (III) wherein R$^f$ or R$^g$ represents optionally substituted C$_{1-6}$ alkyl, or its deuterated equivalent, by reaction with the appropriate optionally substituted C$_{1-6}$ alkyl halide or deuterated equivalent thereof, e.g. a C$_{1-6}$ alkyl iodide (such as iodomethane) or its deuterated equivalent, in the presence of a base, e.g. sodium hydride, or cesium carbonate, or potassium bis(trimethylsilyl)amide (KHMDS), in a suitable solvent, e.g. N,N-dimethylformamide or tetrahydrofuran.

A compound of formula (I) or (III) wherein R$^f$ or R$^g$ represents hydrogen may be transformed into the corresponding compound of formula (I) or (III) wherein R$^f$ or R$^g$ represents methyl by reaction with formaldehyde in a suitable solvent, e.g. 2,2,2-trifluoroethanol, followed by reaction with a suitable reducing agent, e.g. sodium borohydride.

A compound of formula (I) or (III) wherein R$^f$ or R$^g$ represents hydrogen may be transformed into the corresponding compound of formula (I) or (III) wherein R$^f$ or R$^g$ represents acetyl by reaction with acetic anhydride in the presence of base, e.g. pyridine, in a suitable solvent, e.g. dichloromethane.

A compound of formula (I) or (III) wherein R$^f$ or R$^g$ represents hydrogen may be transformed into the corresponding compound of formula (I) or (III) wherein R$^f$ or R$^g$ represents C$_{1-6}$ alkylsulphonyl by treatment with the appropriate C$_{1-6}$ alkylsulphonyl halide, e.g. methanesulphonyl chloride, in the presence of a suitable base, e.g. N,N-diisopropylethylamine or triethylamine, in a suitable solvent, e.g. dichloromethane.

A compound of formula (I) or (III) which contains a hydroxy group may be alkylated by treatment with the appropriate alkyl halide in the presence of a base, e.g. sodium hydride, or silver oxide.

A compound of formula (I) or (III) which contains hydroxy may be converted into the corresponding fluoro-substituted compound by treatment with diethylaminosulfur trifluoride (DAST) or bis(2-methoxyethyl)aminosulfur trifluoride (BAST). A compound of formula (I) which contains hydroxy may be converted into the corresponding difluoro-substituted compound via a two-step procedure which comprises: (i) treatment with an oxidising agent, e.g. manganese dioxide; and (ii) treatment of the carbonyl-containing compound thereby obtained with DAST.

A compound of formula (I) or (III) which contains an N—H moiety may be alkylated by treatment with the appropriate alkyl halide, typically at an elevated temperature in an organic solvent such as acetonitrile; or at ambient temperature in the presence of a base, e.g. potassium hydroxide, in a suitable solvent, e.g. tetrahydrofuran, in the presence of tetrabutylammonium bromide; or at an elevated temperature in the presence of a base, e.g. sodium hydride, with or without tetrabutylammonium iodate, in a suitable solvent, e.g. tetrahydrofuran; or at elevated temperature in the presence of an alkali metal carbonate such as potassium carbonate or cesium carbonate, in a suitable solvent, e.g. a dipolar aprotic solvent such as N,N-dimethylformamide. A compound of formula (I) which contains an N—H moiety may be methylated by treatment with formaldehyde in the presence of a reducing agent, e.g. sodium triacetoxyborohydride.

A compound of formula (I) or (III) which contains an N—H moiety may be acylated by treatment with the appropriate acid chloride, e.g. acetyl chloride, or with the appropriate carboxylic acid anhydride, e.g. acetic anhydride, typically at ambient temperature in the presence of a base, e.g. an organic base such as triethylamine.

A compound of formula (I) or (III) which contains an N—H moiety may be converted into the corresponding compound wherein the nitrogen atom is substituted by C$_{1-6}$ alkoxycarbonyl, e.g. methoxycarbonyl, by treatment with the corresponding C$_{1-6}$ alkoxycarbonyl halide in the presence of a base, e.g. potassium carbonate, in a suitable solvent, e.g. N,N-dimethylformamide.

A compound of formula (I) or (III) which contains an N—H moiety may be converted into the corresponding compound wherein the nitrogen atom is substituted by C$_{1-6}$ alkylsulphonyl, e.g. methylsulphonyl, by treatment with the appropriate C$_{1-6}$ alkylsulphonyl chloride, e.g. methanesulphonyl chloride, or with the appropriate C$_{1-6}$ alkylsulphonic acid anhydride, e.g. methanesulphonic anhydride, typically at ambient temperature in the presence of a base, e.g. an organic base such as triethylamine or N,N-diisopropylethylamine.

A compound of formula (I) or (III) substituted by amino (—$NH_2$) may be converted into the corresponding compound substituted by $C_{1-6}$ alkylsulphonylamino, e.g. methylsulphonylamino, or bis[($C_{1-6}$)alkylsulphonyl]amino, e.g. bis(methylsulphonyl)amino, by treatment with the appropriate $C_{1-6}$ alkylsulphonyl halide, e.g. a $C_{1-6}$ alkylsulphonyl chloride such as methanesulphonyl chloride, in the presence of a suitable base, e.g. N,N-diisopropylethylamine, in a suitable solvent, e.g. dichloromethane.

Thus, a compound of formula (I) or (III) substituted by amino may be transformed into the corresponding compound substituted by —$NHSO_2R^e$ by treatment with a compound of formula $R^e$—$SO_2Cl$.

Similarly, a compound of formula (I) substituted by hydroxy (—OH) may be converted into the corresponding compound substituted by $C_{1-6}$ alkylsulphonyloxy, e.g. methylsulphonyloxy, by treatment with the appropriate $C_{1-6}$ alkylsulphonyl halide, e.g. a $C_{1-6}$ alkylsulphonyl chloride such as methanesulphonyl chloride.

A compound of formula (I) or (III) containing the moiety —S— may be converted into the corresponding compound containing the moiety —S(O)— by treatment with 3-chloroperoxybenzoic acid. Likewise, a compound of formula (I) or (III) containing the moiety —S(O)— may be converted into the corresponding compound containing the moiety —$S(O)_2$— by treatment with 3-chloroperoxybenzoic acid. Alternatively, a compound of formula (I) containing the moiety —S— may be converted into the corresponding compound containing the moiety —$S(O)_2$— by treatment with Oxone® (potassium peroxymonosulfate).

A compound of formula (I) or (III) containing an aromatic nitrogen atom may be converted into the corresponding N-oxide derivative by treatment with 3-chloroperoxybenzoic acid.

A compound of formula (I) or (III) which contains a carbonyl (C=O) moiety may be converted into the corresponding compound containing a CH(OH) functionality by treatment with a suitable borohydride reagent, e.g. lithium tri-sec-butyl borohydride or sodium borohydride, in a suitable solvent e.g. tetrahydrofuran.

A compound of formula (I) or (III) wherein $R^1$ represents halogen, e.g. bromo, may be converted into the corresponding compound wherein $R^1$ represents an optionally substituted aryl or heteroaryl moiety by treatment with the appropriately substituted aryl or heteroaryl boronic acid or a cyclic ester thereof formed with an organic diol, e.g. pinacol, 1,3-propanediol or neopentyl glycol. The reaction is typically effected at an elevated temperature in the presence of a transition metal catalyst, e.g. [1,1'-bis(diphenyl-phosphino)ferrocene]dichloropalladium(II), tetrakis(triphenylphosphine)palladium(0), bis[3-(diphenylphosphanyl)cyclopenta-2,4-dien-1-yl]iron-dichloropalladium-dichloromethane complex, or tris(dibenzylideneacetone)dipalladium(0) and tricyclohexylphosphonium tetrafluoroborate, and a base, e.g. an inorganic base such as sodium carbonate, potassium carbonate or cesium carbonate, or potassium phosphate, in a suitable solvent, e.g. 1,4-dioxane or a mixture of 1,4-dioxane and water.

A compound wherein $R^1$ represents halogen, e.g. chloro or bromo, may be converted into the corresponding compound wherein $R^1$ represents an optionally substituted aryl or heteroaryl moiety via a two-step procedure which comprises: (i) reaction with bis(pinacolato)diboron or bis(neopentyl glycolato)diboron; and (ii) reaction of the compound thereby obtained with an appropriately functionalised halo-substituted aryl or heteroaryl derivative. Steps (i) and (ii) may be conveniently effected in the presence of a transition metal catalyst such as tris(dibenzylideneacetone)dipalladium(0) and tricyclohexylphosphonium tetrafluoroborate.

A compound of formula (I) wherein $R^1$ represents 2-oxo-(1H)-pyridinyl may be obtained by treatment of the corresponding compound wherein $R^1$ represents 2-methoxy-pyridinyl with pyridine hydrochloride at an elevated temperature.

A compound of formula (I) or (III) wherein $R^1$ represents an ester moiety may be obtained by reacting the corresponding compound wherein $R^1$ is halogen, e.g. chloro, with a base, e.g. sodium carbonate, and the appropriate alcohol in the presence of carbon monoxide and a transition metal catalyst, typically [1,3-bis(dicyclohexylphosphino)-propane]palladium(II).

A compound of formula (I) or (III) wherein $R^1$ represents cyano may be obtained by reacting the corresponding compound of formula (I) or (III) wherein $R^1$ is halogen, e.g. chloro, with zinc cyanide in the presence of a transition metal catalyst, e.g. tetrakis-(triphenylphosphine)palladium (0), in a suitable solvent, e.g. N,N-dimethylformamide.

In general, a compound of formula (I) containing a —C≡C— functionality may be converted into the corresponding compound containing a —CH—CH— functionality by catalytic hydrogenation, typically by treatment with a hydrogenation catalyst, e.g. palladium on charcoal, under an atmosphere of hydrogen gas, optionally in the presence of a base, e.g. an alkali metal hydroxide such as sodium hydroxide.

A compound of formula (I) containing an ester moiety, e.g. a $C_{2-6}$ alkoxycarbonyl group such as methoxycarbonyl or ethoxycarbonyl, may be converted into the corresponding compound containing a carboxy (—$CO_2H$) moiety by treatment with an acid, e.g. a mineral acid such as hydrochloric acid.

A compound of formula (I) containing an ester moiety, e.g. a $C_{2-6}$ alkoxycarbonyl group such as methoxycarbonyl or ethoxycarbonyl, may alternatively be converted into the corresponding compound containing a carboxy (—$CO_2H$) moiety by treatment with a base, e.g. an alkali metal hydroxide selected from lithium hydroxide, sodium hydroxide and potassium hydroxide; or an organic base such as sodium methoxide or sodium ethoxide.

A compound of formula (I) containing a carboxy (—$CO_2H$) moiety may be converted into the corresponding compound containing an amide moiety by treatment with the appropriate amine in the presence of a condensing agent such as 1-ethyl-3-(3-dimethyl-aminopropyl)carbodiimide.

A compound of formula (I) containing a carbonyl (C=O) moiety may be converted into the corresponding compound containing a —$C(CH_3)(OH)$— moiety by treatment with methylmagnesium bromide. Similarly, a compound of formula (I) containing a carbonyl (C=O) moiety may be converted into the corresponding compound containing a —$C(CF_3)(OH)$— moiety by treatment with (trifluoromethyl)trimethylsilane and cesium fluoride. A compound of formula (I) containing a carbonyl (C=O) moiety may be converted into the corresponding compound containing a —$C(CH_2NO_2)(OH)$— moiety by treatment with nitromethane.

A compound of formula (I) containing a hydroxymethyl moiety may be converted into the corresponding compound containing a formyl (—CHO) moiety by treatment with an oxidising agent such as Dess-Martin periodinane. A compound of formula (I) containing a hydroxymethyl moiety may be converted into the corresponding compound containing a carboxy moiety by treatment with an oxidising agent such as tetrapropylammonium perruthenate.

A compound of formula (I) containing an aryl or heteroaryl moiety may be transformed into the corresponding compound, wherein a hydrogen atom in the aryl or heteroaryl moiety has been replaced by chloro or bromo, by reaction with N-chloro-succinimide or N-bromosuccinimide respectively in a suitable solvent, e.g. N,N-dimethylformamide, according to methods known to the person skilled in the art.

A compound of formula (I) containing an aryl moiety bearing a difluoromethoxy group may be transformed into the corresponding compound, wherein the difluoromethoxy group in the aryl moiety has been replaced by a hydroxy group, by reaction with sodium bis(trimethylsilyl)amide (NaHMDS) in a suitable solvent, e.g. tetrahydrofuran.

A compound of formula (I) containing an aryl or heteroaryl moiety may be transformed into the corresponding compound, wherein a hydrogen atom in the aryl or heteroaryl moiety has been replaced by trifluoromethyl, by a stepwise procedure which comprises: (i) treatment with trifluoroacetic acid in a suitable solvent, e.g. acetonitrile; and (ii) addition of trifluoromethanesulphonyl chloride, followed by [4,4'-bis(tert-butyl)-2,2'-bipyridine]bis{3,5-difluoro-2-[5-(trifluoromethyl)pyridin-2-yl]phenyl}iridium (III) hexafluorophosphate, according to conditions analogous to those described by McMillan et al. in *Nature*, 2011, 480, 224.

A compound of formula (I) substituted by phosphate($C_{1-6}$)alkyl may be prepared from the corresponding compound substituted by hydroxy($C_{1-6}$)alkyl by a stepwise procedure which comprises: (i) treatment with dibenzyl N,N-diisopropylphosphoramidite in a suitable solvent, e.g. dichloromethane, followed by treatment with hydrogen peroxide; and (ii) hydrogenolysis, e.g. using hydrogen gas under pressure, in the presence of a suitable catalyst, e.g. palladium on charcoal, according to a method analogous to those described by S. P. Green et al. in *Organic Process Research & Development*, 2002, 6, 109-112. A compound of formula (I) substituted by a salt of phosphate($C_{1-6}$)alkyl may be prepared by performing step (ii) in the presence of a suitable alkali metal base or alkaline earth metal base. Similarly, an isolated compound of formula (I) substituted by phosphate-($C_{1-6}$)alkyl may be converted into the corresponding compound substituted by a salt of phosphate($C_{1-6}$)alkyl by treatment with an appropriate base, e.g. an alkali metal base, or an alkaline earth metal base, or ammonia, or an organic amine, in a suitable solvent according to methods known to the person skilled in the art. Suitable alkali metal bases include sodium hydroxide and potassium hydroxide. Suitable alkaline earth metal bases include calcium hydroxide. Suitable organic amines include triethylamine.

A compound of formula (I) substituted by ($C_{1-6}$)alkylphosphate($C_{1-6}$)alkyl may be prepared from the corresponding compound substituted by hydroxy($C_{1-6}$)alkyl by a stepwise procedure which comprises: (i) reacting cyanoethyl phosphoramidite with the appropriate $C_{1-6}$ alkanol in the presence of a base, e.g. N,N-diisopropylethylamine, in a suitable solvent, e.g. dichloromethane; (ii) addition of the relevant compound of formula (I) substituted by hydroxy ($C_{1-6}$)alkyl in a suitable solvent, e.g. dichloromethane; and (iii) oxidation and subsequent treatment with a suitable base, according to a method analogous to those described by Nam, N—H. et al. in *Bio-org. Med. Chem.*, 2004, 12, 6255; and in WO 2012/177707.

A compound of formula (I) substituted by sulphate($C_{1-6}$) alkyl may be prepared by treatment of the corresponding compound substituted by hydroxy($C_{1-6}$)alkyl with pyridine: sulphur trioxide complex, according to a method analogous to that described by E. Lacko et al. in *Current Medicinal Chemistry*, 2012, 19, 4699; or by treatment with chlorosulphonic acid in the presence of triethylamine, according to a method analogous to that described in WO 2004/087720.

A compound of formula (I) substituted by phosphate-methoxy($C_{1-6}$)alkyl may be prepared by reacting the corresponding compound substituted by hydroxy($C_{1-6}$)alkyl with a suitable base, e.g. sodium hydride, in a suitable solvent, e.g. 1,2-dimethoxyethane, followed by addition of chloromethyl di-tert-butylphosphate, with subsequent dealkylation at an elevated temperature, according to a method analogous to that described in WO 2012/135082.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention. Alternatively the non-desired enantiomer may be racemized into the desired enantiomer, in the presence of an acid or a base, according to methods known to the person skilled in the art, or according to methods described in the accompanying Examples.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, $3^{rd}$ edition, 1999. The protecting groups may be removed at any convenient subsequent stage utilising methods known from the art.

Compounds in accordance with the present invention potently neutralise the activity of TNFα in a commercially available HEK-293 derived reporter cell line known as HEK-Blue™ CD40L. This is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a concentration-dependent manner by TNFα. When tested in the HEK-293 bioassay, also referred to herein as the reporter gene assay, compounds of the present invention exhibit an $IC_{50}$ value of 50 µM or less, generally of 20 µM or less, usually of 5 µM or less, typically of 1 µM or less, suitably of 500 nM or less, ideally of 100 nM or less, and preferably of 25 nM or less (the skilled person will appreciate that a lower $IC_{50}$ figure denotes a more active compound).

Compounds in accordance with the present invention may also be tested in the fluorescence polarisation assay described herein.

The compounds of the Examples have been tested in one or both of the assays described below.

Fluorescence Polarisation Assay
Preparation of Compound (A)

1-(2,5-Dimethylbenzyl)-6-[4-(piperazin-1-ylmethyl)phenyl]-2-(pyridin-4-yl-methyl)-1H-benzimidazole —hereinafter referred to as "Compound (A)"—can be prepared by the procedure described in Example 499 of WO 2013/186229; or by a procedure analogous thereto.

Preparation of Fluorescence Conjugate

Compound (A) (27.02 mg, 0.0538 mmol) was dissolved in DMSO (2 mL). 5 (−6) Carboxy-fluorescein succinimyl ester (24.16 mg, 0.0510 mmol) (Invitrogen catalogue number: C1311) was dissolved in DMSO (1 mL) to give a bright yellow solution. The two solutions were mixed at room temperature, the mixture turning red in colour. The mixture was stirred at room temperature. Shortly after mixing a 20 µL aliquot was removed and diluted in a 80:20 mixture of $AcOH:H_2O$ for LC-MS analysis on the 1200RR-6140 LC-MS system. The chromatogram showed two closely eluting peaks at retention times of 1.42 and 1.50 minutes, both with mass $(M+H)^+=860.8$ amu, corresponding to the two products formed with the 5- and 6-substituted carboxyfluorescein group. A further peak at retention time 2.21 minutes had a mass of $(M+H)^+=502.8$ amu, corresponding to Compound (A). No peak was observed for unreacted 5(−6) carboxyfluorescein succinimyl ester. The peak areas were 22.0%, 39.6% and 31.4% for the three signals, indicating a 61.6% conversion to the two isomers of the desired fluorescence conjugate at that time-point. Further 20 µL aliquots were extracted after several hours and then after overnight stirring, diluted as before and subjected to LC-MS analysis. The percentage conversion was determined as 79.8% and 88.6% respectively at these time-points. The mixture was purified on a UV-directed preparative HPLC system. The pooled purified fractions were freeze-dried to remove excess solvent. After freeze-drying, an orange solid (23.3 mg) was recovered, equivalent to 0.027 mmol of fluorescence conjugate, corresponding to an overall yield of 53% for the reaction and preparative HPLC purification.

Inhibition of Binding of Fluorescence Conjugate to TNFα

Compounds are tested at 10 concentrations starting from 25 µM in a final assay concentration of 5% DMSO, by pre-incubation with TNFα for 60 minutes at ambient temperature in 20 mM Tris, 150 mM NaCl, 0.05% Tween 20, before addition of the fluorescence conjugate and a further incubation for 20 hours at ambient temperature. The final concentrations of TNFα and the fluorescence conjugate are 10 nM and 10 nM respectively in a total assay volume of 25 µL. Plates are read on a plate reader capable of detecting fluorescence polarisation (e.g. an Analyst HT plate reader; or an Envision plate reader). An $IC_{50}$ value is calculated using XLfit™ (4 parameter logistic model) in ActivityBase.

When tested in the fluorescence polarisation assay, the compounds of the accompanying Examples were all found to exhibit $IC_{50}$ values of 50 µM or better.

When tested in the fluorescence polarisation assay, compounds of the accompanying Examples exhibit $IC_{50}$ values generally in the range of about 0.01 nM to about 50 µM, usually in the range of about 0.01 nM to about 20 µM, typically in the range of about 0.01 nM to about 5 µM, suitably in the range of about 0.01 nM to about 1 µM, ideally in the range of about 0.01 nM to about 500 nM, appositely in the range of about 0.01 nM to about 100 nM, and preferably in the range of about 0.01 nM to about 25 nM.

Reporter Gene Assay
Inhibition of TNFα-Induced NF-κB Activation

Stimulation of HEK-293 cells by TNFα leads to activation of the NF-κB pathway. The reporter cell line used to determine TNFα activity was purchased from InvivoGen. HEK-Blue™ CD40L is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a dose-dependent manner by TNFα, with an EC50 of 0.5 ng/mL for human TNFα. Compounds were diluted from 10 mM DMSO stocks (final assay concentration 0.3% DMSO) to generate a 10-point 3-fold serial dilution curve (e.g. 30,000 nM to 2 nM final concentration). Diluted compound was preincubated with TNFα for 60 minutes prior to addition to a 384-well microtitre plate and incubated for 18 h. The final TNFα concentration in the assay plate was 0.5 ng/mL. SEAP activity was determined in the supernatant using a colorimetric substrate, e.g. QUANTI-Blue™ or HEK-Blue™ Detection media (InvivoGen). Percentage inhibitions for compound dilutions were calculated between a DMSO control and maximum inhibition (by excess control compound) and an $IC_{50}$ value calculated using XLfit™ (4 parameter logistic model) in ActivityBase.

When tested in the reporter gene assay, the compounds of the accompanying Examples were all found to exhibit $IC_{50}$ values of 50 µM or better.

When tested in the reporter gene assay, compounds of the accompanying Examples exhibit $IC_{50}$ values generally in the range of about 0.01 nM to about 50 µM, usually in the range of about 0.01 nM to about 20 µM, typically in the range of about 0.01 nM to about 5 µM, suitably in the range of about 0.01 nM to about 1 µM, appositely in the range of about 0.01 nM to about 500 nM, ideally in the range of about 0.01 nM to about 100 nM, and preferably in the range of about 0.01 nM to about 25 nM.

The following Examples illustrate the preparation of compounds according to the invention.

EXAMPLES

| Abbreviations | |
|---|---|
| DCM: dichloromethane | EtOAc: ethyl acetate |
| DMF: N,N-dimethylformamide | MeOH: methanol |
| DMSO: dimethyl sulfoxide | THF: tetrahydrofuran |
| MTBE: tert-butyl methyl ether | DIPEA: N,N-diisopropylethylamine |
| Dess-Martin periodinane: 1,1,1-tris(acetyloxy)-1,1-dihydro-1, 2-benziodoxol-3-(1H)-one | |

-continued

| Abbreviations | |
|---|---|
| COMU: (1-cyano-2-ethoxy-2-oxoethylidenaminooxy) dimethylamino-morpholino-carbenium hexafluorophosphate | |
| h: hour | r.t.: room temperature |
| M: mass | RT: retention time |
| HPLC: High Performance Liquid Chromatography | |
| LCMS: Liquid Chromatography Mass Spectrometry | |
| ES+: Electrospray Positive Ionisation | |

Analytical Conditions

All NMR spectra were obtained at 300 MHz, 400 MHz or 500 MHz.

All reactions involving air- or moisture-sensitive reagents were performed under a nitrogen atmosphere using dried solvents and glassware.

LCMS Data Determination

Method 1
Agilent Technologies 1260 Infinity

| Part | Model |
|---|---|
| LC/MSD | G6130B |
| Degasser | G4225A |
| BinPump | G1312B |
| HiP ALS (autosampler) | G1367E |
| Valve Drive | G1170A |
| TCC | G1316A |
| DAD VL | G1315D |
| Interface | 5900E |

Apparatus

Agilent 1260 Bin. Pump: G1312B, degasser; autosampler, ColCom. DAD: Agilent G1315D, 220-320 nm. MSD: Agilent LC/MSD G6130B ESI, pos/neg 100-800, ELSD Alltech 3300.

Gas flow: 1.5 mL/minute; Gas temp.: 40° C.; Column: Waters XSelect™ C18, 30×2.1 mm, 3.5 μm; Temperature: 35° C.; Flow: 1 mL/minute; Gradient: $t_0$=5% A, $t_{1.6min}$=98% A, $t_{3.0min}$=98% A; Post-time: 1.3 minutes; Eluent A: 0.1% formic acid in acetonitrile; Eluent B: 0.1% formic acid in water.

Method 2
Agilent Technologies 1260 Infinity

| Part | Model |
|---|---|
| Degasser | G4225A |
| Binary pump | G1312B |
| Sampler, 1260HipALS | G1367E |
| Column comp | G1316A |
| DAD | G1315C |
| MSD | G6130B |
| Valve | G1170A |

Apparatus

Agilent 1260 Bin. Pump: G1312B, degasser; autosampler, ColCom. DAD: Agilent G1315C, 220-320 nm. MSD: Agilent LC/MSD G6130B ESI, pos/neg 100-800.

Column: Waters XSelect™ CSH C18, 30×2.1 mm, 3.5 μm; Temperature: 25° C.; Flow: 1 mL/minute, Gradient: $t_0$=5% A, $t_{1.6min}$=98% A, $t_{3min}$=98% A; Post-time: 1.3 minutes; Eluent A: 95% acetonitrile+5% 10 mM ammonium bicarbonate in water in acetonitrile; Eluent B: 10 mM ammonium bicarbonate in water (pH 9.5).

Method 3
Agilent Technologies 1260 Infinity

| Part | Model |
|---|---|
| LC/MSD | G6130B |
| Degasser | G4225A |
| BinPump | G1312B |
| HiP ALS (autosampler) | G1367E |
| Valve Drive | G1170A |
| TCC | G1316A |
| DAD VL | G1315D |
| Interface | 5900E |

Apparatus

Agilent 1260 Bin. Pump: G1312B, degasser; autosampler, ColCom. DAD: Agilent G1315D, 220-320 nm. MSD: Agilent LC/MSD G6130B ESI, pos/neg 100-800, ELSD Alltech 3300.

Gas flow 1.5 mL/minute; Gas temp.: 40° C.; Column: Waters XSelect™ C18, 50×2.1 mm, 3.5 μm; Temperature: 35° C.; Flow: 0.8 mL/minute; Gradient: $t_0$=5% A, $t_{3.5min}$=98% A, $t_{6.0min}$=98% A; Post-time: 2.0 minutes; Eluent A: 0.1% formic acid in acetonitrile; Eluent B: 0.1% formic acid in water.

Method 4

Column: X-Bridge C18 Waters 2.1×20 mm, 2.5 μm column

Mobile Phase A: 10 mM ammonium formate in water+0.1% ammonia solution

Mobile Phase B: acetonitrile+5% water+0.1% ammonia solution

Gradient program: Flow rate pump 1: 1 mL/min; Flow rate pump 2: 0.5 mL/min

| Pump 1: | | | Pump 2: | | |
|---|---|---|---|---|---|
| Time | A % | B % | Time | A % | B % |
| 0.00 | 95.10 | 4.90 | 0.10 | 5.00 | 95.00 |
| 4.00 | 5.00 | 95.00 | 1.00 | 5.00 | 95.00 |
| 5.00 | 5.00 | 95.00 | 1.10 | 95.00 | 5.00 |
| 5.10 | 95.10 | 4.90 | | | |

Method 5

Column: X-Bridge C18 Waters 2.1×20 mm, 2.5 μm column

Mobile Phase A: 10 mM ammonium formate in water+0.1% formic acid

Mobile Phase B: acetonitrile+5% water+0.1% formic acid

Gradient program: Flow rate pump 1: 1 mL/min; Flow rate pump 2: 0.5 mL/min

| Pump 1: | | | Pump 2: | | |
|---|---|---|---|---|---|
| Time | A % | B % | Time | A % | B % |
| 0.00 | 95.00 | 5.00 | 0.10 | 5.00 | 95.00 |
| 4.00 | 5.00 | 95.00 | 1.00 | 5.00 | 95.00 |
| 5.00 | 5.00 | 95.00 | 1.10 | 95.00 | 5.00 |
| 5.10 | 95.00 | 5.00 | | | |

Method 6
Agilent Technologies 1260 Infinity

| Part | Model |
|---|---|
| LC/MSD | G6130B |
| Degasser | G4225A |

-continued

| Part | Model |
|---|---|
| BinPump | G1312B |
| HiP ALS (autosampler) | G1367E |
| Valve Drive | G1170A |
| TCC | G1316A |
| DAD VL | G1315D |
| Interface | 5900E |

Apparatus

Agilent 1260 Bin. Pump: G1312B, degasser; autosampler, ColCom. DAD: Agilent G1315D, 220-320 nm. MSD: Agilent LC/MSD G6130B ESI, pos/neg 100-800, ELSD Alltech 3300.

Gas flow 1.5 mL/minute; Gas temp.: 40° C.; Column: Waters XSelect™ C18, 30×2.1 mm, 3.5 μm; Temperature: 35° C.; Flow: 1 mL/minute; Gradient: $t_0$=5% A, $t_{1.6min}$=98% A, $t_{3.0min}$=98% A; Post-time: 1.3 minutes; Eluent A: 0.1% formic acid in acetonitrile; Eluent B: 0.1% formic acid in water.

Method 7

Column: Kinetex Core-Shell C18, 50×2.1 mm, 5 μm column protected by Phenomenex 'Security Guard' column Mobile Phase A: 0.1% formic acid in water Mobile Phase B: 0.1% formic acid in acetonitrile Gradient program: Flow rate 1.2 mL/minute Column temperature: 40° C.

| Time | A % | B % |
|---|---|---|
| 0.00 | 95 | 5 |
| 1.20 | 0 | 100 |
| 1.30 | 0 | 100 |
| 1.31 | 95 | 5 |

Method 8

Column: Phenomenex Gemini-NX C18, 2.0 mm×50 mm, 3 μm column

Mobile Phase A: 2 mM ammonium bicarbonate, pH 10

Mobile Phase B: acetonitrile

Gradient program: Flow rate 1.0 mL/minute

Column temperature: 40° C.

| Time | A % | B % |
|---|---|---|
| 0.00 | 99 | 1 |
| 1.80 | 0 | 100 |
| 2.10 | 0 | 100 |
| 2.30 | 99 | 1 |
| 3.50 | 99 | 1 |

GCMS Data Determination

Method 9

Agilent Technologies

| Part | Model |
|---|---|
| 5973 MSD | G2577A |
| Autosampler | G2614A |
| 7683B injector | G2913A |
| 6890N GC system | G1530N |

Instrument: GC: Agilent 6890N, FID: Detection temp.: 300° C. and MS: 5973 MSD, EI-positive, Detection temp.: 280° C.; Mass range: 50-550; Column: RXi-5MS 20 m, ID 180 μm, df 0.18 μm; Average velocity: 50 cm/s; Injection vol.: 1 μL; Injector temp.: 250° C.; Split ratio: 20/1; Carrier gas: He; Initial temperature: 100° C.; Initial time: 1.5 minutes; Solvent delay: 1.3 minutes; Rate: 75° C./minute; Final temp.: 250° C.; Final time: 2.5 minutes.

Intermediate 1

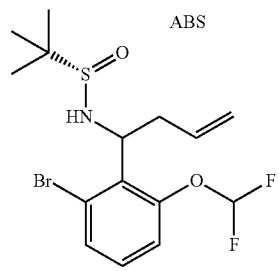

(S)—N-{1-[2-Bromo-6-(difluoromethoxy)phenyl]but-3-en-1-yl}-2-methylpropane-2-sulfinamide Prepared in accordance with WO 2016/050975, Intermediate 83.

Intermediate 2

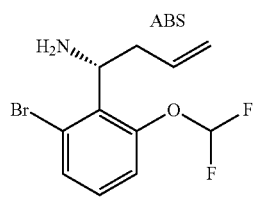

(1R)-1-[2-Bromo-6-(difluoromethoxy)phenyl]but-3-en-1-amine

Under a nitrogen atmosphere at 0° C., 4M hydrogen chloride in 1,4-dioxane (40 mL) was added to a solution of Intermediate 1 (95.5:4.5 (S):(R) mixture, d.e. 91%, 19.5 g, 49.2 mmol) in MeOH (30 mL). The reaction mixture was allowed to warm to r.t., then stirred for 3 h and concentrated in vacuo. The residue was taken up in 1M aqueous hydrochloric acid solution (100 mL) and extracted with diethyl ether (2×50 mL). The combined organic layers were washed with 1M aqueous hydrochloric acid solution (25 mL). The combined acidic water layers were basified with potassium carbonate and extracted with diethyl ether (2×50 mL). The organic extracts were combined and washed with brine (25 mL), then dried ($Na_2SO_4$), filtered and concentrated in vacuo. The crude residue (14.8 g, 95% pure) was dissolved in 2-propanol (65 mL) and (S)-2-hydroxy-2-phenylacetic acid (7.30 g, 48.0 mmol) was added. The resulting thick suspension was diluted with n-heptane (65 mL) and warmed to reflux, then allowed to cool to r.t. and crystallise over the weekend. The crystals were collected by filtration, washed three times with a mixture of heptane and 2-propanol (1:1), then dried under air on the filter. The crystals were partitioned between DCM (75 mL) and 2M aqueous NaOH solution (75 mL). The aqueous layer was separated and extracted with DCM (25 mL). The combined organic layers were washed with 2M aqueous NaOH solution (20 mL) and brine (20 mL), then dried ($Na_2SO_4$), filtered and concentrated in vacuo, to afford the title compound (11.0 g, 77%) as a colourless oil. $\delta_H$ (400 MHz, CDCl$_3$) 7.41 (dd, J 7.8, 1.3 Hz, 1H), 7.12-6.98 (m, 2H), 6.56 (t, J 73.5 Hz, 1H), 5.77 (ddt, J 14.4, 10.0, 7.2 Hz, 1H), 5.14-4.94 (m, 2H), 4.59 (t, J 7.6 Hz, 1H), 2.61 (t, J 7.2 Hz, 2H), 1.83 (s, 2H).

Intermediate 3

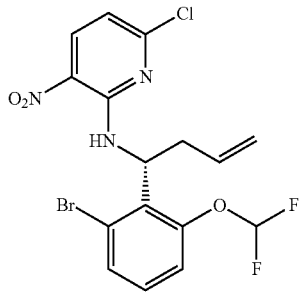 [SMILES: C=CC[C@@H](Nc1nc(Cl)ccc1[N+](=O)[O-])c1c(Br)cccc1OC(F)F]

N-{(1R)-1-[2-Bromo-6-(difluoromethoxy)phenyl] but-3-en-1-yl}-6-chloro-3-nitropyridin-2-amine Under a nitrogen atmosphere, a mixture of Intermediate 2 (10.9 g, 37.3 mmol), 2,6-dichloro-3-nitropyridine (7.20 g, 37.3 mmol) and triethylamine (5.98 mL, 42.9 mmol) was dissolved in DCM (50 mL) and stirred over the weekend. The reaction mixture was diluted with DCM and 1M aqueous hydrochloric acid solution. The layers were separated and the aqueous phase was extracted three times with DCM. The combined organic layers were washed sequentially with 1M aqueous hydrochloric acid solution and water, then dried (Na$_2$SO$_4$), filtered and concentrated in vacuo. The residue was purified by flash column chromatography on silica (gradient elution with 5-20% EtOAc in n-heptane) to afford the title compound (15.7 g, 94%) as a yellow oil. LCMS [M+H]$^+$ 448/450/452, RT 2.41 minutes (Method 1).

Intermediate 4

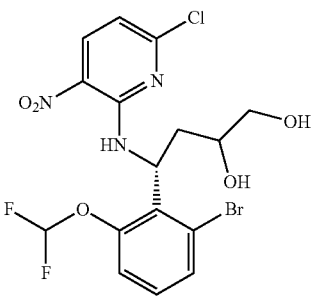 [SMILES: O=[N+]([O-])c1ccc(Cl)nc1N[C@H](CC(O)CO)c1c(Br)cccc1OC(F)F]

(4R)-4-[2-Bromo-6-(difluoromethoxy)phenyl]-4-[(6-chloro-3-nitropyridin-2-yl)amino]-butane-1,2-diol At 0° C., 4-methylmorpholine-4-oxide (50 wt % in water, 14.2 mL, 68.7 mmol), followed by osmium tetroxide (4 wt % in water, 6.29 mL, 1.03 mmol), were added to a solution of Intermediate 3 (15.4 g, 34.3 mmol) in THF (340 mL). The mixture was stirred overnight at r.t., then diluted with 10% aqueous sodium thiosulfate solution and extracted three times with EtOAc. The combined organic layers were washed sequentially with 10% aqueous sodium thiosulfate solution and water, then dried (Na$_2$SO$_4$), filtered and concentrated in vacuo, to afford the title compound (17.1 g) as a yellow oil, which was utilised without further purification. LCMS [M+H]$^+$ 482/484/486, RT 2.09 minutes (Method 2).

Intermediate 5

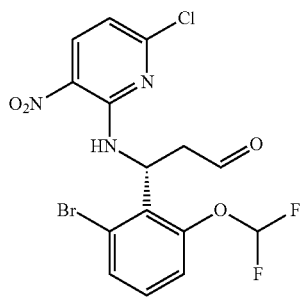 [SMILES: O=CC[C@@H](Nc1nc(Cl)ccc1[N+](=O)[O-])c1c(Br)cccc1OC(F)F]

(3R)-3-[2-Bromo-6-(difluoromethoxy)phenyl]-3-[(6-chloro-3-nitropyridin-2-yl)amino]-propanal To a solution of Intermediate 4 in a mixture of THF (170 mL) and water (60 mL), cooled to 0° C., was added sodium periodate (3.67 g, 17.2 mmol). The reaction mixture was allowed to warm to r.t. After 1 h, a second portion of sodium periodate (3.67 g, 17.2 mmol) was added; and after another 2 h, a third portion of sodium periodate (7.34 g, 34.3 mmol) was added. The reaction mixture was stirred overnight. The phases were separated and the aqueous phase was extracted with EtOAc (3×100 mL). The combined organic layers were washed sequentially with saturated aqueous sodium hydrogen carbonate solution and water, then dried (Na$_2$SO$_4$), filtered and concentrated in vacuo. The residue was purified by flash column chromatography on silica (gradient elution with 5-50% EtOAc in n-heptane) to afford the title compound (11.4 g, 77%) as a yellow solid. $\delta_H$ (400 MHz, CDCl$_3$) 9.82 (s, 1H), 9.17 (d, J 8.4 Hz, 1H), 8.33 (d, J 8.6 Hz, 1H), 7.46 (dd, J 7.4, 1.7 Hz, 1H), 7.21-7.11 (m, 2H), 6.81-6.73 (m, 1H), 6.74 (t, J 72.6 Hz, 1H), 6.65 (d, J 8.6 Hz, 1H), 3.41-3.29 (m, 1H), 3.04 (dd, J 16.9, 5.1 Hz, 1H). LCMS [M+H]$^+$ 450/452/454, RT 2.28 minutes (Method 2).

Intermediate 6

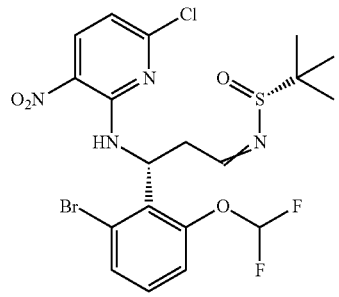 [SMILES: CC(C)(C)[S@@](=O)N=CC[C@@H](Nc1nc(Cl)ccc1[N+](=O)[O-])c1c(Br)cccc1OC(F)F]

(R)—N-{(3R)-3-[2-Bromo-6-(difluoromethoxy) phenyl]-3-[(6-chloro-3-nitropyridin-2-yl)-amino] propylidene}-2-methylpropane-2-sulfinamide Under an argon atmosphere, titanium(IV) ethoxide (85% pure, 12.07 mL, 48.6 mmol) was added to a solution of Intermediate 5 (10.1 g, 22.4 mmol) and (R)-(+)-tert-butylsulfinamide (2.82 g, 23.3 mmol) in DCM (90 mL). The reaction mixture was stirred over the weekend, then concentrated in vacuo. The residue was suspended in acetonitrile (100 mL), then water (1.35 mL, 74.7 mmol) was added. After swirling for a few minutes, the mixture was filtered and washed with acetonitrile, followed by DCM. The combined filtrates were concentrated in vacuo. The residue was purified by flash column chromatography on silica (gradient elution with 50% EtOAc in n-heptane) to afford the title compound (10.9 g, 88%) as a yellow foam. $\delta_H$ (400 MHz, CDCl$_3$) 9.18 (br d, J 8.5 Hz, 1H), 8.31 (d, J 8.6 Hz, 1H), 8.10 (dd, J 5.1, 3.9 Hz, 1H), 7.45 (dd, J 7.2, 1.9 Hz, 1H), 7.20-7.10 (m, 2H), 6.73 (t, J 72.7 Hz, 1H), 6.71-6.64 (m, 1H), 6.63 (d, J 8.6 Hz, 1H), 3.55-3.39 (m, 1H), 3.11 (dt, J 16.3, 4.3 Hz, 1H), 1.12 (s, 9H). LCMS [M+Na]$^+$ 575/577/579, [M−H]$^−$ 551/553/555, RT 2.28 minutes (Method 1).

Intermediate 7

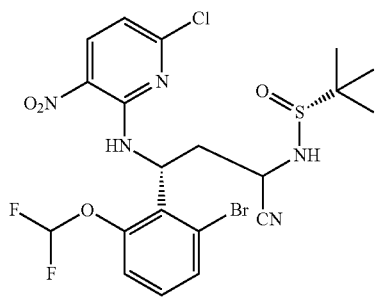 [SMILES: CC(C)(C)[S@@](=O)NC(C#N)C[C@@H](Nc1nc(Cl)ccc1[N+](=O)[O-])c1c(Br)cccc1OC(F)F]

(R)—N-{(3R)-3-[2-Bromo-6-(difluoromethoxy)phenyl]-3-[(6-chloro-3-nitropyridin-2-yl)-amino]-1-cyanopropyl}-2-methylpropane-2-sulfinamide Intermediate 6 (10.9 g, 19.7 mmol) was co-evaporated twice from DCM. The residue was dissolved in DCM (79 mL) and scandium triflate (1.94 g, 3.94 mmol) was added. The reaction mixture was sealed and trimethylsilyl cyanide (5.42 mL, 43.3 mmol) was added. The mixture was stirred for 3 days, then concentrated in vacuo (aqueous sodium hypochlorite/NaOH scavenger was used to neutralise any condensing trimethylsilyl cyanide) and co-evaporated twice from DCM. The residue was purified by flash column chromatography on silica (gradient elution with 30-100% EtOAc in heptane) to afford the title compound (~4:1 mixture of stereoisomers) (9.66 g) as a yellow foam. $\delta_H$ (400 MHz, CDCl$_3$) 9.46-9.04 (m, 1H), 8.37 (d, J 8.6 Hz, 1H), 7.49-7.42 (m, 1H), 7.24-7.11 (m, 2H), 6.80 (t, J 72.2 Hz, 0.2H), 6.75 (dd, J 73.4, 71.5 Hz, 0.8H), 6.69 (dd, J 8.6, 2.0 Hz, 1H), 6.56-6.46 (m, 1H), 4.52-4.44 (m, 0.2H), 4.31 (td, J 9.5, 3.9 Hz, 0.8H), 3.99-3.89 (m, 1H), 3.00-2.65 (m, 0.8H), 2.58-2.47 (m, 0.2H), 2.44 (ddd, J 14.0, 9.8, 3.8 Hz, 1H), 1.28 (s, 9H). LCMS [M+H]$^+$ 580/582/584, RT 2.16 minutes (Method 1).

Intermediate 8

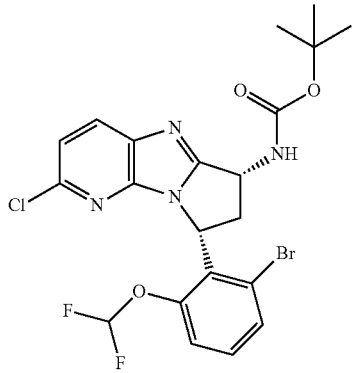 [SMILES: CC(C)(C)OC(=O)N[C@@H]1C[C@H](c2c(Br)cccc2OC(F)F)n2c1nc1ccc(Cl)nc12]

tert-Butyl {(6R,8R)-8-[2-bromo-6-(difluoromethoxy)phenyl]-2-chloro-7,8-dihydro-6H-pyrrolo[2′,1′:2,3]imidazo[4,5-b]pyridin-6-yl}carbamate Under a nitrogen atmosphere, zinc bromide (1.53 g, 6.79 mmol), and platinum (10 wt % on activated carbon, 1.62 g, 0.83 mmol) were added to a solution of Intermediate 7 (10.4 g, 16.6 mmol) in EtOAc (100 mL). The reaction mixture was flushed with hydrogen and stirred under a hydrogen atmosphere overnight. The reaction mixture was flushed with nitrogen, filtered over kieselguhr and rinsed with EtOAc. The combined filtrates were washed with water and brine, then dried (Na$_2$SO$_4$), filtered and concentrated in vacuo, to afford a dark solid (mixture of stereoisomers), which was utilised without further purification. $\delta_H$ (400 MHz, CDCl$_3$) 7.48-7.34 (m, 1H), 7.19-6.42 (m, 5H), 6.33-6.05 (m, 1H), 6.03-5.17 (m, 1H), 4.68-4.32 (m, 2H), 3.90-2.50 (m, 3H), 2.46-2.26 (m, 1H), 1.28 (s, 9H). LCMS [M+H]$^+$ 550/552/554, RT 2.07 minutes (Method 1).

The crude residue was dissolved in ethanol (110 mL) and added to 5 microwave vials in equal portions. To each vial was added sulfuric acid (0.53 mL, 10.0 mmol). The reaction mixtures were sealed and stirred at 120° C. for 3 h, then cooled to r.t. The reaction mixtures were combined, diluted with saturated aqueous sodium hydrogen carbonate solution (250 mL) and extracted with DCM (3×250 mL). The combined extracts were dried (Na$_2$SO$_4$), filtered and concentrated in vacuo to afford a dark green oil, which was utilised without further purification. LCMS [M+H]$^+$ 429/431/433, RT 1.559 minutes (Method 1).

Di-tert-butyl dicarbonate (5.47 g, 25.1 mmol) was added to a solution of the foregoing crude material in DCM (134 mL). After 2 days, the reaction mixture was concentrated in vacuo and the residue was purified twice by flash column chromatography on silica (gradient elution with 20-60% EtOAc in n-heptane). The relevant fractions were combined, then concentrated in vacuo and dissolved in EtOAc. Activated charcoal (0.6 g) was added. After 0.5 h, the mixture was filtered over kieselguhr and washed with EtOAc. The combined filtrates were concentrated in vacuo to afford the title compound (3:2 mixture of atropisomers) (2.24 g, 25%) as a brown solid. $\delta_H$ (400 MHz, CDCl$_3$) 7.93 (d, J 8.4 Hz, 0.6H), 7.91 (d, J 8.4 Hz, 0.4H), 7.57 (d, J 8.1 Hz, 1H), 7.40 (dd, J 6.7, 2.4 Hz, 0.4H), 7.31-7.22 (m, 1H), 7.16 (d, J 8.4 Hz, 0.6H), 7.15 (d, J 8.4 Hz, 0.4H), 6.96 (d, J 8.3 Hz, 0.6H), 6.74 (dd, J 75.5, 70.6 Hz, 0.4H), 6.25 (t, J 8.2 Hz, 0.4H), 6.17 (t, J 8.0 Hz, 0.6H), 5.83 (dd, J 76.5, 69.6 Hz, 0.6H), 5.63-5.43 (m, 1H), 5.44 (d, J 7.6 Hz, 0.4H), 5.36 (d, J 7.3 Hz, 0.6H), 3.77-3.56 (m, 1H), 2.79 (dt, J 16.3, 8.3 Hz, 0.4H), 2.54 (dt, J 13.6, 8.0 Hz, 0.6H), 1.49 (s, 9H). LCMS [M+H]$^+$ $^{529/531/533}$, RT 2.13 minutes (Method 1).

Intermediate 9

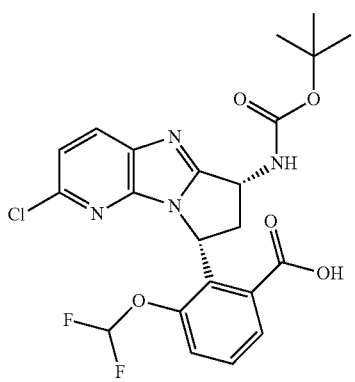 [SMILES: CC(C)(C)OC(=O)N[C@@H]1C[C@H](c2c(OC(F)F)cccc2C(=O)O)n2c1nc1ccc(Cl)nc12]

2-{(6R,8R)-6-[(tert-Butoxycarbonyl)amino]-2-chloro-7,8-dihydro-6H-pyrrolo[2',1':2,3]-imidazo[4,5-b]pyridin-8-yl}-3-(difluoromethoxy)benzoic Acid In a glass autoclave, Intermediate 8 (1.50 g, 2.83 mmol) and potassium carbonate (0.587 g, 4.25 mmol) were dissolved in a mixture of DMSO (56 mL) and water (255 µL, 14.16 mmol). Argon was bubbled through the mixture for 10 minutes, then 1,4-bis-(diphenylphosphino)butane-palladium (II) chloride (0.171 g, 0.283 mmol) was added and the autoclave was closed. The vessel was pressurised with carbon monoxide (2 bar) and placed in an oil bath at 100° C. After 2 h, the autoclave was cooled to r.t. and flushed with nitrogen. The reaction mixture was diluted with water (150 mL), then the suspension was filtered through a layer of kieselguhr and rinsed with water. The combined filtrates were acidified with aqueous citric acid solution (1M, ~25 mL) and extracted with EtOAc (3×150 mL). The combined organic layers were washed twice with brine, then dried (Na$_2$SO$_4$), filtered and concentrated in vacuo. The residue was triturated with acetonitrile (10 mL) and filtered. The solids were washed with further acetonitrile. The combined filtrates were concentrated in vacuo, then the crude residue was purified by reverse phase flash column chromatography on C-18 silica (gradient elution with 20-100% acetonitrile in water [each containing 0.1% (v/v) formic acid]) to afford the title compound (426 mg, 30%) as a white solid. δ$_H$ (400 MHz, CDCl$_3$) 7.74 (d, J 7.6 Hz, 1H), 7.51 (t, J 8.0 Hz, 1H), 7.42 (d, J 8.3 Hz, 1H), 7.12-7.03 (m, 2H), 6.86 (d, J 8.2 Hz, 1H), 6.71 (dd, J 74.6, 71.3 Hz, 1H), 6.24 (t, J 8.1 Hz, 1H), 5.55 (q, J 8.2 Hz, 1H), 3.71-3.60 (m, 1H), 3.07-2.96 (m, 1H), 1.28 (s, 9H); the acidic proton was detected as a very broad singlet at 14.7 ppm. LCMS [M+H]$^+$ 495/497, RT 2.01 minutes (Method 1).

Intermediate 10

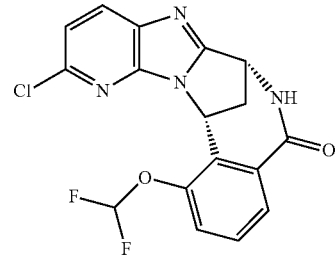 [SMILES: O=C1N[C@@H]2C[C@H](c3c(OC(F)F)cccc31)n1c2nc2ccc(Cl)nc21]

(7R,14R)-11-Chloro-1-(difluoromethoxy)-6,7-dihydro-7,14-methanopyrido[3',2':4,5]-imidazo[1,2-b][2,5]benzodiazocin-5(14H)-one To a solution of Intermediate 9 (400 mg, 0.808 mmol) in 1,4-dioxane (8 mL) was added 4M hydrochloric acid in 1,4-dioxane (4 mL, 16 mmol). After 4 h, the reaction mixture was concentrated in vacuo to afford 2-[(6R,8R)-6-amino-2-chloro-7,8-dihydro-6H-pyrrolo[2',1':2,3]imidazo[4,5-b]pyridin-8-yl]-3-(difluoromethoxy)benzoic acid hydrochloride (1:1), which was utilised without further purification. LCMS [M+H]$^+$ 395/397, RT 1.51 minutes (Method 1).

COMU (380 mg, 0.888 mmol) and N-methylmorpholine (0.444 ml, 4.04 mmol) were added to a suspension of the foregoing material in DMF (16 mL). The reaction mixture was stirred for 1 h, then diluted with water and extracted twice with EtOAc. The combined organic phases were washed three times with brine, then dried (Na$_2$SO$_4$), filtered and concentrated in vacuo. The residue was purified by flash column chromatography on silica (gradient elution with 0-10% MeOH in DCM) to afford the title compound (275 mg) as a light brown oil that solidified on standing. δ$_H$ (400 MHz, CDCl$_3$) 8.41 (d, J 8.0 Hz, 1H), 7.93 (d, J 8.4 Hz, 1H), 7.55-7.48 (m, 1H), 7.44 (t, J 8.1 Hz, 1H), 7.20 (d, J 8.4 Hz, 1H), 7.14-7.01 (br s, 1H), 7.13 (dd, J 81.3, 67.0 Hz, 1H), 6.55 (d, J 7.4 Hz, 1H), 4.93 (t, J 6.6 Hz, 1H), 3.46 (dt, J 13.5, 7.0 Hz, 1H), 2.87 (d, J 13.5 Hz, 1H). LCMS [M+H]$^+$ 377/379, RT 1.87 minutes (Method 1).

Intermediate 11

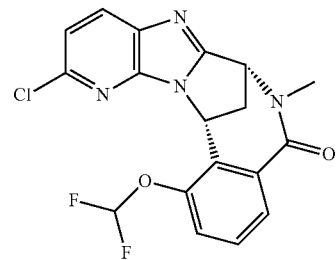 [SMILES: CN1C(=O)c2cccc(OC(F)F)c2[C@H]2C[C@@H]1c1nc3ccc(Cl)nc3n12]

(7R,14R)-11-Chloro-1-(difluoromethoxy)-6-methyl-6,7-dihydro-7,14-methanopyrido-[3',2':4,5]imidazo[1,2-b][2,5]benzodiazocin-5(14H)-one Under nitrogen at 0° C., sodium hydride (60 wt % dispersion in mineral oil, 47 mg, 1.18 mmol) was added in small portions to a solution of Intermediate 10 (275 mg, 0.73 mmol) in DMF (3.3 mL). After stirring for 15 minutes, iodomethane (82 µL, 1.32 mmol) was added and the reaction mixture was allowed to warm to r.t. After stirring for 3 h, additional iodomethane (82 μL, 0.32 mmol) and sodium hydride (60 wt % dispersion in mineral oil, 10 mg, 0.25 mmol) were added and stirring was continued for 2 h. The reaction mixture was quenched by the addition of brine, then diluted with water and extracted twice with EtOAc. The combined organic phases were washed three times with brine, then dried (Na$_2$SO$_4$) and concentrated in vacuo. The crude residue was purified by flash column chromatography on silica (gradient elution with 0-10% MeOH in DCM) to afford the title compound (195 mg, 61%). δ$_H$ (400 MHz, CDCl$_3$) 8.47 (dd, J 7.6, 1.8 Hz, 1H), 7.91 (d, J 8.4 Hz, 1H), 7.49-7.38 (m, 2H), 7.19 (d, J 8.5 Hz, 1H), 7.11 (dd, J 81.4, 67.3 Hz, 1H), 6.46 (d, J 7.4 Hz, 1H), 4.96 (d, J 7.1 Hz, 1H), 3.49 (s, 3H), 3.44 (dt, J 14.3, 7.3 Hz, 1H), 2.88 (d, J 13.6 Hz, 1H). LCMS [M+H]$^+$ 391/393, RT 1.93 minutes (Method 1).

Intermediate 12

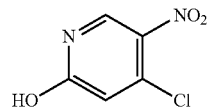

4-Chloro-5-nitropyridin-2-ol

Prepared according to the procedure reported in EP-A-2818472, paragraph [0127].

Intermediate 13

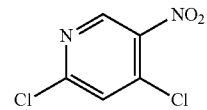 [SMILES: O=[N+]([O-])c1cnc(Cl)cc1Cl]

2,4-Dichloro-5-nitropyridine

Prepared from Intermediate 12 according to the procedure reported in EP-A-2818472, paragraph [0128].

Intermediate 14

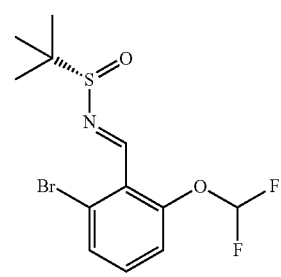 [SMILES: CC(C)(C)[S@](=O)/N=C/c1c(Br)cccc1OC(F)F]

(S)—N-{(E/Z)-[2-Bromo-6-(difluoromethoxy)phenyl]methylidene}-2-methylpropane-2-sulfinamide To a stirred solution of THF (133.5 kg) at 10-20° C. was added 2-bromo-6-(difluoromethoxy)benzaldehyde (30 kg, 119.5 mol) at 10-20° C. (S)-(−)-2-Methyl-2-propanesulfinamide (15.9 kg, 131.46 mol) was added, followed by slow addition of titanium(IV) ethoxide (40.89 kg, 179.27 mol) at 10-35° C. The reaction mixture was stirred at 30-40° C. for 18 h. Water (42.9 kg) and EtOAc (270.6 kg) were added, followed by celatom (9.0 kg). The filter cake and the filtrate were obtained, and the filter cake was washed with EtOAc (2×405.9 kg). The filtrates were combined, then washed with water (128.7 kg) and brine (128.7 kg). The organic layer was concentrated in vacuo to afford the title compound (40.5 kg, 96%) as a brown oil, which was utilised without further purification.

Intermediate 15

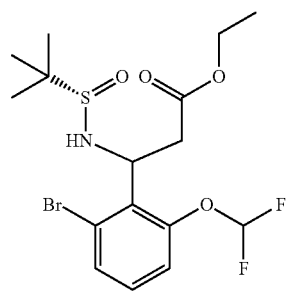 [SMILES: CCOC(=O)CC(N[S@@](=O)C(C)(C)C)c1c(Br)cccc1OC(F)F]

Ethyl 3-[2-bromo-6-(difluoromethoxy)phenyl]-3-{[(S)-tert-butylsulfinyl]amino}-propanoate To a stirred solution of THF (324.4 kg) at 15-20° C. were added zinc (52.33 kg, 800.37 mmol) and copper(I) chloride (16.98 kg, 171.51 mmol). The reaction mixture was warmed to 60-70° C. under nitrogen and was stirred for 1-2 h. The reaction mixture was cooled to 20-30° C. and ethyl 2-bromoacetate (47.74 kg, 285.85 mol) was added within 2-4 h at 20-30° C. under nitrogen. The reaction mixture was stirred at 50-60° C. for 1-2 h under nitrogen, then cooled to 0-10° C. Intermediate 14 (40.5 kg, 114.33 mol) in THF (36.05 kg) was added at 0-10° C. under nitrogen. The reaction mixture was warmed to 20-30° C., then stirred at 20-30° C. for 1-2 h under nitrogen. To the reaction mixture were added MTBE (179.82 kg) and a solution of citric acid (40.5 kg) in water (243 kg). The layers were separated and the aqueous layer was extracted with MTBE (179.82 kg). The organic layers were combined, then washed with water (101.25 kg), saturated aqueous sodium hydrogen carbonate solution (243 kg) and brine (101.25 kg). The organic layer was concentrated in vacuo to afford the title compound (47.0 kg, 93%) as a brown oil, which was utilised without further purification.

Intermediate 16

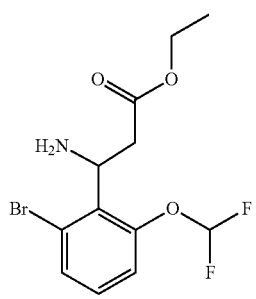 [SMILES: CCOC(=O)CC(N)c1c(Br)cccc1OC(F)F]

Ethyl 3-amino-3-[2-bromo-6-(difluoromethoxy)phenyl]propanoate

To a stirred solution of Intermediate 15 (47.0 kg, 106.26 mol) in EtOAc (42.39 kg) at 15-20° C. was added 4M hydrochloric acid/EtOAc (100 kg) at 15-25° C. The mixture was stirred at 20° C. for 1 h under nitrogen, then water (117.5 kg) was added and the aqueous layer was separated. The organic layer was further extracted with water (4×117.5 kg) and the aqueous layers were adjusted to pH 8-9 with sodium carbonate (47.0 kg). The aqueous layer was extracted with EtOAc (2×254.36 kg), then the organic layers were combined, washed with brine (117.5 kg), separated and concentrated in vacuo, to afford the title compound (34 kg, 95%) as a brown oil.

Intermediate 17

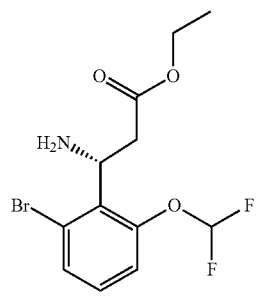

Ethyl (3R)-3-amino-3-[2-bromo-6-(difluoromethoxy)phenyl]propanoate

Intermediate 16 (34 kg, 100.50 mol) was added to MTBE (150.96 kg) at 15-20° C. and the resulting solution was warmed to 50-60° C. under nitrogen. To the mixture was added (S)-mandelic acid (15.3 kg, 100.55 mol) in portions. The mixture was stirred for 1-2 h, then cooled to 10-20° C. The filter cake and filtrate were separated. To the filter cake was added MTBE (62.9 kg) at 15-20° C. The mixture was stirred for 0.5 h, then filtered. To the filter cake was added water (340 kg), and the aqueous layer was adjusted to pH 8-9 with sodium hydrogen carbonate (34 kg). The aqueous layer was extracted with EtOAc (2×184 kg), then the organic layers were combined and washed with brine (68 kg). The organic layer was concentrated in vacuo to afford the title compound (22.0 kg, 65%) as a brown oil, which was utilised without further purification.

Intermediate 18

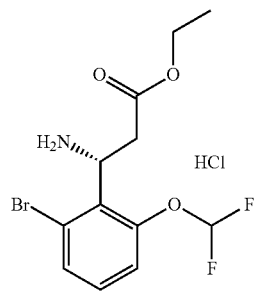 [SMILES: CCOC(=O)C[C@@H](N)c1c(Br)cccc1OC(F)F ; Cl]

Ethyl (3R)-3-amino-3-[2-bromo-6-(difluoromethoxy)phenyl]propanoate Hydrochloride (1:1)

To MTBE (8.14 kg) at 15-20° C. was added 3M hydrochloric acid in MTBE (18.6 kg) at 15-25° C. To this solution was added Intermediate 17 (11 kg) and the reaction mixture was stirred for 2 h. The filter cake and filtrate were separated, and to the filter cake was added MTBE (16.28 kg). The mixture was stirred for 0.5 h, then filtered, to provide the title compound (11.35 kg, 93%) as a white solid.

Intermediate 19

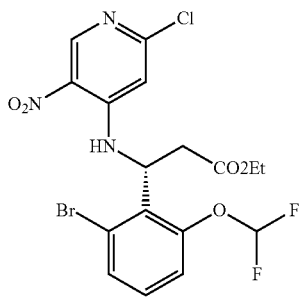 [SMILES: CCOC(=O)C[C@@H](Nc1cc(Cl)ncc1[N+](=O)[O-])c1c(Br)cccc1OC(F)F]

Ethyl (3R)-3-[2-bromo-6-(difluoromethoxy)phenyl]-3-[(2-chloro-5-nitropyridin-4-yl)-amino]propanoate At 0° C., Intermediate 18 (204 g, 544 mmol) was added portionwise to a solution of Intermediate 13 (100 g, 518 mmol) and triethylamine (216 mL, 1.56 mol) in THF (1 L). After the addition was complete, the mixture was allowed to warm to r.t. and stirred overnight. Additional triethylamine (36 mL, 259 mmol) was added and stirring was continued for another day, then the reaction mixture was concentrated in vacuo. The residue was diluted with EtOAc and water, then the layers were separated. The aqueous layer was extracted twice with EtOAc. The combined organic layers were washed twice with water, then dried ($Na_2SO_4$), filtered and concentrated in vacuo. The residue was diluted with diethyl ether and washed three times with 1M aqueous potassium hydrogen sulfate solution, followed by water. The organic layer was dried ($Na_2SO_4$) and filtered, then concentrated in vacuo, to afford the title compound (222 g, 87%) as a brown oil. $\delta_H$ (400 MHz, $CDCl_3$) 9.08 (d, J 8.8 Hz, 1H), 9.00 (s, 1H), 7.50 (dd, J 7.9, 1.3 Hz, 1H), 7.25 (t, J 8.1 Hz, 1H), 7.19 (d, J 8.2 Hz, 1H), 7.03 (s, 1H), 6.71 (t, J 72.1 Hz, 1H), 5.92-5.82 (m, 1H), 4.18 (q, J 7.1 Hz, 2H), 3.36-3.19 (m, 1H), 2.94 (dd, J 16.0, 4.5 Hz, 1H), 1.26 (t, J 7.1 Hz, 3H). LCMS $[M+H]^+$ 494/496/498, RT 2.37 minutes (Method 1).

Intermediate 20

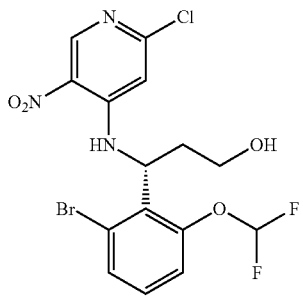 [SMILES: O=[N+]([O-])c1cnc(Cl)cc1N[C@H](CCO)c1c(Br)cccc1OC(F)F]

(3R)-3-[2-Bromo-6-(difluoromethoxy)phenyl]-3-[(2-chloro-5-nitropyridin-4-yl)amino]-propan-1-ol Under an argon atmosphere at 0° C., diisobutylaluminium hydride (1M in hexanes, 425 mL, 425 mmol) was added dropwise to a solution of Intermediate 19 (100 g, 202 mmol) in THF (1 L) over 2 h, maintaining the internal temperature below 3° C. After 1 h, additional diisobutylaluminium hydride (1M in hexanes, 40 mL, 40 mmol) was added, and stirring was continued for 15 minutes. The reaction mixture was poured onto sodium sulfate decahydrate (293 g, 910 mmol) and stirred for 5 minutes until a thick slurry was formed. The mixture was diluted with EtOAc and stirred for 30 minutes, then filtered over kieselguhr. The filtrate was concentrated in vacuo to afford the title compound (89.3 g, 87%) as a brown sticky oil that solidified upon standing. δ$_H$ (400 MHz, CDCl$_3$) 9.05 (br s, 1H), 8.98 (s, 1H), 7.48 (dd, J 7.9, 1.0 Hz, 1H), 7.21 (t, J 8.1 Hz, 1H), 7.18-7.09 (m, 1H), 6.90 (br s, 1H), 6.62 (t, J 72.0 Hz, 1H), 5.56 (q, J 8.5 Hz, 1H), 3.85-3.73 (m, 2H), 2.48-2.14 (m, 2H), 1.57 (br s, 1H). LCMS [M+H]$^+$ 452/454/456, RT 2.23 minutes (Method 1).

acetonitrile (1 L) were added. The residue was stirred for 20 minutes, then filtered over kieselguhr (no vacuum applied). The filter cake was rinsed with EtOAc, and the combined filtrates were concentrated in vacuo. The residue was purified by flash column chromatography on silica (gradient elution with 0-3% MeOH in DCM) to afford the title compound (127 g, 62%) as a yellow foam. δ$_H$ (400 MHz, CDCl$_3$) 9.07-8.93 (m, 1H), 8.98 (s, 1H), 8.11 (dd, J 4.6, 3.1 Hz, 1H), 7.50 (dd, J 8.0, 1.2 Hz, 1H), 7.25 (t, J 8.2 Hz, 1H), 7.18 (br d, J 8.3 Hz, 1H), 6.96 (br s, 1H), 6.70 (t, J 72.1 Hz, 1H), 5.92 (td, J 9.4, 4.1 Hz, 1H), 3.66-3.45 (br s, 1H), 3.08 (dt, J 17.2, 3.5 Hz, 1H), 1.17 (s, 9H). LCMS [M+H]$^+$ 553/555/557, RT 2.25 minutes (Method 1).

Intermediate 21

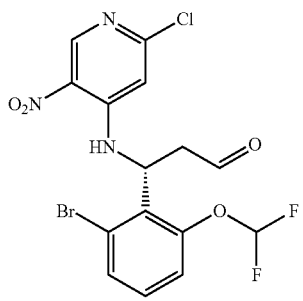 [SMILES: O=CC[C@@H](Nc1cc(Cl)ncc1[N+](=O)[O-])c1c(Br)cccc1OC(F)F]

(3R)-3-[2-Bromo-6-(difluoromethoxy)phenyl]-3-[(2-chloro-5-nitropyridin-4-yl)amino]-propanal At 0° C., Dess-Martin periodinane (171 g, 403 mmol) was added to a solution of Intermediate 20 (166 g, 366 mmol) in DCM (1.5 L). The mixture was allowed to warm to r.t., then stirred for 1 h. Aqueous sodium thiosulfate solution (10%, 1.5 L) was added and the mixture was stirred for 3 h. The organic layer was separated, then added to saturated aqueous sodium hydrogen carbonate solution and stirred overnight. The layers were separated. The organic layer was washed with saturated aqueous sodium hydrogen carbonate solution (twice) and water, then dried (Na$_2$SO$_4$), filtered and concentrated in vacuo, to afford the title compound (165 g, 100%) as a brown sticky oil, which was utilised without further purification. δ$_H$ (400 MHz, CDCl$_3$) 9.80 (s, 1H), 9.03-8.90 (m, 1H), 8.99 (s, 1H), 7.49 (dd, J 8.0, 1.2 Hz, 1H), 7.24 (t, J 8.2 Hz, 1H), 7.17 (br d, J 8.1 Hz, 1H), 7.06 (s, 1H), 6.71 (t, J 72.1 Hz, 1H), 5.96 (td, J 9.0, 4.4 Hz, 1H), 3.56 (dd, J 18.4, 8.9 Hz, 1H), 3.10 (br d, J 17.4 Hz, 1H).

Intermediate 22

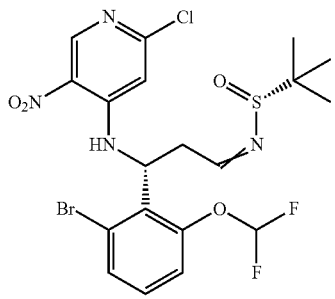 [SMILES: CC(C)(C)[S@@](=O)N=CC[C@@H](Nc1cc(Cl)ncc1[N+](=O)[O-])c1c(Br)cccc1OC(F)F]

(R)—N-{(3R)-3-[2-Bromo-6-(difluoromethoxy)phenyl]-3-[(2-chloro-5-nitropyridin-4-yl)-amino]propylidene}-2-methylpropane-2-sulfinamide Titanium(IV) isopropoxide (216 mL, 732 mmol) was added to a solution of Intermediate 21 (165 g, 366 mmol) and (R)-(+)-2-methyl-2-propanesulfinamide (53.3 g, 439 mmol) in DCM (1 L). The mixture was stirred overnight, then concentrated in vacuo. Water (26 mL, 1.47 mol) and Intermediate 23

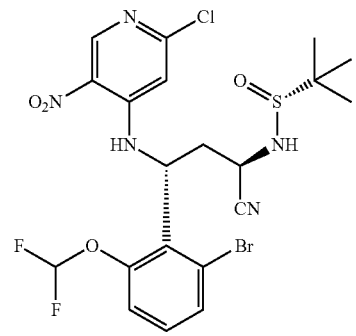 [SMILES: CC(C)(C)[S@@](=O)N[C@@H](C#N)C[C@@H](Nc1cc(Cl)ncc1[N+](=O)[O-])c1c(Br)cccc1OC(F)F]

(R)—N-{(1R,3R)-3-[2-Bromo-6-(difluoromethoxy)phenyl]-3-[(2-chloro-5-nitropyridin-4-yl)amino]-1-cyanopropyl}-2-methylpropane-2-sulfinamide To a solution of Intermediate 22 (55 g, 99 mmol) in DCM (550 mL) was added scandium triflate (3.85 g, 19.9 mmol). The reaction mixture was sealed and trimethylsilyl cyanide (25 mL, 200 mmol) was added. The mixture was stirred for 7 days, then concentrated in vacuo (aqueous sodium hypochlorite/NaOH scavenger mixture was used to neutralise any condensing trimethylsilyl cyanide). The residue was taken up in DCM, washed with 2M aqueous NaOH solution (twice), water, and brine, then dried (Na$_2$SO$_4$), filtered and concentrated in vacuo, to afford the title compound (50.3 g, 87%) as a yellow foam, which was utilised without further purification. δ$_H$ (400 MHz, CDCl$_3$) 9.20-8.84 (m, 1H), 9.01 (s, 1H), 7.50 (dd, J 8.0, 0.9 Hz, 1H), 7.30-7.14 (m, 2H), 6.99-6.50 (m, 2H), 5.60 (br s, 1H), 4.30 (td, J 9.7, 4.4 Hz, 1H), 3.99 (d, J 9.7 Hz, 1H), 2.84 (br s, 1H), 2.41 (br s, 1H), 1.26 (s, 9H). LCMS [M+H]$^+$ 580/582/584, RT 2.26 minutes (Method 1).

Intermediate 24

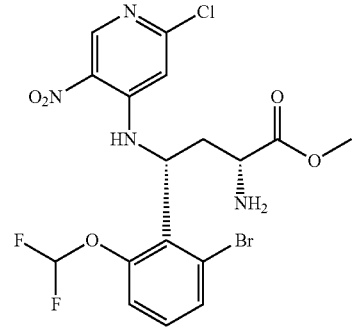 [SMILES: COC(=O)[C@H](N)C[C@@H](Nc1cc(Cl)ncc1[N+](=O)[O-])c1c(Br)cccc1OC(F)F]

Methyl (2R,4R)-2-amino-4-[2-bromo-6-(difluoromethoxy)phenyl]-4-[(2-chloro-5-nitro-pyridin-4-yl)amino]butanoate At 0° C., 35% hydrochloric acid (100 mL, 3.24 mol) was added to Intermediate 23 (56.9 g, 98 mmol). After 30 minutes, the cooling bath was removed. The reaction mixture was stirred at r.t. for 3 h, then cooled in an ice/water bath. Aqueous NaOH solution (3M) was added carefully until the reaction mixture became basic. The reaction mixture was extracted with a 9:1 mixture of DCM and MeOH (3×500 mL). The combined organic layers were washed with brine and dried ($Na_2SO_4$), then filtered and concentrated in vacuo, to afford a yellow foam, which was utilised without further purification. $\delta_H$ (400 MHz, $CDCl_3$) 9.04 (br s, 1H), 8.99 (s, 1H), 7.48 (d, J 7.6 Hz, 1H), 7.25-7.12 (m, 2H), 7.04-6.41 (m, 3H), 5.64 (td, J 9.3, 4.1 Hz, 1H), 5.52 (br s, 1H), 3.50 (ddt, J 11.5, 7.7, 3.9 Hz, 1H), 2.74 (br s, 1H), 2.07-1.95 (m, 1H), 1.55 (d, J 7.6 Hz, 2H). LCMS $[M+H]^+$ 494/496/498, RT 1.94 minutes (Method 1).

To a solution of the foregoing crude material in MeOH (500 mL) was carefully added sulfuric acid (30 mL, 563 mmol). The resulting mixture was stirred at 70° C. for 6 h, then at r.t. overnight. The mixture was concentrated in vacuo to ~30% of the original volume, then poured into saturated aqueous sodium carbonate solution (800 mL) and extracted with EtOAc (3×750 mL). The combined organic layers were washed with brine and dried ($Na_2SO_4$), then filtered and concentrated in vacuo. The residue was purified by flash column chromatography on silica (gradient elution with 30-100% EtOAc in heptane) to afford the title compound (24.3 g, 45%) as a yellow oil. $\delta_H$ (400 MHz, $CDCl_3$) 9.17 (m, 1H), 8.99 (s, 1H), 7.47 (d, J 8.0 Hz, 1H), 7.20 (t, J 8.1 Hz, 1H), 7.15 (br d, J 8.2 Hz, 1H), 7.06 (s, 1H), 6.66 (t, J 72.1 Hz, 1H), 5.82 (td, J 9.7, 3.7 Hz, 1H), 3.72 (s, 3H), 3.56 (dd, J 10.5, 3.4 Hz, 1H), 2.77-2.51 (br s, 1H), 2.01-1.81 (m, 1H), 1.59 (s, 2H). LCMS $[M+H]^+$ 509/511/513, RT 2.14 minutes (Method 2).

Intermediate 25

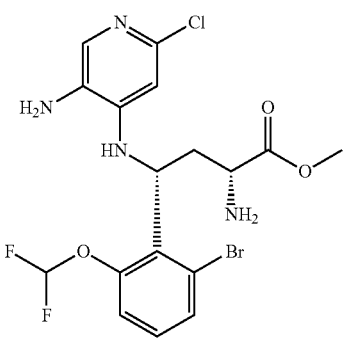

Methyl (2R,4R)-2-amino-4-[(5-amino-2-chloropyridin-4-yl)amino]-4-[2-bromo-6-(difluoromethoxy)phenyl]butanoate Tin(II) chloride (21.0 g, 111 mmol) was added to a solution of Intermediate 24 (24.3 g, 44.3 mmol) in MeOH (500 mL). The resulting suspension was warmed to 60° C. and stirred for 3.5 h. Additional tin(II) chloride (5 g, 26.4 mmol) was added and stirring was continued for another 2 h, then the reaction mixture was allowed to cool to r.t. Aqueous potassium fluoride solution (10%, 150 mL) was added. The resulting mixture was stirred overnight, then filtered over a plug of kieselguhr and rinsed with DCM. The combined filtrates were separated and the aqueous phase was extracted with DCM (3×400 mL). The aqueous phase was basified with saturated aqueous sodium carbonate solution, then saturated with sodium chloride and extracted with EtOAc (3×400 mL). The combined organic layers were washed with brine and dried ($Na_2SO_4$), then filtered and concentrated in vacuo. The residue was purified by flash column chromatography on silica (gradient elution with 5% MeOH in DCM) to afford the title compound (15 g, 71%) as a light foam. $\delta_H$ (400 MHz, $CDCl_3$) 7.61 (s, 1H), 7.46 (d, J 8.0 Hz, 1H), 7.15 (t, J 8.2 Hz, 1H), 7.10-6.98 (m, 1H), 6.75-6.25 (m, 2H), 5.80 (d, J 9.2 Hz, 1H), 5.57-5.44 (m, 1H), 3.72 (d, J 3.9 Hz, 1H), 3.70 (s, 3H), 3.10 (s, 2H), 2.51 (br s, 1H), 1.95 (ddd, J 13.7, 9.4, 3.7 Hz, 1H), 1.65 (s, 2H). LCMS $[M+H]^+$ 479/481/483, RT 1.91 minutes (Method 2).

Intermediate 26

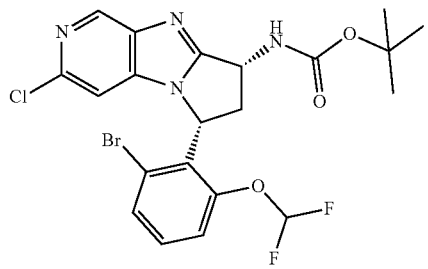 [SMILES: CC(C)(C)OC(=O)N[C@@H]1C[C@H](c2c(Br)cccc2OC(F)F)n2c1nc1cnc(Cl)cc12]

tert-Butyl {(6R,8R)-6-[2-bromo-6-(difluoromethoxy)phenyl]-3-chloro-7,8-dihydro-6H-pyrrolo[1',2':1,2]imidazo[4,5-c]pyridin-8-yl}carbamate Intermediate 25 (14.9 g, 31.1 mmol) was co-evaporated twice from toluene, then dissolved in toluene (250 mL) under a nitrogen atmosphere. The mixture was cooled to 0° C. and sodium tert-butoxide (4.48 g, 46.6 mmol) was added in one portion. After 1 h, the reaction mixture was poured into saturated aqueous ammonium chloride solution (500 mL) and extracted with EtOAc (3×300 mL). During the extraction a solid formed, which was dissolved by the addition of MeOH. The combined organic layers were washed with brine and dried ($Na_2SO_4$), then filtered and concentrated in vacuo, to afford a brown solid (10.7 g), which was utilised without further purification. LCMS $[M+H]^+$ 429/431/433, RT 1.83 minutes (Method 2).

To a solution of the foregoing crude material (10.7 g) in DCM (250 mL) was added di-tert-butyl dicarbonate (8.15 g, 37.4 mmol). After stirring over the weekend, the reaction mixture was concentrated in vacuo. The residue was purified by flash column chromatography on silica (gradient elution with 30-65% EtOAc in heptane) to afford the title compound (3:2 mixture of atropisomers) (4.6 g, 28%) as a light orange foam. $\delta_H$ (400 MHz, $CDCl_3$) 8.78 (s, 1H), 7.62 (d, J 8.1 Hz, 0.6H), 7.51-7.44 (m, 0.4H), 7.38-7.30 (m, 1.4H), 7.01 (d, J 8.3 Hz, 0.6H), 6.70 (t, J 72.3 Hz, 0.4H), 6.61 (s, 0.6H), 6.56

(s, 0.4H), 6.18 (td, J 8.2, 3.7 Hz, 1H), 5.95 (dd, J 74.9, 70.5 Hz, 0.6H), 5.55 (p, J 8.5 Hz, 1H), 5.40 (dd, J 18.0, 7.5 Hz, 1H), 3.71 (dt, J 13.6, 8.6 Hz, 0.6H), 3.61 (dt, J 13.5, 8.5 Hz, 0.4H), 2.84 (dt, J 13.5, 8.7 Hz, 0.4H), 2.71 (dt, J 13.7, 7.8 Hz, 0.6H), 1.50 (s, 9H). LCMS [M+H]⁺ 529/531/533, RT 2.14 minutes (Method 2).

Intermediate 27

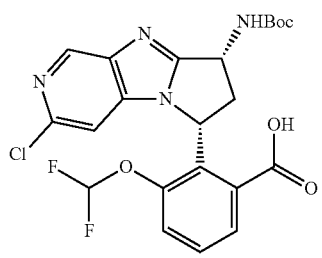 [SMILES: CC(C)(C)OC(=O)N[C@@H]1C[C@H](c2c(OC(F)F)cccc2C(=O)O)n2c1nc1cnc(Cl)cc12]

2-{(6R,8R)-8-[(tert-Butoxycarbonyl)amino]-3-chloro-7,8-dihydro-6H-pyrrolo[1',2':1,2]-imidazo[4,5-c]pyridin-6-yl}-3-(difluoromethoxy)benzoic Acid In a glass autoclave, Intermediate 26 (1.5 g, 2.83 mmol) and potassium carbonate (0.626 g, 4.53 mmol) were dissolved in a mixture of DMSO (15 mL) and water (500 µL). Argon was bubbled through the mixture for 5 minutes. 1,4-Bis(diphenylphosphino)-butane-palladium(II) chloride (0.085 g, 0.142 mmol) was added and the autoclave was closed. The vessel was pressurised with carbon monoxide (2 bar) and placed in an oil bath at 80° C. After 3.5 h, the reaction mixture was allowed to cool to r.t., then flushed with nitrogen and diluted with water (40 mL). The resulting suspension was filtered over a plug of kieselguhr, and the filter was rinsed several times with water. The combined filtrates were acidified with 1M aqueous citric acid solution until pH ~5, then extracted with EtOAc (2×200 mL). The combined organic layers were washed with brine and dried (Na₂SO₄), then filtered and concentrated in vacuo, to afford the title compound (~7:3 mixture of atropisomers) (910 mg, 65%) as a colourless oil, which was utilised without further purification. An analytical sample was obtained after preparative reverse phase chromatography (Reveleris Prep; Column: Phenomenex Luna C18, 150×25 mm, 10µ; Flow: 40 mL/minute; Gradient: t₀=5% B, t₁ₘᵢₙ=5% B, t₁₆ₘᵢₙ=40% B, t₁₇ₘᵢₙ=100% B, t₂₂ₘᵢₙ=100% B; Eluent A: 0.1% (v/v) formic acid in water; Eluent B: 0.1% (v/v) formic acid in acetonitrile). δ_H (400 MHz, DMSO-d₆) 14.17-12.61 (br s, 1H), 8.67 (s, 1H), 7.69 (d, J 7.7 Hz, 0.7H), 7.63-7.53 (m, 1.3H), 7.50 (d, J 7.3 Hz, 0.3H), 7.39 (t, J 72.5 Hz, 0.3H), 7.38-7.30 (m, 1.4H), 6.79 (t, J 72.3 Hz, 0.7H), 6.70 (s, 0.3H), 6.54 (s, 0.7H), 6.36 (d, J 9.7 Hz, 0.3H), 6.21 (t, J 8.1 Hz, 0.7H), 6.10 (t, J 8.1 Hz, 0.3H), 5.48 (q, J 8.8 Hz, 0.7H), 5.54-5.36 (m, 0.3H), 3.48 (dt, J 12.4, 9.2 Hz, 0.3H), 3.40-3.25 (m, 0.7H), 2.74-2.62 (m, 1H), 1.47 (s, 9H). LCMS [M+H]⁺ 495/497, RT 1.95 minutes (Method 1).

Intermediate 28

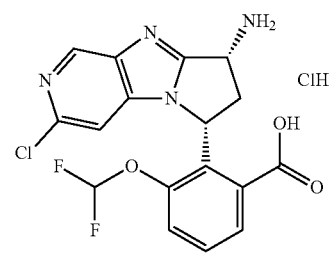 [SMILES: N[C@@H]1C[C@H](c2c(OC(F)F)cccc2C(=O)O)n2c1nc1cnc(Cl)cc12 ; Cl]

2-[(6R,8R)-8-Amino-3-chloro-7,8-dihydro-6H-pyrrolo[1',2':1,2]imidazo[4,5-c]pyridin-6-yl]-3-(difluoromethoxy)benzoic Acid Hydrochloride (1:1)

To a solution of Intermediate 27 (2.80 g, 5.66 mmol) in 1,4-dioxane (30 mL) was added 4M hydrochloric acid in 1,4-dioxane (20 mL, 80.0 mmol). The reaction mixture was stirred overnight, then concentrated in vacuo and co-evaporated twice with diethyl ether, to afford the title compound (2.44 g, 100%) as an off-white solid, which was utilised without further purification. LCMS [M+H]⁺ 395/397, RT 1.42 minutes (Method 1).

Intermediate 29

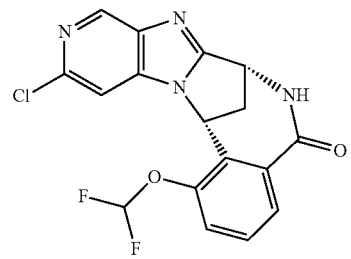 [SMILES: O=C1N[C@@H]2C[C@H](c3c(OC(F)F)cccc31)n1c2nc2cnc(Cl)cc21]

(7R,14R)-11-Chloro-1-(difluoromethoxy)-6,7-dihydro-7,14-methanopyrido[3',4':4,5]-imidazo[1,2-b][2,5]benzodiazocin-5(14H)-one COMU (2.67 g, 6.23 mmol) was added to a solution of crude Intermediate 28 (2.44 g, 5.66 mmol) and N-methylmorpholine (3.11 mL, 28.3 mmol) in DMF (30 mL). After stirring for 1.5 h, the reaction mixture was diluted with water (200 mL) and extracted with EtOAc (2×250 mL). The combined organic layers were washed twice with brine and dried (Na₂SO₄), then filtered and concentrated in vacuo. The residue was purified by flash column chromatography on silica (gradient elution with 4-6% MeOH in DCM) to afford the title compound (640 mg, 30%) as a white solid. δ_H (400 MHz, DMSO-d₆) 9.18 (d, J 6.9 Hz, 1H), 8.73 (s, 1H), 8.24 (dd, J 6.6, 2.8 Hz, 1H), 7.61 (t, J 73.2 Hz, 1H), 7.58-7.49 (m, 2H), 7.39 (s, 1H), 6.34 (d, J 7.2 Hz, 1H), 4.93 (t, J 6.8 Hz, 1H), 3.46 (dt, J 13.7, 7.0 Hz, 1H), 2.77 (d, J 13.5 Hz, 1H). LCMS [M+H]⁺ 377/379, RT 1.74 minutes (Method 1).

Intermediate 30

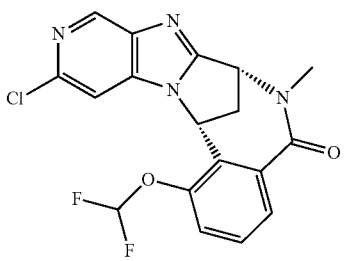 [SMILES: CN1C(=O)c2cccc(OC(F)F)c2[C@H]2C[C@@H]1c1nc3cnc(Cl)cc3n12]

(7R,14R)-11-Chloro-1-(difluoromethoxy)-6-methyl-6,7-dihydro-7,14-methanopyrido-[3',4':4,5]imidazo[1,2-b][2,5]benzodiazocin-5(14H)-one Intermediate 29 (300 mg, 0.796 mmol) was added in one portion to a suspension of sodium hydride (60% dispersion in mineral oil, 47.8 mg, 1.194 mmol) in DMF (7 mL). After stirring for 15 minutes, iodomethane (0.10 mL, 1.593 mmol) was added. The reaction mixture was stirred for 45 minutes, then quenched with water (100 mL) and extracted with EtOAc (2×75 mL). The combined organic layers were washed twice with brine, then dried (Na$_2$SO$_4$), filtered and concentrated in vacuo. The residue was purified by flash column chromatography on silica (gradient elution with 2-5% MeOH in DCM) to afford the title compound (230 mg, 74%) as a white solid. $\delta_H$ (400 MHz, DMSO-d$_6$) 8.75 (s, 1H), 8.32-8.25 (m, 1H), 7.61 (t, J 73.2 Hz 1H), 7.57-7.49 (m, 2H), 7.40 (s, 1H), 6.28 (d, J 7.2 Hz, 1H), 5.29 (d, J 7.1 Hz, 1H), 3.50 (dt, J 14.3, 7.3 Hz, 1H), 3.34 (s, 3H), 2.86 (d, J 13.9 Hz, 1H). LCMS [M+H]$^+$ 391/393, RT 1.79 minutes (Method 1).

Intermediate 31

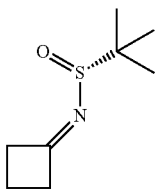

(R)—N-Cyclobutylidene-2-methylpropane-2-sulfinamide

Under a nitrogen atmosphere, titanium(IV) ethoxide (215 mL, 1.02 mol) was added to a solution of cyclobutanone (50 g, 713 mmol) and (R)-(+)-2-methyl-2-propanesulfinamide (82 g, 679 mmol) in THF (1.36 L). After stirring over the weekend, the reaction mixture was concentrated in vacuo. The residue was taken up in EtOAc (1 L) and saturated aqueous sodium hydrogen carbonate solution (0.5 L) was added. The resulting thick suspension was filtered over kieselguhr and washed with EtOAc (1 L). The combined filtrates were washed with brine and dried (Na$_2$SO$_4$), then filtered and concentrated in vacuo. The residue was purified by flash column chromatography on silica (gradient elution with 25-35% EtOAc in n-heptane) to afford the title compound (83.5 g, 71%) as a sticky yellow solid. $\delta_H$ (400 MHz, CDCl$_3$) 3.59-3.40 (m, 1H), 3.35-3.21 (m, 1H), 3.21-3.02 (m, 2H), 2.11 (p, J 8.2 Hz, 2H), 1.24 (s, 9H).

Intermediate 32

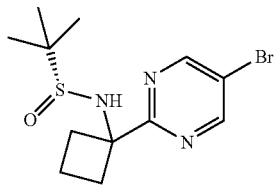 [SMILES: CC(C)(C)[S@@](=O)NC1(c2ncc(Br)cn2)CCC1]

(R)—N-[1-(5-Bromopyrimidin-2-yl)cyclobutyl]-2-methylpropane-2-sulfinamide

Under a nitrogen atmosphere at −78° C., n-butyllithium (2.5M in hexanes, 182 mL, 455 mmol) was added dropwise to a solution of 5-bromo-2-iodopyrimidine (129 g, 452 mmol) in DCM (3.0 L) over 15 minutes. After 20 minutes, a solution of Intermediate 31 (77.5 g, 447 mmol) in DCM (300 mL) was added dropwise over 30 minutes. The reaction mixture was stirred at −78° C. and allowed to warm gradually to −20° C. overnight, then poured into an ice/water mixture (1 L). The layers were separated and the aqueous phase was extracted with DCM (2×1 L). The combined organic layers were dried (Na$_2$SO$_4$), filtered and concentrated in vacuo. The residue was purified by flash column chromatography on silica (gradient elution with 15-60% EtOAc in n-heptane) to afford the title compound (39 g, 26%) as a yellow oil. $\delta_H$ (400 MHz, CDCl$_3$) 8.77 (s, 2H), 4.78 (s, 1H), 2.88-2.78 (m, 1H), 2.73-2.55 (m, 2H), 2.54-2.43 (m, 1H), 2.14-1.92 (m, 2H), 1.24 (s, 9H). LCMS [M+H]$^+$ 332/334, RT 1.857 minutes, 93.0% purity (Method 1).

Intermediate 33

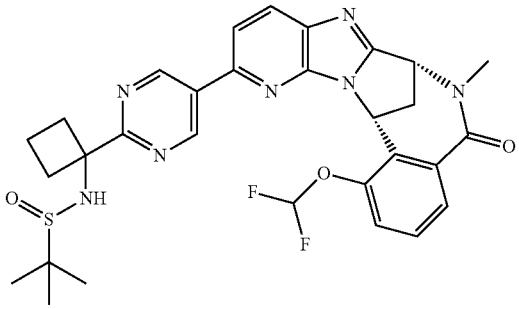 [SMILES: CN1C(=O)c2cccc(OC(F)F)c2[C@H]2C[C@@H]1c1nc3ccc(-c4cnc(C5(NS(=O)C(C)(C)C)CCC5)nc4)nc3n12]

(R)—N-(1-{5-[(7R,14R)-1-(Difluoromethoxy)-6-methyl-5-oxo-5,6,7,14-tetrahydro-7,14-methanopyrido[3',2':4,5]imidazo[1,2-b][2,5]benzodiazocin-11-yl]pyrimidin-2-yl}-cyclobutyl)-2-methylpropane-2-sulfinamide Argon was bubbled through a mixture of Intermediate 32 (222 mg, 0.667 mmol), potassium acetate (149 mg, 1.516 mmol) and bis(pinacolato)diboron (185 mg, 0.728 mmol) in 1,4-dioxane (5 mL). After addition of 2-dicyclohexylphosphino-2',4',6'-triisopropylbiphenyl (28.9 mg, 0.061 mmol) and tris(dibenzylideneacetone)dipalladium(0) (27.8 mg, 0.030 mmol), the reaction vial was closed. The reaction mixture was stirred at 110° C. for 1 h, then cooled to r.t. Water (1.25 mL), Intermediate 11 (237 mg, 0.606 mmol) and potassium phosphate (193 mg, 0.910 mmol) were added. Argon was bubbled through the mixture for 10 minutes, then [1,1'-bis(diphenylphosphino)ferrocene]dichloro-palladium (II) (22.2 mg, 0.030 mmol) was added. The reaction mixture was closed and stirred at 110° C. for 1 h, prior to the addition of further [1,1'-bis(diphenylphosphino)-ferrocene]dichloropalladium(II) (22.2 mg, 0.030 mmol). The reaction mixture was stirred at 110° C. overnight, then cooled to r.t., and diluted with water and EtOAc. The phases were separated and the aqueous phase was extracted with EtOAc. The combined organic phases were dried ($Na_2SO_4$), filtered and concentrated in vacuo. The crude residue was purified by flash column chromatography on silica (gradient elution with 0-10% MeOH in DCM) to afford the title compound (300 mg, 81%) as a beige solid. $\delta_H$ (400 MHz, $CDCl_3$) 9.27 (s, 2H), 8.47 (dd, J 6.5, 3.0 Hz, 1H), 8.09 (d, J 8.4 Hz, 1H), 7.64 (d, J 8.4 Hz, 1H), 7.45-7.36 (m, 2H), 7.02 (dd, J 78.1, 69.1 Hz, 1H), 6.54 (d, J 7.3 Hz, 1H), 5.05 (s, 1H), 5.00 (d, J 7.0 Hz, 1H), 3.57-3.43 (m, 1H), 3.52 (s, 3H), 2.91 (d, J 13.6 Hz, 1H), 2.82-2.69 (m, 2H), 2.62-2.48 (m, 1H), 2.18-1.97 (m, 3H), 1.27 (s, 9H). LCMS [M+H]+ 608, RT 1.93 minutes (Method 1).

Intermediate 34

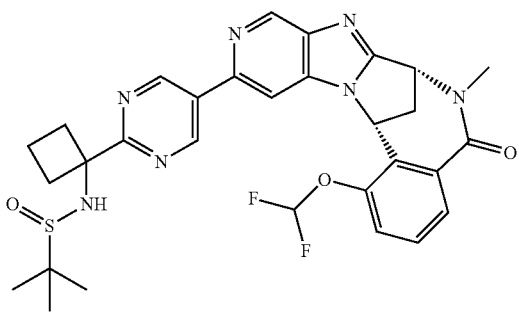 [SMILES: CN1C(=O)c2cccc(OC(F)F)c2[C@H]2C[C@@H]1c1nc3cnc(-c4cnc(C5(NS(=O)C(C)(C)C)CCC5)nc4)cc3n12]

(R)—N-(1-{5-[(7R,14R)-1-(Difluoromethoxy)-6-methyl-5-oxo-5,6,7,14-tetrahydro-7,14-methano-pyrido[3',4':4,5]imidazo[1,2-b][2,5]benzodiazocin-11-yl]pyrimidin-2-yl}-cyclobutyl)-2-methylpropane-2-sulfinamide Argon was bubbled through a mixture of Intermediate 32 (145 mg, 0.435 mmol), potassium acetate (107 mg, 1.088 mmol) and bis(pinacolato)diboron (133 mg, 0.522 mmol) in 1,4-dioxane (4 mL) for 10 minutes. After addition of 2-dicyclohexylphosphino-2',4',6'-triisopropylbiphenyl (20.7 mg, 0.044 mmol) and tris(dibenzylideneacetone)dipalladium(0) (19.9 mg, 0.022 mmol), the reaction vial was closed. The reaction mixture was stirred at 110° C. for 90 minutes, then cooled to r.t. Water (1 mL), Intermediate 30 (170 mg, 0.435 mmol) and potassium phosphate (139 mg, 0.653 mmol) were added. Argon was bubbled through the mixture for 10 minutes, then [1,1'-bis-(diphenylphosphino)ferrocene]dichloropalladium(II) (15.9 mg, 0.022 mmol) was added. The reaction mixture was sealed and stirred at 110° C. for 1 h, then cooled to r.t., and diluted with water and EtOAc. The layers were separated and the aqueous phase was extracted with EtOAc (2×50 mL). The combined organic layers were washed with water and dried ($Na_2SO_4$), then filtered and concentrated in vacuo. The residue was purified by flash column chromatography on silica (gradient elution with 0-5% MeOH in DCM) to afford the title compound (174 mg, 66%) as an off-white solid. $\delta_H$ (400 MHz, $CDCl_3$) 9.32 (s, 2H), 9.13-9.09 (m, 1H), 8.52 (d, J 7.5 Hz, 1H), 7.88-7.84 (m, 1H), 7.47 (t, J 8.2 Hz, 1H), 7.36 (d, J 8.0 Hz, 1H), 6.90 (t, J 72.7 Hz, 1H), 6.32 (d, J 7.2 Hz, 1H), 5.03 (s, 1H), 5.00 (d, J 7.1 Hz, 1H), 3.57-3.44 (m, 1H), 3.56 (s, 3H), 2.95 (d, J 13.7 Hz, 1H), 2.94-2.84 (m, 1H), 2.82-2.66 (m, 2H), 2.60-2.50 (m, 1H), 2.17-1.99 (m, 2H), 1.26 (s, 9H). LCMS [M+H]+ 608, RT 1.86 minutes (Method 1).

Intermediate 35

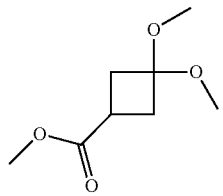

Methyl 3,3-dimethoxycyclobutanecarboxylate

Methyl 3-oxocyclobutanecarboxylate (45 g, 394 mmol), trimethyl orthoformate (259 mL, 2.37 mol) and p-toluenesulfonic acid monohydrate (7.50 g, 39.4 mmol) were combined in MeOH (500 mL). The solution was heated at reflux for 2 h with stirring, then cooled to r.t. and concentrated in vacuo. The residue was dissolved in diethyl ether (500 mL) and washed with saturated aqueous sodium hydrogen carbonate solution (500 mL). The aqueous phase was extracted with diethyl ether (500 mL). The combined organic layers were washed with brine and dried ($Na_2SO_4$), then filtered and concentrated in vacuo, to afford the title compound (74.4 g). $\delta_H$ (400 MHz, $CDCl_3$) 3.70 (s, 3H), 3.17 (s, 3H), 3.15 (s, 3H), 2.94-2.83 (m, 1H), 2.48-2.34 (m, 4H).

Intermediate 36

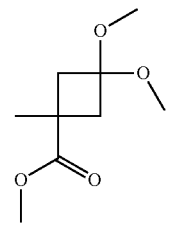

Methyl 3,3-dimethoxy-1-methylcyclobutanecarboxylate n-Butyllithium in hexanes (2.5M, 133 mL, 332 mmol) was added to a cooled solution of diisopropylamine (56 mL, 398 mmol) in THF (1 L) at −78° C. The mixture was stirred for 15 minutes prior to the dropwise addition of Intermediate 35 (68 g, 332 mmol) in THF (50 mL). The reaction mixture was stirred for 30 minutes prior to the dropwise addition of iodomethane (41 mL, 664 mmol), which caused the internal temperature to increase to −60° C. The reaction mixture was stirred at −78° C. for 30 minutes, then warmed to ambient temperature. The reaction mixture was poured into saturated aqueous ammonium chloride solution (1 L) and extracted with diethyl ether (2×500 mL). The combined organic layers were washed with brine and dried ($Na_2SO_4$), then filtered and concentrated in vacuo. The crude residue (64.7 g) was purified by flash column chromatography on silica (gradient elution with 10-40% EtOAc in heptane) to afford the title compound (52.5 g). $\delta_H$ (400 MHz, $CDCl_3$) 3.71 (s, 3H), 3.16 (s, 3H), 3.13 (s, 3H), 2.67-2.58 (m, 2H), 2.10-2.01 (m, 2H), 1.44 (s, 3H).

Intermediate 37

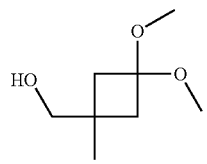

(3,3-Dimethoxy-1-methylcyclobutyl)methanol

To a solution of Intermediate 36 (42 g, 224 mmol) in THF (800 mL), cooled in an ice bath, was added 2.4M lithium aluminium hydride solution in THF (94 mL, 235 mmol). The reaction mixture was stirred at r.t. for 60 minutes. Water (8 mL) was added dropwise, followed by 10% aqueous sodium hydroxide solution (8 mL). To the suspension was added water (24 mL) and the mixture was stirred. Sodium sulphate was added and the granular suspension was filtered. The filtrate was rinsed with diethyl ether, and the combined filtrate was concentrated in vacuo, to afford the title compound (38 g, 15%) as a light oil. $\delta_H$ (400 MHz, $CDCl_3$) 3.50 (d, J 5.6 Hz, 2H), 3.15 (s, 3H), 3.14 (s, 3H), 2.11 (d, J 13.2 Hz, 2H), 1.94-1.82 (m, 2H), 1.19 (s, 3H). GCMS $[M-CH_3O]^+$ 129, RT 2.33 minutes (Method 9).

Intermediate 38

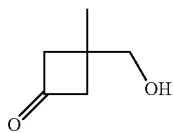

3-(Hydroxymethyl)-3-methylcyclobutanone

To a stirred solution of Intermediate 37 (44.8 g, 280 mmol) in acetone (600 mL) and water (200 mL) was added p-toluenesulfonic acid monohydrate (53.2 g, 280 mmol). The reaction mixture was heated at 65° C. for 1 h, then cooled to r.t. The acetone was removed by concentration in vacuo. The resulting mixture was diluted with DCM and washed with aqueous sodium hydrogen carbonate solution. The aqueous layer was extracted three times with DCM. The combined organic layers were dried ($MgSO_4$), then filtered and concentrated in vacuo, to afford the title compound (30.8 g, 78%). $\delta_H$ (400 MHz, $CDCl_3$) 3.69 (d, J 5.1 Hz, 2H), 3.09-2.97 (m, 2H), 2.76-2.64 (m, 2H), 1.36 (s, 3H).

Intermediate 39

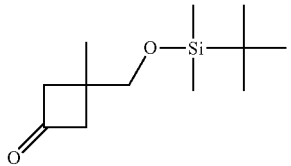

3-({[tert-Butyl(dimethyl)silyl]oxy}methyl)-3-methylcyclobutanone

Imidazole (0.63 g, 9.29 mmol) was added to a solution of Intermediate 38 (10.6 g, 55.0 mmol) in DMF (150 mL), followed by tert-butyl(chloro)dimethylsilane (24.9 g, 165 mmol). The reaction mixture was stirred at r.t. overnight. Diethyl ether was added, followed by brine. The organic layer was separated and washed three times with brine. The organic layers were dried and concentrated in vacuo. The crude residue (62 g) was purified by flash column chromatography on silica (gradient elution with 0-10% EtOAc in heptane) to afford the title compound (59.5 g) as a yellow oil. $\delta_H$ (400 MHz, $CDCl_3$) 3.59 (s, 2H), 3.08-2.98 (m, 2H), 2.66-2.56 (m, 2H), 1.30 (s, 3H), 0.89 (s, 9H), 0.06 (s, 6H).

Intermediate 40

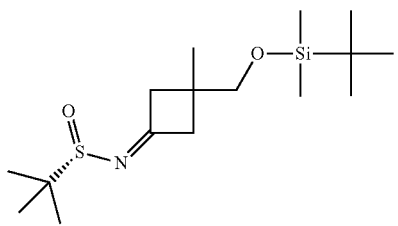 [SMILES: CC1(CO[Si](C)(C)C(C)(C)C)CC(=N[S@@](=O)C(C)(C)C)C1]

(S)—N-[3-({[tert-Butyl(dimethyl)silyl]oxy}methyl)-3-methylcyclobutylidene]-2-methylpropane-2-sulfinamide To a solution of Intermediate 39 (54.5 g, 205 mmol) in THF (500 mL) were added (S)-2-methylpropane-2-sulfinamide (29.8 g, 246 mmol) and titanium(IV) ethoxide (87 mL, 410 mmol). The reaction mixture was stirred overnight at r.t., then concentrated in vacuo. The residue was diluted with acetonitrile, then water (47 mL) was added. The mixture was stirred for 10 minutes, then filtered over kieselguhr and rinsed with acetonitrile. The filtrate was concentrated in vacuo. The resulting crude yellow oil (71.5 g) was purified by flash column chromatography on silica (gradient elution with 0-20% EtOAc in heptane) to afford the title compound (66.9 g, 98%) as a yellow oil (~1:1 mixture of isomers). $\delta_H$ (400 MHz, $CDCl_3$) 3.50 (d, J 1.6 Hz, 2H), 3.46-3.38 (m, 0.5H), 3.24-3.00 (m, 2H), 2.92-2.82 (m, 0.5H), 2.71-2.55 (m, 1H), 1.29-1.19 (m, 12H), 0.90-0.88 (m, 9H), 0.05 (s, 6H).

Intermediate 41

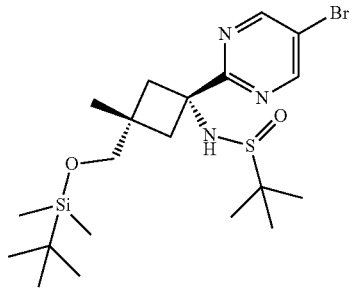 [SMILES: CC(C)(C)S(=O)N[C@]1(c2ncc(Br)cn2)C[C@](C)(CO[Si](C)(C)C(C)(C)C)C1]

N-[1-(5-Bromopyrimidin-2-yl)-3-({[tert-butyl(dimethyl)silyl]oxy}methyl)-3-methylcyclobutyl]-2-methylpropane-2-sulfinamide A solution of 5-bromo-2-iodopyrimidine (58.6 g, 206 mmol) in DCM (500 mL) was cooled to −78° C. n-Butyllithium (2.5M in hexanes, 90 mL, 226 mmol) was added dropwise over 10 minutes, resulting in a thick suspension. The mixture was stirred for 40 minutes at −78° C. A solution of Intermediate 40 (56.8 g, 171 mmol) in DCM (500 mL) was added dropwise. The reaction mixture was stirred for 2.5 h at −78° C., then allowed to warm to r.t. and stirred for 1 h. The mixture was poured into saturated aqueous ammonium chloride solution and was stirred for 5 minutes. After dilution with water, the layers were separated. The aqueous layer was extracted twice with DCM. The organic layers were combined, washed with brine and dried (Na$_2$SO$_4$), then filtered and concentrated in vacuo. The crude residue was purified by flash column chromatography on silica (gradient elution with 1:1 to 0:1 heptane:EtOAc), followed by additional purification by flash column chromatography on silica (gradient elution with 20-80% EtOAc in heptane), to furnish the title compound (16 g, 17%). δ$_H$ (400 MHz, CDCl$_3$) 8.76 (s, 2H), 4.40 (s, 1H), 3.58 (d, J 9.6 Hz, 1H), 3.52 (d, J 9.5 Hz, 1H), 2.84 (d, J 12.7 Hz, 1H), 2.54-2.38 (m, 2H), 2.30 (d, J 12.3 Hz, 1H), 1.20 (s, 9H), 1.04 (s, 3H), 0.91 (s, 9H), 0.07 (s, 6H). LCMS [M+H]$^+$ 490/492 (Br-pattern), RT 2.49 minutes (Method 6).

Intermediate 42

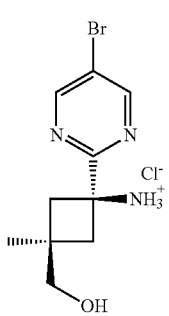

[1-(5-Bromopyrimidin-2-yl)-3-(hydroxymethyl)-3-methylcyclobutyl]ammonium Chloride To a stirred solution of Intermediate 41 (88.38 g, 180.15 mmol) in anhydrous 1,4-dioxane (750 mL) was added 4M HCl in 1,4-dioxane (200 mL). The reaction mixture was stirred for 18 h, then diethyl ether (1800 mL) was added. The suspension was filtered, then the solids were washed with diethyl ether (2×0.5 L) and dried under suction, to afford the title compound (53.06 g, 95%) as an off-white solid. δ$_H$ (500 MHz, DMSO-d$_6$) 9.16 (s, 2H), 8.75 (s, 3H), 3.43 (s, 2H), 2.98-1.63 (m, 4H), 1.15 (s, 3H). LCMS [M+H]$^+$ 271.9/273.9 (Br-pattern), RT 0.71 minutes (Method 7).

Intermediate 43

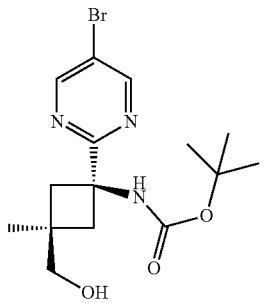 [SMILES: CC(C)(C)OC(=O)N[C@]1(c2ncc(Br)cn2)C[C@](C)(CO)C1]

tert-Butyl N-[1-(5-bromopyrimidin-2-yl)-3-(hydroxymethyl)-3-methylcyclobutyl]-carbamate To an externally cooled (10° C.) suspension of Intermediate 42 (53.06 g, 171.93 mmol) and di-tert-butyl dicarbonate (59.7 g, 273.54 mmol) in anhydrous 1,4-dioxane (750 mL) was added DIPEA (45 mL, 258 mmol) over 5 minutes. The external cooling was removed and the reaction mixture was stirred for 3 h. Additional DIPEA (45 mL) and di-tert-butyl dicarbonate (21.6 g) were added. After 2.5 h, the reaction mixture was concentrated under reduced pressure. The crude residue was partitioned between EtOAc and 10% aqueous citric acid solution. The aqueous phase was extracted twice with EtOAc and the combined organic phases were dried over magnesium sulphate, then filtered and concentrated in vacuo. The residue was azeotroped twice with heptane, to afford the title compound (40.11 g, 63%) as an off-white powder. δ$_H$ (500 MHz, DMSO-d$_6$) 9.02-8.86 (m, 2H), 7.66-7.20 (m, 1H), 4.71-4.52 (m, 1H), 3.41 (d, J 4.4 Hz, 2H), 2.32 (d, J 12.3 Hz, 2H), 2.24 (d, J 12.3 Hz, 2H), 1.39-0.97 (m, 12H). LCMS [M+H]$^+$ 372.2/374.3 (Br-pattern), RT 1.61 minutes (Method 8).

Intermediate 44

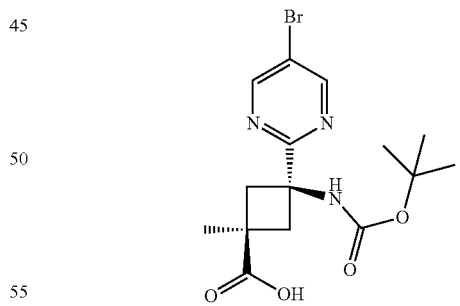

3-(5-Bromopyrimidin-2-yl)-3-(tert-butoxycarbonylamino)-1-methylcyclobutane-carboxylic Acid To a stirred solution of Intermediate 43 (52.72 g, 141.6 mmol) in a mixture of acetonitrile (630 mL) and DCM (1000 mL) were added sodium periodate (91.18 g, 426.3 mmol) and water (1 L). Ruthenium(III) chloride (2.68 g, 12.92 mmol) was added and the reaction mixture was stirred for 5.5 h. The precipitated solid was filtered off and washed with DCM (100 mL) and water (3×300 mL), then dried, to provide the title compound (36.3 g, 66%) as a pale grey solid. $\delta_H$ (500 MHz, DMSO-$d_6$) 12.23 (s, 1H), 8.95 (s, 2H), 7.68-7.30 (m, 1H), 2.82 (d, J 12.4 Hz, 2H), 2.51 (d, J 1.8 Hz, 2H), 1.36 (s, 3H), 1.34-0.99 (m, 9H). LCMS [M+H]$^+$ 386.1/388.1 (Br-pattern), RT 1.13 minutes (Method 8).

Intermediate 45

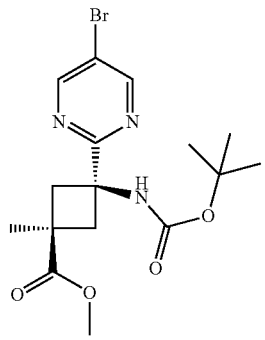 [SMILES: COC(=O)[C@]1(C)C[C@@](NC(=O)OC(C)(C)C)(c2ncc(Br)cn2)C1]

Methyl 3-(5-bromopyrimidin-2-yl)-3-(tert-butoxy-carbonylamino)-1-methylcyclobutanecarboxylate A suspension of Intermediate 44 (36.3 g, 94 mmol) in dry DMF (270 mL) was cooled on an ice bath and potassium carbonate (19.9 g, 144 mmol) was added, followed by iodomethane (9 mL, 144.6 mmol). The reaction mixture was stirred for 45 minutes, then the cooling bath was removed and the reaction mixture was stirred at ambient temperature for 3 h. Water (850 mL) was added. The thick solid precipitate was filtered off and washed with water (3×400 mL). The filter cake was dissolved in EtOAc (300 mL) and the sinter funnel was flushed with EtOAc (2×50 mL). The organic filtrate was washed twice with brine (100 mL) and dried over anhydrous magnesium sulphate, then filtered and concentrated in vacuo. Heptane (300 mL) was added and the solid was filtered off, then washed with heptane (2×100 mL) and dried by suction, to give the title compound (34.9 g, 93%) as a white solid. $\delta_H$ (500 MHz, DMSO-$d_6$) 8.96 (s, 2H), 7.70-7.34 (m, 1H), 3.66 (s, 3H), 2.85 (d, J 12.1 Hz, 2H), 2.59 (d, J 12.3 Hz, 2H), 1.37 (s, 3H), 1.35-0.96 (m, 9H). LCMS [M+H]$^+$ 400.1/402.1 (Br-pattern), RT 1.81 minutes (Method 8).

Intermediate 46

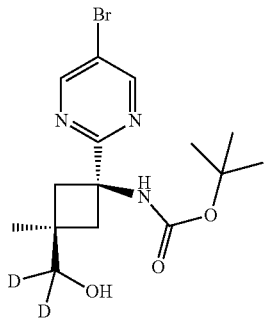 [SMILES: [2H]C([2H])(O)[C@]1(C)C[C@@](NC(=O)OC(C)(C)C)(c2ncc(Br)cn2)C1]

tert-Butyl N-{1-(5-bromopyrimidin-2-yl)-3-[dideu-terio(hydroxy)methyl]-3-methylcyclobutyl}carbamate To a suspension of LiAlD$_4$ (1.82 g, 43.41 mmol) in dry THF (265 mL), cooled to −75° C., was added a solution of Intermediate 45 (17.52 g, 43.77 mmol) in dry THF (90 mL) dropwise over approximately 40 minutes. The reaction mixture was stirred for 1.5 h, then sodium sulfate decahydrate (34.9 g, 108.32 mmol) was added portionwise over approximately 10 minutes. After a further 15 minutes, the external cooling was removed and the mixture was stirred at ambient temperature. The solid was filtered and washed with THF (3×100 mL). The filtrate was concentrated in vacuo. The crude residue was dissolved in DCM (20 mL) and purified by flash column chromatography (0-60% EtOAc in heptane) to give the title compound (4.16 g, 25%) as an off-white solid. $\delta_H$ (500 MHz, DMSO-$d_6$) 8.93 (s, 2H), 7.62-7.23 (m, 1H), 4.57 (s, 1H), 2.32 (d, J 12.4 Hz, 2H), 2.23 (d, J 12.3 Hz, 2H), 1.41-0.94 (m, 12H). LCMS [M+H]$^+$ 374.2/376.2 (Br-pattern), RT 1.64 minutes (Method 8).

Intermediate 47

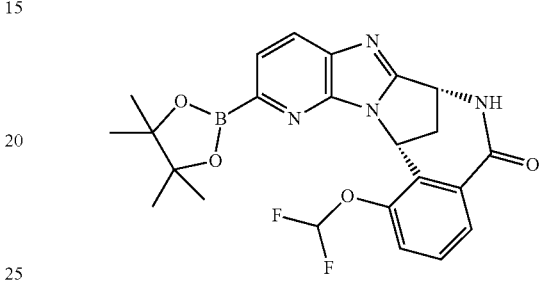

(7R,14R)-1-(Difluoromethoxy)-11-(4,4,5,5-tetram-ethyl-1,3,2-dioxaborolan-2-yl)-6,7-dihydro-7,14-methanopyrido[3',2':4,5]imidazo[1,2-b][2,5]benzodi-azocin-5(14H)-one A 5 mL microwave vial was charged with Intermediate 10 (221.5 mg, 0.588 mmol), bis(pinacolato)diboron (226 mg, 0.89 mmol), potassium acetate (175 mg, 1.78 mmol), tricyclohexylphosphonium tetrafluoroborate (24 mg, 0.063 mmol) and tris(dibenzylideneacetone)dipalladium(0) (25.8 mg, 0.027 mmol), followed by degassed 1,4-dioxane (2.1 mL). The reaction mixture was heated under microwave irradiation at 130° C. for 3 h. A few drops of acetic acid were added to the reaction mixture, which was then partitioned between EtOAc (15 mL) and water (15 mL). The aqueous phase was extracted with additional EtOAc (2×15 mL). The combined organic phases were dried over anhydrous magnesium sulphate, then filtered and concentrated in vacuo, to afford the title compound, which was utilised without further purification.

Intermediate 48

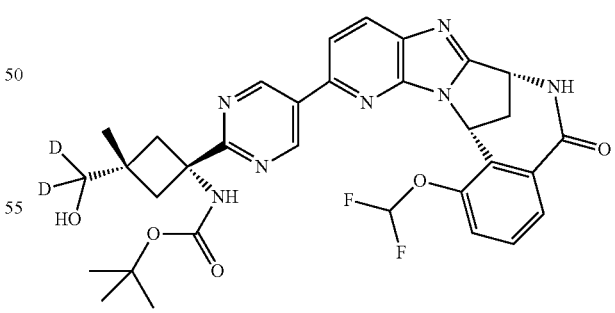

tert-Butyl (cis-1-{5-[(7R,14R)-1-(difluoromethoxy)-5-oxo-5,6,7,14-tetrahydro-7,14-methanopyrido[3',2':4,5]imidazo[1,2-b][2,5]benzodiazocin-11-yl]pyrimidin-2-yl}-3-[hydroxy(dideutero)methyl]-3-methylcyclobutyl)carbamate To a mixture of Intermediate 47 (271.7 mg, 0.58 mmol), tris(dibenzylidene-acetone)dipalladium(0) (25.2 mg, 0.028 mmol), tricyclohexylphosphonium tetrafluoroborate (22.8 mg, 0.06 mmol) and Intermediate 46 (198 mg, 0.53 mmol) in degassed 1,4-dioxane (2 mL) was added potassium phosphate tribasic (348 mg, 1.59 mmol) in water (0.2 mL). The reaction mixture was degassed for 10 minutes with nitrogen, then heated at 110° C. under microwave irradiation for 3 h. The reaction mixture was partitioned between EtOAc (20 mL) and water (20 mL), then the layers were separated and the aqueous phase was extracted with EtOAc (2×20 mL). The combined organic phases were passed through a phase separator cartridge and concentrated in vacuo. Purification by column chromatography (0-100% EtOAc in hexane, followed by 0-15% MeOH in EtOAc) gave the title compound (126 mg, 38%) as a yellow oily solid. $\delta_H$ (300 MHz, DMSO-$d_6$) 9.41 (s, 2H), 9.17 (d, J 6.7 Hz, 1H), 8.26-8.21 (m, 1H), 8.17 (d, J 8.4 Hz, 1H), 7.99 (d, J 8.4 Hz, 1H), 7.58 (dd, J 72.4, 2.9 Hz, 1H), 7.49 (d, J 4.9 Hz, 2H), 6.49 (d, J 7.2 Hz, 1H), 4.92 (t, J 6.6 Hz, 1H), 4.58 (s, 1H), 3.58-3.46 (m, 1H), 2.75 (d, J 13.1 Hz, 1H), 2.50-2.32 (m, 2H), 2.28 (d, J 12.5 Hz, 2H), 1.37 (s, 9H), 1.16 (s, 3H). LCMS [M+H]$^+$ 636.2, RT 1.77 minutes (Method 2).

Intermediate 49

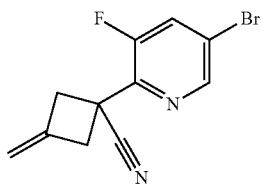

1-(5-Bromo-3-fluoropyridin-2-yl)-3-methylenecyclobutane-1-carbonitrile

In a 5 L 3-necked flask, under a nitrogen atmosphere, were combined 3-methylenecyclobutane-1-carbonitrile (64 mL, 623 mmol) and 5-bromo-2,3-difluoro-pyridine (56 mL, 519 mmol) in anhydrous toluene (1 L). The solution was cooled to 0° C., then sodium bis(trimethylsilyl)amide solution (0.6M in toluene) (0.995 L, 597 mmol) was added via a dropping funnel over 1 h. When the addition was completed, the mixture was stirred for 10 minutes at 0° C. The reaction mixture was poured into 0.5M aqueous citric acid (1.5 L) and extracted with EtOAc (2×1 L). The combined organic phases were washed with brine and dried (Na$_2$SO$_4$), then filtered and concentrated under reduced pressure. The resulting crude brown oil (160.7 g) was purified by vacuum distillation, with product collection at 90° C. (<0.001 Torr), to afford the title compound (98.86 g, 71.4%) as a colourless oil which crystallised on standing. LCMS [M+H]$^+$ 267/269, RT 2.07 minutes (Method 1).

Intermediate 50

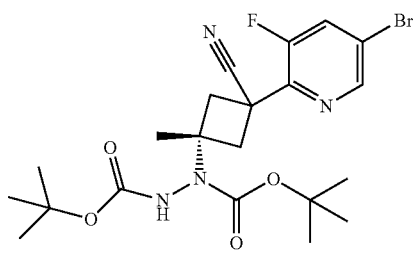

Di-tert-butyl 1-[(1R,3R)-3-(5-bromo-3-fluoropyridin-2-yl)-3-cyano-1-methylcyclobutyl]-hydrazine-1,2-dicarboxylate In a 3 L 3-necked flask, under a nitrogen flow, tris(2,2,6,6-tetramethyl-3,5-heptanedionato)manganese(III) (4.28 g, 7.08 mmol) was suspended in anhydrous 2-propanol (1.5 L). The mixture was cooled to 0° C., then Intermediate 49 (94.5 g, 354 mmol) and phenylsilane (0.044 L, 354 mmol) were added. Di-tert-butyl (E)-diazene-1,2-dicarboxylate (122 g, 531 mmol) was added in one portion and the reaction mixture was stirred at 0° C. After the addition, the internal temperature was 5° C. A dark mixture formed, which slowly warmed up to 10° C. After 90 minutes, the internal temperature had returned to 5° C. and the colour of the mixture had become much lighter. The reaction mixture was poured into brine (1.5 L) and the aqueous phase was extracted with EtOAc (2×1 L). The combined organic layers were washed with brine and dried (Na$_2$SO$_4$), then filtered and concentrated under reduced pressure. The resulting crude yellow wax (268 g) was dissolved in DCM (~250 mL) and filtered over a plug of silica (1.5 kg, 10-25% EtOAc in heptane), affording two batches of crude material. The crude batches were separately suspended in 2:1 heptane/EtOAc (~1 L) and heated until all material was dissolved. The solutions were slowly cooled to ambient temperature, during which a white crystalline solid formed. The solids were collected by filtration and rinsed with 9:1 heptane/EtOAc, then dried under vacuum, to give two batches of material (21.9 g and 27.9 g) as white solids. The filtrates were concentrated in vacuo and triturated from diisopropyl ether to give further material (10 g; 70% trans). The three batches were combined and triturated with diisopropyl ether overnight. The residue was collected by filtration, then rinsed with fresh diisopropyl ether, to give the title compound (51.5 g; >99% trans isomer) as a white solid. LCMS [M+H]$^+$ 499/501, RT 2.24 minutes (Method 1).

Intermediate 51

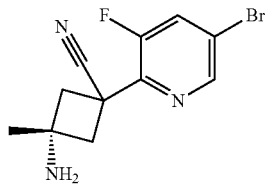

(1R,3R)-3-Amino-1-(5-bromo-3-fluoropyridin-2-yl)-3-methylcyclobutane-1-carbonitrile Under a nitrogen atmosphere, Intermediate 50 (42 g, 84 mmol) was dissolved in 4M hydrochloric acid in 1,4-dioxane (500 mL, 2 mol) and stirred at r.t. overnight. The mixture was cooled to 0° C., then anhydrous acetone (185 mL, 2.52 mol) was added. The reaction mixture was stirred for 45 minutes, then concentrated under reduced pressure and azeotroped with DCM and diethyl ether. To the resulting beige foam was added acetic acid (400 mL). The solution was cooled on an ice bath, then zinc dust (82 g, 1.26 mol) was added cautiously. After approximately 5 minutes, the cooling bath was removed and the mixture was stirred at ambient temperature for 45 minutes. The reaction mixture was diluted with DCM (400 mL), filtered over a plug of Kieselguhr and rinsed with DCM. The filtrate was concentrated under reduced pressure and azeotroped with toluene to give the title compound (67 g), which was utilised without further purification.

Intermediate 52

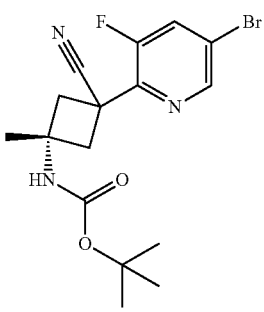

tert-Butyl [(1R,3R)-3-(5-bromo-3-fluoropyridin-2-yl)-3-cyano-1-methylcyclobutyl]-carbamate Under a nitrogen atmosphere, triethylamine (75 mL, 540 mmol) and di-tert-butyl dicarbonate (36.7 g, 168 mmol) were added to a mixture of Intermediate 51 (23.87 g, 84 mmol) in DCM (500 mL). The reaction mixture was stirred at ambient temperature overnight, then poured into 0.5M aqueous citric acid (750 mL). The aqueous phase was extracted with DCM (300 mL). The combined organic phases were washed with saturated aqueous $NaHCO_3$ solution. The layers were separated and the aqueous phase was extracted with DCM (250 mL). The combined organic layers were dried ($Na_2SO_4$), filtered and concentrated under reduced pressure. The resulting crude orange oil (40.5 g), that started to crystallise, was then purified by column chromatography (1 kg silica, 5-25% EtOAc in heptane) to give the title compound (26.0 g) as a white solid. LCMS $[M+H]^+$ 384/386, RT 2.12 minutes (Method 1).

Intermediate 53

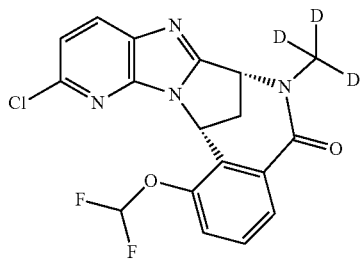 [SMILES: [2H]C([2H])([2H])N1C(=O)c2cccc(OC(F)F)c2[C@H]2C[C@@H]1c1nc3ccc(Cl)nc3n12]

(7R,14R)-11-Chloro-1-(difluoromethoxy)-6-trideuteromethyl-6,7-dihydro-7,14-methanopyrido[3',2':4,5]imidazo[1,2-b][2,5]benzodiazocin-5(14H)-one To a solution of Intermediate 10 (1.01 g, 2.54 mmol) in THF (20 mL) at −78° C. was added potassium bis(trimethylsilyl)amide (1M in THF, 2.8 mL, 2.8 mmol) dropwise. The reaction mixture was stirred at −78° C. for 30 minutes, then iodomethane-$D_3$ (0.24 mL, 3.9 mmol) was added. The reaction mixture was stirred at −78° C. for 30 minutes, then placed in an ice/water bath and stirred for a further 3 h. The reaction mixture was quenched by addition of saturated aqueous $NH_4C_1$ solution (10 mL) and extracted with EtOAc (20 mL). The aqueous phase was further extracted with EtOAc (3×10 mL). The combined organic phases were dried over anhydrous sodium sulphate, then filtered and concentrated in vacuo. The crude material was purified by column chromatography (0-100% EtOAc in hexane) to give the title compound (854 mg, 85%) as a pale yellow foam. $\delta_H$ (300 MHz, DMSO-$d_6$) 8.27 (dd, J 6.7, 2.7 Hz, 1H), 8.11 (d, J 8.4 Hz, 1H), 7.55-7.48 (m, 2H), 7.44 (dd, J 76.9, 70.7 Hz, 1H), 7.33 (d, J 8.4 Hz, 1H), 6.33 (d, J 7.3 Hz, 1H), 5.27 (d, J 7.0 Hz, 1H), 3.52 (dt, J 14.3, 7.3 Hz, 1H), 2.85-2.73 (m, 1H). LCMS $[M+H]^+$ 394.2, RT 1.76 minutes (Method 2).

Intermediate 54

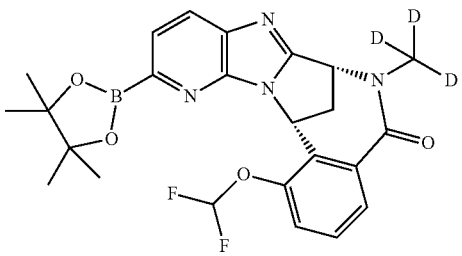 [SMILES: [2H]C([2H])([2H])N1C(=O)c2cccc(OC(F)F)c2[C@H]2C[C@@H]1c1nc3ccc(B4OC(C)(C)C(C)(C)O4)nc3n12]

(7R,14R)-1-(Difluoromethoxy)-6-trideuteromethyl-11-(4,4,5,5-tetramethyl-1,3,2-dioxaborolan-2-yl)-6,7-dihydro-7,14-methanopyrido[3',2':4,5]imidazo[1,2-b][2,5]-benzodiazocin-5(14H)-one To Intermediate 53 (200 mg, 0.51 mmol), tricyclohexylphosphonium tetrafluoroborate (20 mg, 0.053 mmol), tris(dibenzylideneacetone)dipalladium(0) (25 mg, 0.027 mmol), potassium acetate (152 mg, 1.55 mmol) and bis(pinacolato)diboron (194 mg, 0.76 mmol) was added degassed 1,4-dioxane (1.9 mL). The reaction mixture was degassed with nitrogen and heated at 130° C. for 3 h. A few drops of acetic acid were added to the reaction mixture, which was then partitioned between EtOAc and water. The organic phases were separated and the aqueous phase was extracted with EtOAc (2×15 mL). The combined organic phases were dried over anhydrous sodium sulphate, then filtered and concentrated in vacuo. The crude residue was purified by column chromatography (0-10% MeOH in DCM) to give the title compound (168 mg, 68%) as a brown oil. 6H (300 MHz, DMSO-$d_6$) 8.29 (dd, J 6.6, 3.0 Hz, 1H), 8.05-7.96 (m, 1H), 8.00 (t, J 74.1 Hz, 1H), 7.58 (d, J 8.1 Hz, 1H), 7.52-7.47 (m, 2H), 6.39 (d, J 7.3 Hz, 1H), 5.31 (d, J 7.0 Hz, 1H), 3.56 (dt, J 14.2, 7.2 Hz, 1H), 2.85 (d, J 13.9 Hz, 1H), 1.31 (s, 12H).

Intermediate 55

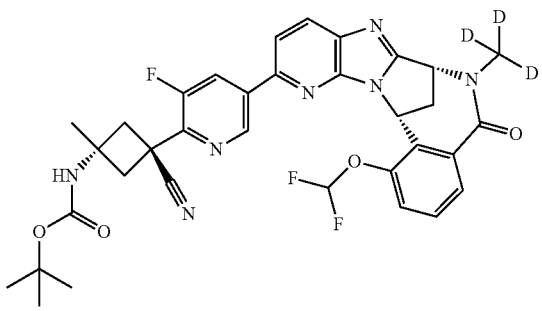 [SMILES: [2H]C([2H])([2H])N1C(=O)c2cccc(OC(F)F)c2[C@H]2C[C@@H]1c1nc3ccc(-c4cnc([C@]5(C#N)C[C@](C)(NC(=O)OC(C)(C)C)C5)c(F)c4)nc3n12]

tert-Butyl (trans-3-cyano-3-{5-[(7R,14R)-1-(difluoromethoxy)-6-trideuteromethyl-5-oxo-5,6,7,14-tetrahydro-7,14-methanopyrido[3',2':4,5]imidazo[1,2-b][2,5]benzodiazocin-11-yl]-3-fluoropyridin-2-yl}-1-methylcyclobutyl)carbamate To a mixture of Intermediate 54 (168 mg, 0.35 mmol), tris(dibenzylideneacetone)dipalladium(0) (19 mg, 0.021 mmol), tricyclohexylphosphonium tetrafluoroborate (13.2 mg, 0.035 mmol) and Intermediate 52 (155 mg, 0.40 mmol) in degassed 1,4-dioxane (1.4 mL) was added potassium acetate (232 mg, 0.09 mmol) in water (0.15 mL). The reaction mixture was heated at 110° C. under microwave irradiation for 3 h, then partitioned between EtOAc (15 mL) and water (15 mL). The organic phase was separated and the aqueous phase was further extracted with EtOAc (2×15 mL). The combined organic phases were dried (phase separator) and concentrated in vacuo. The resulting yellow oil (280 mg) was purified by column chromatography (25-100% EtOAc in hexane, followed by 0-10% MeOH in DCM) to give the title compound (105 mg, 46%) as a yellow oil. LCMS [M+H]$^+$ 663.0, RT 2.65 minutes (Method 2).

Example 1

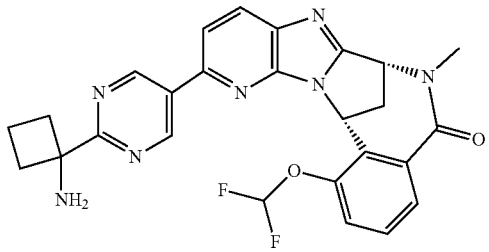 [SMILES: CN1C(=O)c2cccc(OC(F)F)c2[C@H]2C[C@@H]1c1nc3ccc(-c4cnc(C5(N)CCC5)nc4)nc3n12]

(7R,14R)-11-[2-(1-Aminocyclobutyl)pyrimidin-5-yl]-1-(difluoromethoxy)-6-methyl-6,7-dihydro-7,14-methanopyrido[3',2':4,5]imidazo[1,2-b][2,5]benzodiazocin-5(14H)-one Under nitrogen, 4M hydrochloric acid in 1,4-dioxane (0.5 mL, 2.0 mmol) was added to a solution of Intermediate 33 in MeOH (3.3 mL). After stirring for 2 h, the reaction mixture was concentrated in vacuo. The crude residue was partitioned between saturated aqueous sodium hydrogen carbonate solution and a 1:1 mixture of DCM and MeOH. The aqueous phase was separated and extracted three times with a 1:1 mixture of DCM and MeOH. The combined organic phases were dried (Na$_2$SO$_4$), filtered and concentrated in vacuo. The residue was purified by flash column chromatography on silica (gradient elution with 0-10% MeOH in DCM) to afford the title compound (199 mg, 80%) as a beige solid. δ$_H$ (400 MHz, CDCl$_3$) 9.24 (s, 2H), 8.48 (dd, J 6.7, 2.8 Hz, 1H), 8.09 (d, J 8.4 Hz, 1H), 7.62 (d, J 8.4 Hz, 1H), 7.45-7.37 (m, 2H), 7.03 (dd, J 78.2, 69.1 Hz, 1H), 6.54 (d, J 7.3 Hz, 1H), 4.99 (d, J 7.0 Hz, 1H), 3.54-3.44 (m, 1H), 3.53 (s, 3H), 2.91 (d, J 13.6 Hz, 1H), 2.86-2.74 (m, 2H), 2.34 (br s, 2H), 2.27-2.10 (m, 3H), 2.08-1.94 (m, 1H). LCMS [M+H]$^+$ 504, RT 2.32 minutes (Method 3).

Example 2

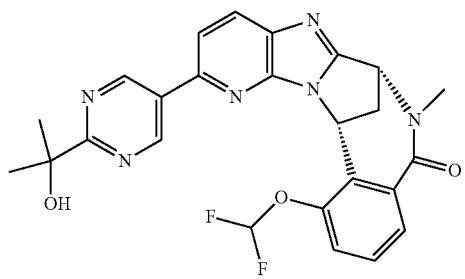 [SMILES: CN1C(=O)c2cccc(OC(F)F)c2[C@H]2C[C@@H]1c1nc3ccc(-c4cnc(C(C)(C)O)nc4)nc3n12]

(7R,14R)-1-(Difluoromethoxy)-11-[2-(2-hydroxypropan-2-yl)pyrimidin-5-yl]-6-methyl-6,7-dihydro-7,14-methanopyrido[3',2':4,5]imidazo[1,2-b][2,5]benzodiazocin-5(14H)-one Argon was bubbled through a mixture of Intermediate 11 (100 mg, 0.256 mmol), 2-[5-(4,4,5,5-tetramethyl-1,3,2-dioxaborolan-2-yl)pyrimidin-2-yl]propan-2-ol (101 mg, 0.384 mmol) and potassium phosphate (81 mg, 0.384 mmol) in a mixture of 1,4-dioxane (2.0 mL) and water (0.5 mL) for 10 minutes. [1,1'-Bis(diphenylphosphino)ferrocene]-dichloropalladium(II) (9.4 mg, 0.013 mmol) was added and the reaction vial was closed. The reaction mixture was stirred at 110° C. overnight, then concentrated in vacuo. The crude residue was partitioned between saturated aqueous sodium hydrogen carbonate solution and a 1:1 mixture of DCM and MeOH. The aqueous phase was separated and extracted three times with a 1:1 mixture of DCM and MeOH. The combined organic phases were dried (Na$_2$SO$_4$), filtered and concentrated in vacuo. The crude residue was purified by flash column chromatography on silica (gradient elution with 0-10% MeOH in DCM). The residue was triturated from diethyl ether to afford the title compound (77 mg, 61%) as an off-white solid. δ$_H$ (400 MHz, CDCl$_3$) 9.26 (s, 2H), 8.48 (dd, J 7.1, 2.4 Hz, 1H), 8.11 (d, J 8.4 Hz, 1H), 7.65 (d, J 8.4 Hz, 1H), 7.46-7.37 (m, 2H), 7.01 (dd, J 77.9, 69.4 Hz, 1H), 6.55 (d, J 7.3 Hz, 1H), 5.00 (d, J 7.0 Hz, 1H), 4.73 (s, 1H), 3.54-3.44 (m, 1H), 3.53 (s, 3H), 2.92 (d, J 13.6 Hz, 1H), 1.66 (s, 6H). LCMS [M+H]$^+$ 493, RT 2.95 minutes (Method 3).

Example 3

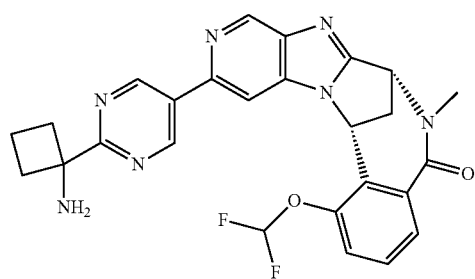 [SMILES: CN1C(=O)c2cccc(OC(F)F)c2[C@H]2C[C@@H]1c1nc3cnc(-c4cnc(C5(N)CCC5)nc4)cc3n12]

(7R,14R)-11-[2-(1-Aminocyclobutyl)pyrimidin-5-yl]-1-(difluoromethoxy)-6-methyl-6,7-dihydro-7,14-methanopyrido[3',4':4,5]imidazo[1,2-b][2,5]benzodiazocin-5(14H)-one 4M Hydrochloric acid in 1,4-dioxane (0.286 mL, 1.145 mmol) was added to a solution of Intermediate 34 (174 mg, 0.286 mmol) in MeOH (2 mL). In parallel, a separate experiment was performed commencing from Intermediate 34 (27 mg, 0.044 mmol). After 1 h, the separate reaction mixtures were combined and diluted with 1M aqueous hydrochloric acid solution, then washed with DCM (3×10 mL). The combined organic layers were extracted with 1M aqueous hydrochloric acid solution (20 mL), then the acidic aqueous layers were combined and basified with NaOH until pH ~12. The basic aqueous phase was extracted with DCM (3×50 mL). The combined organic phases were washed with 1M aqueous NaOH solution and dried (Na$_2$SO$_4$), then filtered and concentrated in vacuo. The residue was triturated from diisopropyl ether and diethyl ether, then dried at 40° C. overnight, to afford the title compound (111 mg, 67%) as an off-white solid. δ$_H$ (400 MHz, CDCl$_3$) 9.31 (s, 2H), 9.15-9.10 (m, 1H), 8.52 (d, J 7.6 Hz, 1H), 7.89-7.85 (m, 1H), 7.47 (t, J 8.2 Hz, 1H), 7.34 (d, J 8.2 Hz, 1H), 6.88 (t, J 72.8 Hz, 1H), 6.33 (d, J 7.2 Hz, 1H), 5.01 (d, J 7.1 Hz, 1H), 3.56-3.44 (m, 1H), 3.54 (s, 3H), 2.95 (d, J 13.7 Hz, 1H), 2.85-2.74 (m, 2H), 2.35-1.90 (m, 6H). LCMS [M+H]$^+$ 504, RT 2.25 minutes (Method 3).

Example 4

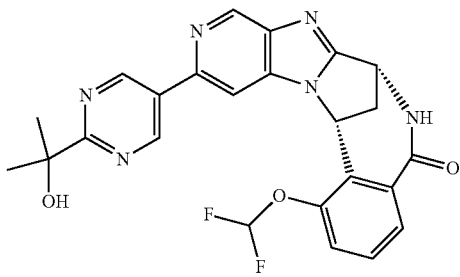 [SMILES: CC(C)(O)c1ncc(-c2cc3c(cn2)nc2n3[C@@H]3C[C@H]2NC(=O)c2cccc(OC(F)F)c23)cn1]

(7R,14R)-1-(Difluoromethoxy)-11-[2-(2-hydroxypropan-2-yl)pyrimidin-5-yl]-6,7-dihydro-7,14-methanopyrido[3',4':4,5]imidazo[1,2-b][2,5]benzodiazocin-5(14M-one To 2-[5-(4,4,5,5-tetramethyl-1,3,2-dioxaborolan-2-yl)pyrimidin-2-yl]propan-2-ol (121 mg, 0.459 mmol) and Intermediate 29 (185 mg, 0.417 mmol) in degassed 1,4-dioxane (4 mL) were added degassed 3M aqueous potassium carbonate solution (419 mg, 1.25 mmol, 0.42 mL) and [1,1'-bis(diphenylphosphino)ferrocene]dichloropalladium(II), dichloromethane complex (13.6 mg, 0.017 mmol). The reaction mixture was degassed and heated at 105° C. for 3 h. Additional 2-[5-(4,4,5,5-tetramethyl-1,3,2-dioxaborolan-2-yl)pyrimidin-2-yl]propan-2-ol (40 mg, 0.151 mmol) was added. The reaction mixture was heated overnight, then partitioned between EtOAc (20 mL) and water (10 mL). The organic phase was separated, washed with water (10 mL) and brine (10 mL), then filtered through a phase separator. The filtrate was concentrated in vacuo. The crude residue was purified by preparative HPLC to afford the title compound (19 mg, 10%). $\delta_H$ (300 MHz, DMSO-$d_6$) 9.32 (s, 2H), 9.20 (d, J 6.9 Hz, 1H), 9.06 (d, J 1.1 Hz, 1H), 8.27-8.19 (m, 1H), 7.95 (d, J 1.1 Hz, 1H), 7.75 (dd, J 74.1, 72.1 Hz, 1H), 7.54-7.51 (m, 2H), 6.43 (d, J 7.1 Hz, 1H), 5.17 (s, 1H), 4.96 (t, J 6.7 Hz, 1H), 3.51 (dt, J 13.7, 7.1 Hz, 1H), 2.80 (d, J 13.5 Hz, 1H), 1.54 (s, 6H). LCMS (ES+) [M+H]$^+$ 479.0, RT 1.38 minutes (Method 4). LCMS (ES+) [M+H]$^+$ 479.0, RT 1.42 minutes (Method 5).

Example 5

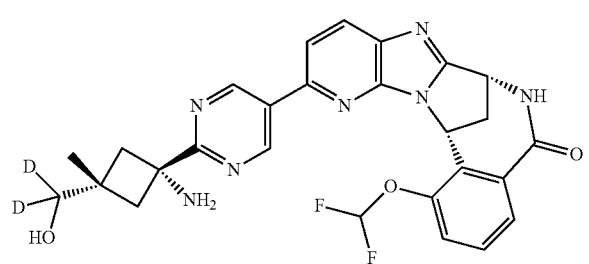 [SMILES: [2H]C([2H])(O)[C@]1(C)C[C@@](N)(c2ncc(-c3ccc4nc5n(c4n3)[C@@H]3C[C@H]5NC(=O)c4cccc(OC(F)F)c43)cn2)C1]

(7R,14R)-11-(2-{cis-1-Amino-3-[hydroxy(dideutero)methyl]-3-methylcyclobutyl}-pyrimidin-5-yl)-1-(difluoromethoxy)-6,7-dihydro-7,14-methanopyrido[3',2':4,5]imidazo-[1,2-b][2,5]benzodiazocin-5(14H)-one Hydrochloric acid in 1,4-dioxane (4M, 0.5 mL, 2 mmol) was added to a solution of Intermediate 48 (126 mg, 0.20 mmol) in ethanol (1 mL). After 2.5 h, a further portion of 4M hydrochloric acid in 1,4-dioxane (0.5 mL, 2 mmol) was added and the reaction mixture was left to stir overnight. A further portion of 4M hydrochloric acid in 1,4-dioxane (0.5 mL, 2 mmol) was added and the reaction mixture was stirred at r.t. for 4 h. The resulting solids (HCl salt) were filtered off, then washed with diethyl ether and DCM. The material was dissolved in water (20 mL) with a little acetonitrile, and extracted with EtOAc (20 mL). The aqueous phase was basified with 1M aqueous NaOH solution and extracted with EtOAc (3×25 mL). The combined organic phases were dried (phase separator) and concentrated in vacuo. The residue was purified by column chromatography (0-40% MeOH in DCM), then freeze-dried from water/acetonitrile, to give the title compound (27.5 mg, 26%). $\delta_H$ (300 MHz, DMSO-$d_6$) 9.47 (s, 2H), 9.17 (d, J 6.8 Hz, 1H), 8.27-8.22 (m, 1H), 8.19 (d, J 8.4 Hz, 1H), 8.01 (d, J 8.5 Hz, 1H), 7.60 (dd, J 72.4, 2.6 Hz, 1H), 7.50 (d, J 5.0 Hz, 2H), 6.49 (d, J 7.2 Hz, 1H), 4.92 (t, J 6.6 Hz, 1H), 3.61-3.45 (m, 1H), 2.76 (d, J 13.3 Hz, 2H), 2.51-2.43 (m, 1H), 2.19 (d, J 12.6 Hz, 2H), 1.10 (s, 3H). LCMS [M+H]$^+$ 536.0, RT 1.36 minutes (Method 3).

Example 6

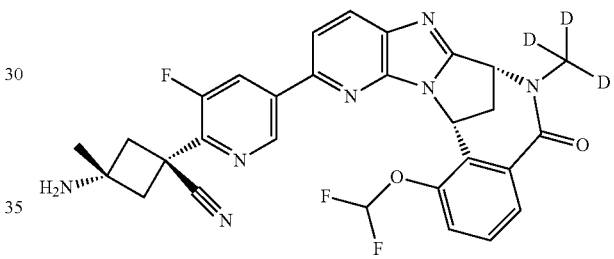

trans-3-Amino-1-{5-[(7R,14R)-1-(difluoromethoxy)-6-trideuteromethyl-5-oxo-5,6,7,14-tetrahydro-7,14-methanopyrido[3',2':4,5]imidazo[1,2-b][2,5]benzodiazocin-11-yl]-3-fluoropyridin-2-yl}-3-methylcyclobutanecarbonitrile Intermediate 55 was dissolved in 4M hydrochloric acid in 1,4-dioxane (0.5 mL) and ethanol (0.5 mL) and stirred overnight. The reaction mixture was partitioned between EtOAc (10 mL) and water (10 mL). The organic layer was discarded and the aqueous phase was basified with 1M aqueous NaOH solution, then extracted with EtOAc (3×20 mL). The combined organic phases were filtered through a phase separator and concentrated in vacuo. The resulting off-white solid was freeze-dried from water and acetonitrile to give the title compound (56 mg, 63%) as a white solid. $\delta_H$ (300 MHz, DMSO-$d_6$) 9.20 (t, J 1.7 Hz, 1H), 8.46 (dd, J 11.9, 1.8 Hz, 1H), 8.26 (dd, J 6.1, 3.4 Hz, 1H), 8.20 (d, J 8.5 Hz, 1H), 8.06 (d, J 8.5 Hz, 1H), 7.63 (dd, J 74.8, 72.6 Hz, 1H), 7.52-7.46 (m, 2H), 6.43 (d, J 7.2 Hz, 1H), 5.30 (d, J 7.0 Hz, 1H), 3.57 (dt, J 14.2, 7.3 Hz, 1H), 2.89-2.82 (m, 1H), 2.83-2.75 (m, 4H), 1.50 (s, 3H). LCMS [M+H]$^+$ 563, RT 1.51 minutes (Method 3).

The invention claimed is:
1. A compound of formula (I) or an N-oxide thereof, or a pharmaceutically acceptable salt thereof:

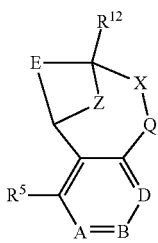

(I)

wherein
A represents N or C—$R^6$;
B represents N or C—$R^7$;
D represents N or C—$R^8$;
X—Q— represents —O—, —O—C(O)—, —C(O)—O—, —O—C(=CH—CN)—, —S—, —SO—, —$SO_2$—, —N($R^9$)—, —N($R_f$)—CO—, —CO—N($R^f$)—, —N($R^f$)—$SO_2$—, —$SO_2$—N($R^f$)—, —S(O)(N$R^f$)—, —N($R^f$)—C(S)—, —N=S(O)($CH_3$)—, —O—C(=$CH_2$)— or —S(=N—CN)—; or —X—Q— represents —$CH_2$—$CH_2$—, —O—$CH_2$—, —$CH_2$—O—, —S—$CH_2$—, —SO—$CH_2$—, —$SO_2$—$CH_2$—, —$CH_2$—S—, —$CH_2$—SO—, —$CH_2$—$SO_2$—, —N($R^9$)—$CH_2$—, —$CH_2$—N($R^9$)—, —S(O)(N$R^f$)—$CH_2$— or —$CH_2$—S(O)(N$R^f$)—, any of which groups can be optionally substituted by one or more substituents selected from halogen, $C_{1-6}$ alkyl, hydroxy($C_{1-6}$)alkyl, trifluoromethyl, $C_{2-6}$ alkylcarbonyl, carboxy and $C_{2-6}$ alkoxycarbonyl;
Z represents methylene;
E represents a fused heteroaromatic ring system selected from the groups of formula (Ea), (Eb) and (Ec):

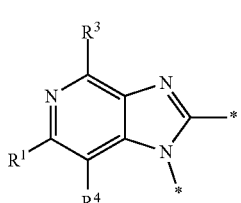

(Ea)

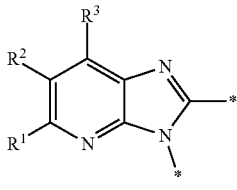

(Eb)

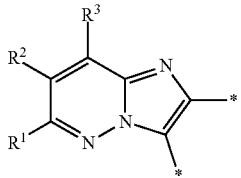

(Ec)

wherein the asterisks (*) represent the site of attachment of E to the remainder of the molecule;
$R^1$ represents hydrogen, halogen, cyano, trifluoromethyl, trifluoromethoxy, —$OR^a$, —$SR^a$, —$SOR^a$, —$SO_2R^a$, —$NR^cR^c$, —$NR^cCOR^d$, —$NR^cCO_2R^d$, —$NHCONR^bR^c$, —$NR^cSO_2R^e$, —$COR^d$, —$CO_2R^d$, —$CONR^bR^c$, —$SO_2NR^bR^c$, or —S(O)(N—$R^b$)$R^e$; or $R^1$ represents $C_{1-6}$ alkyl, $C_{3-7}$ cycloalkyl, $C_{4-7}$ cycloalkenyl, aryl, aryl($C_{1-6}$)alkyl, $C_{3-7}$ heterocycloalkyl, $C_{3-7}$ heterocycloalkenyl, heteroaryl, heteroaryl($C_{1-6}$)alkyl, ($C_{3-7}$)heterocycloalkyl($C_{1-6}$)alkyl-aryl-, ($C_{3-7}$)heterocycloalkenyl-aryl-, ($C_{3-7}$)cycloalkyl-heteroaryl-, ($C_{3-7}$)cycloalkyl-($C_{1-6}$)alkyl-heteroaryl-, ($C_{4-7}$)cycloalkenyl-heteroaryl-, ($C_{4-9}$)bicycloalkyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups can be optionally substituted by one or more substituents selected from halogen, cyano, $C_{1-6}$ alkyl, difluoromethyl, hydroxy($C_{1-6}$)alkyl, oxo, amino and amino($C_{1-6}$)alkyl;
$R^2$ represents hydrogen, halogen, cyano, nitro, hydroxy, trifluoromethyl, trifluoromethoxy or —$OR^a$; or $R^2$ represents $C_{1-6}$ alkyl or heteroaryl, either of which groups may can be optionally substituted by one or more substituents selected from hydroxy($C_{1-6}$)alkyl and $C_{2-6}$ alkoxycarbonyl;
$R^3$ and $R^4$ independently represent hydrogen, halogen or trifluoromethyl; or $C_{1-6}$ alkyl;
$R^5$ represents hydrogen, halogen, hydroxy, cyano, trifluoromethyl, difluoromethoxy, trifluoromethoxy, —$OR^a$ or $C_{1-6}$ alkylsulphonyl; or $R^5$ represents $C_{1-6}$ alkyl;
$R^6$, $R^7$ and $R^8$ independently represent hydrogen, halogen, trifluoromethyl, $C_{1-6}$ alkyl or $C_{1-6}$ alkoxy;
$R^{12}$ represents hydrogen or $C_{1-6}$ alkyl;
$R^a$ represents $C_{1-6}$ alkyl, $C_{3-7}$ cycloalkyl, aryl, aryl($C_{1-6}$)alkyl, $C_{3-7}$ heterocycloalkyl, heteroaryl or heteroaryl($C_{1-6}$)alkyl, any of which groups can be optionally substituted by one or more $C_{1-6}$ alkoxy or oxo;
$R^b$ represent hydrogen; or $C_{1-6}$ alkyl, aryl($C_{1-6}$)alkyl, $C_{3-7}$ heterocycloalkyl, $C_{3-7}$ heterocycloalkyl($C_{1-6}$)alkyl, any of which groups can be optionally substituted by one or more substituents selected from $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-($C_{1-6}$)alkylamino and $C_{2-6}$ alkoxycarbonylamino;
$R^c$ represents hydrogen; or $C_{1-6}$ alkyl, $C_{3-7}$ cycloalkyl, or $C_{3-7}$ heterocycloalkyl, any of which groups may be optionally substituted by $C_{2-6}$ alkylcarbonyl or $C_{2-6}$ alkoxycarbonyl;
or
$R^b$ and $R^c$, when taken together with the nitrogen atom to which they are both attached, represent a heterocyclic moiety selected from azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl, homopiperazin-1-yl, (imino)(oxo)thiazinan-4-yl, (oxo)thiazinan-4-yl and (dioxo)thiazinan-4-yl, any of which groups can be optionally substituted by one or more substituents selected from $C_{1-6}$ alkyl, $C_{1-6}$ alkylsulphonyl, hydroxy, hydroxy($C_{1-6}$)alkyl, amino($C_{1-6}$)alkyl, cyano, oxo, $C_{2-6}$ alkylcarbonyl, carboxy, $C_{2-6}$ alkoxycarbonyl, amino, $C_{2-6}$ alkylcarbonyl-amino, $C_{2-6}$ alkylcarbonylamino($C_{1-6}$)alkyl, $C_{2-6}$ alkoxycarbonylamino, $C_{1-6}$ alkyl-sulphonylamino and aminocarbonyl;
$R^d$ represents hydrogen; or $R^d$ represents $C_{1-6}$ alkyl, $C_{3-7}$ cycloalkyl, aryl, $C_{3-7}$ heterocycloalkyl or heteroaryl, any of which groups can be optionally substituted by one or more substituents selected from halogen, $C_{1-6}$ alkyl, $C_{1-6}$ alkoxy, oxo, $C_{2-6}$ alkylcarbonyloxy and di($C_{1-6}$)alkylamino;

$R^e$ represents $C_{1-6}$ alkyl, aryl or heteroaryl, any of which groups can be optionally substituted by $C_{1-6}$ alkyl;

$R^f$ represents hydrogen; or $R^f$ represents $C_{1-6}$ alkyl, $C_{3-7}$ cycloalkyl or $C_{3-7}$ heterocycloalkyl, any of which groups can be optionally substituted by one or more hydroxy or carboxy; and $R^g$ represents hydrogen, $-SO_2R^a$, $-COR^d$ or $-CO_2R^d$; or $R^g$ represents $C_{1-6}$ alkyl, $C_{3-7}$ cycloalkyl, $C_{3-7}$ heterocycloalkyl or heteroaryl, any of which groups can be optionally substituted by one or more substituents selected from halogen, trifluoromethyl, $C_{1-6}$ alkyl, $C_{4-9}$ heterobicycloalkyl, hydroxy, $C_{1-6}$ alkoxy, $C_{1-6}$ alkylsulphonyl, carboxy and $C_{2-6}$ alkoxycarbonyl.

2. The compound as claimed in claim 1 wherein A represents C—$R^6$, B represents C—$R^7$, and D represents C—$R^8$.

3. The compound as claimed in claim 1 represented by formula (IIA) or an N-oxide thereof, or a pharmaceutically acceptable salt thereof:

(IIA)

4. The compound as claimed in claim 3 represented by formula (IIA-1) or an N-oxide thereof, or a pharmaceutically acceptable salt thereof:

(IIA-1)

wherein
W represents N, CH or CF;
$R^9$ represents hydroxy($C_{1-6}$)alkyl or amino($C_{1-6}$)alkyl;
$R^{10}$ represents hydrogen or $C_{1-6}$ alkyl;
$R^5$ represents hydrogen, halogen, hydroxy, cyano, trifluoromethyl, difluoromethoxy, trifluoromethoxy, $-OR^a$ or $C_{1-6}$ alkylsulphonyl; or $R^5$ represents $C_{1-6}$ alkyl;
$R^a$ represents $C_{1-6}$ alkyl, $C_{3-7}$ cycloalkyl, aryl, aryl($C_{1-6}$)alkyl, $C_{3-7}$ heterocycloalkyl, heteroaryl or heteroaryl ($C_{1-6}$)alkyl, any of which groups may be optionally substituted by one or more $C_{1-6}$ alkoxy or oxo;

$R^6$, $R^7$ and $R^8$ independently represent hydrogen, halogen, trifluoromethyl, $C_{1-6}$ alkyl or $C_{1-6}$ alkoxy; and
$R^f$ represents hydrogen; or $R^f$ represents $C_{1-6}$ alkyl, $C_{3-7}$ cycloalkyl or $C_{3-7}$ heterocycloalkyl, any of which groups can be optionally substituted by one or more hydroxy or carboxy.

5. The compound as claimed in claim 3 represented by formula (IIA-2) or an N-oxide thereof, or a pharmaceutically acceptable salt thereof:

(IIA-2)

wherein
$R^{11}$ represents a group of formula (a), (b), (c), (d), (e), (f) or (g):

(a)

(b)

(c)

(d)

(e)

(f)

(g)

in which the asterisk (*) represents the site of attachment to the remainder of the molecule;

U represents O, S, S(O), S(O)$_2$, S(O)(NR$^b$), N(R$^{31}$) or C(R$^{32}$)(R$^{33}$);

R$^{31}$ represents hydrogen, cyano(C$_{1-6}$)alkyl, C$_{1-6}$ alkyl, trifluoromethyl, trifluoroethyl, C$_{1-6}$ alkylsulphonyl, (C$_{1-6}$)alkylsulphonyl(C$_{1-6}$)alkyl, formyl, C$_{2-6}$ alkylcarbonyl, carboxy, carboxy(C$_{1-6}$)alkyl, C$_{2-6}$ alkoxycarbonyl, C$_{2-6}$ alkoxycarbonyl(C$_{1-6}$)alkyl, tetrazolyl(C$_{1-6}$)alkyl, am inocarbonyl, C$_{1-6}$ alkylaminocarbonyl, di(C$_{1-6}$)alkylaminocarbonyl, aminosulphonyl, C$_{1-6}$ alkylaminosulphonyl or di(C$_{1-6}$)alkylaminosulphonyl;

R$^{32}$ represents hydrogen, halogen, cyano, C$_{1-6}$ alkyl, hydroxy, hydroxy(C$_{1-6}$)alkyl, C$_{1-6}$ alkylsulphonyl, formyl, carboxy, carboxy(C$_{1-6}$)alkyl, C$_{2-6}$ alkoxycarbonyl, C$_{2-6}$ alkoxycarbonyl(C$_{1-6}$)alkyl, aminosulphonyl, (C$_{1-6}$)alkylsulphoximinyl, [(C$_{1-6}$)alkyl][N—(C$_{1-6}$)alkyl]sulphoximinyl, (C1-6)alkylsulphonylaminocarbonyl, (C$_{2-6}$)alkylcarbonylamino-sulphonyl, (C$_{1-6}$) alkoxyaminocarbonyl, tetrazolyl or hydroxyoxadiazolyl;

R$^{33}$ represents hydrogen, halogen, C$_{1-6}$ alkyl, difluoromethyl, trifluoromethyl, hydroxy, hydroxy(C$_{1-6}$)alkyl, C$_{1-6}$ alkoxy, amino or carboxy;

R$^{34}$ represents hydrogen, halogen, halo(C$_{1-6}$)alkyl, cyano, hydroxy, C$_{1-6}$ alkoxy, C$_{1-6}$ alkylthio, C$_{1-6}$ alkylsulphinyl, C$_{1-6}$ alkylsulphonyl, amino, C$_{1-6}$ alkylamino, di(C$_{1-6}$)-alkylamino, (C$_{2-6}$)alkylcarbonylamino, (C$_{2-6}$) alkylcarbonylamino(C$_{1-6}$)alkyl, (C$_{1-6}$)alkyl-sulphonylamino or (C$_{1-6}$)alkylsulphonylamino(C$_{1-6}$)alkyl;

R$^{35}$ represents hydrogen or C$_{1-6}$ alkyl;

R$^{36}$ and R$^{37}$ independently represent C$_{1-6}$ alkyl; or

R$^{36}$ and R$^{37}$, when taken together with the carbon atom to which they are both attached, represent C$_{3-7}$ cycloalkyl;

R$^5$ represents hydrogen, halogen, hydroxy, cyano, trifluoromethyl, difluoromethoxy, trifluoromethoxy, —OR$^a$ or C$_{1-6}$ alkylsulphonyl; or R$^5$ represents C$_{1-6}$ alkyl;

R$^a$ represents C$_{1-6}$ alkyl, C$_{3-7}$ cycloalkyl, aryl, aryl(C$_{1-6}$) alkyl, C$_{3-7}$ heterocycloalkyl, heteroaryl or heteroaryl (C$_{1-6}$)alkyl, any of which groups can be optionally substituted by one or more C$_{1-6}$ alkoxy or oxo;

R$^6$, R$^7$ and R$^8$ independently represent hydrogen, halogen, trifluoromethyl, C$_{1-6}$ alkyl or C$_{1-6}$ alkoxy;

R$^b$ represents hydrogen or trifluoromethyl; or C$_{1-6}$ alkyl, C$_{3-7}$ cycloalkyl, C$_{3-7}$ cycloalkyl(C$_{1-6}$)alkyl, aryl, aryl (C$_{1-6}$)alkyl, C$_{3-7}$ heterocycloalkyl, C$_{3-7}$ heterocycloalkyl(C$_{1-6}$)alkyl, heteroaryl or heteroaryl(C$_{1-6}$)alkyl, any of which groups may can be optionally substituted by one or more substituents selected from C$_{1-6}$ alkoxy, C$_{1-6}$ alkylthio, C$_{1-6}$ alkylsulphinyl, C$_{1-6}$ alkylsulphonyl, hydroxy, cyano, C$_{2-6}$ alkoxycarbonyl, di—(C$_{1-6}$)alkylamino and C$_{2-6}$ alkoxycarbonylamino;

R$^f$ represents hydrogen; or R$^f$ represents C$_{1-6}$ alkyl, C$_{3-7}$ cycloalkyl or C$_{3-7}$ heterocycloalkyl, any of which groups can be optionally substituted by one or more hydroxy or carboxy;

W represents N, CH or CF; and

R$^{10}$ represents hydrogen or C$_{1-6}$ alkyl.

6. The compound as claimed in claim 1 represented by formula (IIB) or an N-oxide thereof, or a pharmaceutically acceptable salt thereof:

(IIB)

7. The compound as claimed in claim 6 represented by formula (IIB-1) or an N-oxide thereof, or a pharmaceutically acceptable salt thereof:

(IIB-1)

wherein

R$^2$ represents hydrogen, halogen, cyano, nitro, hydroxy, trifluoromethyl, trifluoromethoxy or —OR$^a$; or R$^2$ represents C$_{1-6}$ alkyl or heteroaryl, either of which groups can be optionally substituted by one or more substituents selected from hydroxy(C)alkyl and C$_{2-6}$ alkoxycarbonyl;

R$^5$ represents hydrogen, halogen, hydroxy, cyano, trifluoromethyl, difluoromethoxy, trifluoromethoxy, —OR$^a$ or C$_{1-6}$ alkylsulphonyl; or R$^5$ represents C$_{1-6}$ alkyl;

R$^a$ represents C$_{1-6}$ alkyl, C$_{3-7}$ cycloalkyl, aryl, aryl(C$_{1-6}$) alkyl, C$_{3-7}$ heterocycloalkyl, heteroaryl or heteroaryl (C$_{1-6}$)alkyl, any of which groups can be optionally substituted by one or more C$_{1-6}$ alkoxy or oxo;

R$^6$, R$^7$ and R$^8$ independently represent hydrogen, halogen, trifluoromethyl, C$_{1-6}$ alkyl or C$_{1-6}$ alkoxy; and R$^f$ represents hydrogen; or R$^f$ represents C$_{1-6}$ alkyl, C$_{3-7}$ cycloalkyl or C$_{3-7}$ heterocycloalkyl, any of which groups can be optionally substituted by one or more hydroxy or carboxy;

W represents N, CH or CF;

R$^9$ represents hydroxy(C$_{1-6}$)alkyl or amino(C$_{1-6}$)alkyl; and

R$^{10}$ represents hydrogen or C$_{1-6}$ alkyl.

8. The compound as claimed in claim 6 represented by formula (IIB-2) or an N-oxide thereof, or a pharmaceutically acceptable salt thereof:

(IIB-2)

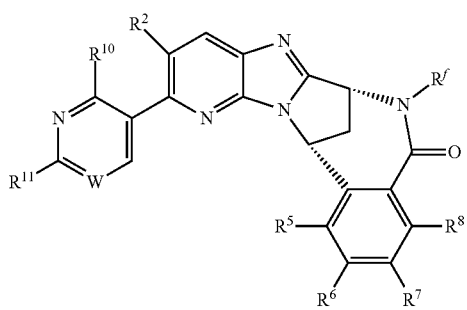

wherein
- R² represents hydrogen, halogen, cyano, nitro, hydroxy, trifluoromethyl, trifluoromethoxy or —OR$^a$; or R² represents C$_{1-6}$ alkyl or heteroaryl, either of which groups can be optionally substituted by one or more substituents selected from hydroxy(C)alkyl and C$_{2-6}$ alkoxycarbonyl;
- R⁵ represents hydrogen, halogen, hydroxy, cyano, trifluoromethyl, difluoromethoxy, trifluoromethoxy, —OR$^a$ or C$_{1-6}$ alkylsulphonyl; or R⁵ represents C$_{1-6}$ alkyl;
- R$^a$ represents C$_{1-6}$ alkyl, C$_{3-7}$ cycloalkyl, aryl, aryl(C$_{1-6}$)alkyl, C$_{3-7}$ heterocycloalkyl, heteroaryl or heteroaryl(C$_{1-6}$)alkyl, any of which groups can be optionally substituted by one or more C$_{1-6}$ alkoxy or oxo;
- R⁶, R⁷ and Fe independently represent hydrogen, halogen, trifluoromethyl, C$_{1-6}$ alkyl or C$_{1-6}$ alkoxy; and
- R$^f$ represents hydrogen; or R$^f$ represents C$_{1-6}$ alkyl, C$_{3-7}$ cycloalkyl or C$_{3-7}$ heterocycloalkyl, any of which groups can be optionally substituted by one or more hydroxy or carboxy;
- W represents N, CH or CF;
- R¹⁰ represents hydrogen or C$_{1-6}$ alkyl; and
- R¹¹ represents a group of formula (a), (b), (c), (d), (e), (f) or (g):

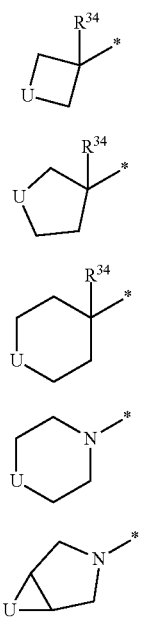

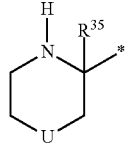

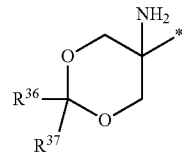

in which the asterisk (*) represents the site of attachment to the remainder of the molecule;
- U represents O, S, S(O), S(O)$_2$, S(O)(NR$^b$), N(R$^{31}$) or C(R$^{32}$)(R$^{33}$);
- R$^{31}$ represents hydrogen, cyano(C$_{1-6}$)alkyl, C$_{1-6}$ alkyl, trifluoromethyl, trifluoroethyl, C$_{1-6}$ alkylsulphonyl, (C$_{1-6}$)alkylsulphonyl(C$_{1-6}$)alkyl, formyl, C$_{2-6}$ alkylcarbonyl, carboxy, carboxy(C$_{1-6}$)alkyl, C$_{2-6}$ alkoxycarbonyl, C$_{2-6}$ alkoxycarbonyl(C$_{1-6}$)alkyl, tetrazolyl(C$_{1-6}$)alkyl, am inocarbonyl, C$_{1-6}$ alkylaminocarbonyl, di(C$_{1-6}$)alkylaminocarbonyl, aminosulphonyl, C$_{1-6}$ alkylaminosulphonyl or di(C$_{1-6}$)alkylaminosulphonyl;
- R$^{32}$ represents hydrogen, halogen, cyano, C$_{1-6}$ alkyl, hydroxy, hydroxy(C$_{1-6}$)alkyl, C$_{1-6}$ alkylsulphonyl, formyl, carboxy, carboxy(C$_{1-6}$)alkyl, C$_{2-6}$ alkoxycarbonyl, C$_{2-6}$ alkoxycarbonyl(C$_{1-6}$)alkyl, aminosulphonyl, (C$_{1-6}$)alkylsulphoximinyl, [(C$_{1-6}$)alkyl][N—(C$_{1-6}$)alkyl]sulphoximinyl, (C$_{1-6}$)alkylsulphonylaminocarbonyl, (C$_{2-6}$)alkylcarbonylamino-sulphonyl, (C$_{1-6}$)alkoxyaminocarbonyl, tetrazolyl or hydroxyoxadiazolyl;
- R$^{33}$ represents hydrogen, halogen, C$_{1-6}$ alkyl, difluoromethyl, trifluoromethyl, hydroxy, hydroxy(C$_{1-6}$)alkyl, C$_{1-6}$ alkoxy, amino or carboxy;
- R$^{34}$ represents hydrogen, halogen, halo(C$_{1-6}$)alkyl, cyano, hydroxy, C$_{1-6}$ alkoxy, C$_{1-6}$ alkylthio, C$_{1-6}$ alkylsulphinyl, C$_{1-6}$ alkylsulphonyl, amino, C$_{1-6}$ alkylamino, di(C$_{1-6}$)-alkylamino, (C$_{2-6}$)alkylcarbonylamino, (C$_{2-6}$)alkylcarbonylamino(C$_{1-6}$)alkyl, (C$_{1-6}$)alkyl-sulphonylamino or (C$_{1-6}$)alkylsulphonylamino(C$_{1-6}$)alkyl;
- R$^{35}$ represents hydrogen or C$_{1-6}$ alkyl;
- R$^{36}$ and R$^{37}$ independently represent C$_{1-6}$ alkyl; or
- R$^{36}$ and R$^{37}$, when taken together with the carbon atom to which they are both attached, represent C$_{3-7}$ cycloalkyl; and
- R$^b$ represents hydrogen or trifluoromethyl; or C$_{1-6}$ alkyl, C$_{3-7}$ cycloalkyl, C$_{3-7}$ cycloalkyl(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, heteroaryl or heteroaryl(C$_{1-6}$)alkyl, any of which groups can be optionally substituted by one or more substituents selected from C$_{1-6}$ alkoxy, C$_{1-6}$ alkylthio, C$_{1-6}$ alkylsulphinyl, C$_{1-6}$ alkylsulphonyl, hydroxy, cyano, C$_{2-6}$ alkoxycarbonyl, di—(C$_{1-6}$)alkylamino and C$_{2-6}$ alkoxycarbonylamino.

9. The compound as claimed in claim 1 selected from the group consisting of:
(7R,14R)-1142-(1-Aminocyclobutyl)pyrimidin-5-yl]-1-(difluoromethoxy)-6-methyl-6,7-dihydro-7,14-methanopyrido[3',2':4,5]imidazo[1,2-b[2,5benzodiazocin-5(14H)-one;

(7R,14R)-1-(Difluoromethoxy)-1142-(2-hydroxypropan-2-yl)pyrimidin-5-yl1-6-methyl-6,7-dihydro-7,14-methanopyrido[3',2':4,5]imidazo[1,2-b][2,5]benzodiazocin-5(14H)-one;

(7R,14R)-11-[2-(1-Aminocyclobutyl)pyrimidin-5-yl1-1-(difluoromethoxy)-6-methyl-6,7-dihydro-7,14-methanopyrido[3',4':4,51imidazo[1,2-b1[2,51benzodiazocin-5(14H)-one;

(7R,14R)-1-(Difluoromethoxy)-11-[2-(2-hydroxypropan-2-yl)pyrimidin-5-yl]-6,7-dihydro-7,14-methanopyrido[3',4':4,5]imidazo[1,2-b][2,5]benzodiazocin-5(14H)-one;

(7R,14R)-11-(2-{cis-1-Amino-3-[hydroxy(dideutero)methyl]-3-methylcyclobutyl}-pyrimidin-5-yl)-1-(difluoromethoxy)-6,7-dihydro-7,14-methanopyrido[3',2':4,51imidazo-11,2-b][2,5]benzodiazocin-5(14H)-one; and trans-3-Amino-1-{5-[(7R,14R)-1-(difluoromethoxy)-6-trideuteromethyl-5-oxo-5,6,7,14-tetrahydro-7,14-methanopyrido[3',2':4,5]imidazo[1,2-b][2,5]benzodiazocin-11-yl]-3-fluoropyridin-2-yl}-3-methylcyclobutanecarbonitrile.

10. A pharmaceutical composition comprising a compound of formula (I) as defined in claim 1 or an N-oxide thereof, or a pharmaceutically acceptable salt thereof, in association with a pharmaceutically acceptable carrier.

11. The pharmaceutical composition as claimed in claim 10 further comprising an additional pharmaceutically active ingredient.

12. A method for the treatment of rheumatoid arthritis, ankylosing spondylitis, Crohn's disease, ulcerative colitis, psoriatric arthritis or psoriasis, which comprises administering to a patient in need of such treatment an effective amount of a compound of formula (I) as defined in claim 1 or an N-oxide thereof, or a pharmaceutically acceptable salt thereof.

* * * * *